United States Patent
Fruchtl et al.

(10) Patent No.: US 11,401,496 B2
(45) Date of Patent: Aug. 2, 2022

(54) SYSTEM AND PROCESS FOR INCREASING PROTEIN PRODUCT YIELD FROM BACTERIAL CELLS

(71) Applicant: Jupeng Bio, Inc., League City, TX (US)

(72) Inventors: McKinzie Fruchtl, Prairie Grove, AR (US); Ryan Senaratne, Fayetteville, AR (US)

(*) Notice: Subject to any disclaimer, the term of this patent is extended or adjusted under 35 U.S.C. 154(b) by 539 days.

(21) Appl. No.: 16/416,127

(22) Filed: May 17, 2019

(65) Prior Publication Data

US 2019/0352672 A1    Nov. 21, 2019

Related U.S. Application Data

(60) Provisional application No. 62/674,604, filed on May 21, 2018.

(51) Int. Cl.

| | |
|---|---|
| *C12M 1/00* | (2006.01) |
| *A23L 33/195* | (2016.01) |
| *C12M 1/12* | (2006.01) |
| *A23K 10/10* | (2016.01) |
| *C07K 1/36* | (2006.01) |
| *C07K 2/00* | (2006.01) |
| *C12N 1/06* | (2006.01) |
| *C12N 1/20* | (2006.01) |
| *C12P 1/04* | (2006.01) |
| *C12P 21/00* | (2006.01) |
| *A23L 33/135* | (2016.01) |
| *C12P 7/06* | (2006.01) |

(52) U.S. Cl.
CPC .......... *C12M 47/10* (2013.01); *A23K 10/10* (2016.05); *A23L 33/135* (2016.08); *A23L 33/195* (2016.08); *C07K 1/36* (2013.01); *C07K 2/00* (2013.01); *C12M 37/02* (2013.01); *C12M 47/02* (2013.01); *C12M 47/06* (2013.01); *C12M 47/08* (2013.01); *C12N 1/06* (2013.01); *C12N 1/20* (2013.01); *C12P 1/04* (2013.01); *C12P 7/06* (2013.01); *C12P 21/00* (2013.01); *A23V 2002/00* (2013.01)

(58) Field of Classification Search
CPC .. A23J 1/008; A23J 3/20; A23K 10/10; A23K 10/12; A23K 50/10; A23K 50/30; A23K 50/40; A23K 50/75; A23K 50/80; A23L 33/135; A23L 33/195; A23V 2002/00; C07K 1/36; C07K 2/00; C12M 37/02; C12M 47/02; C12M 47/04; C12M 47/06; C12M 47/08; C12M 47/10
See application file for complete search history.

(56) References Cited

U.S. PATENT DOCUMENTS

| | | | |
|---|---|---|---|
| 3,887,431 A | 6/1975 | Robbins | |
| 5,437,986 A | 8/1995 | Alroy | |
| 5,693,296 A * | 12/1997 | Holtzapple | ............... C12P 7/10 423/165 |
| 6,136,577 A | 10/2000 | Gaddy | |
| 6,340,581 B1 | 1/2002 | Gaddy | |
| 8,178,321 B2 | 5/2012 | Rito Palomares | |
| 2010/0251608 A1 * | 10/2010 | Dumenil | ................... C10L 1/02 44/404 |
| 2010/0317074 A1 | 12/2010 | Simpson | |
| 2014/0363867 A1 | 12/2014 | Senaratne | |
| 2015/0044356 A1 | 2/2015 | Bootsma et al. | |
| 2016/0338380 A1 | 11/2016 | Simpson et al. | |

FOREIGN PATENT DOCUMENTS

WO    2017165244 A1    9/2017

OTHER PUBLICATIONS

PCT International Preliminary Report on Patentability for International application No. PCT/US2019/033396, dated Nov. 24, 2020.
PCT International Preliminary Report on Patentability for International application No. PCT/US2019/033402, dated Nov. 24, 2020.
PCT International Preliminary Report on Patentability for International application No. PCT/US2019/033406, dated Nov. 24, 2020.
PCT International Preliminary Report on Patentability for International application No. PCT/US2019/033408, dated Nov. 24, 2020.

* cited by examiner

*Primary Examiner* — Blaine Lankford
(74) *Attorney, Agent, or Firm* — James P. Krueger; Mengqi Zheng

(57) ABSTRACT

Protein-rich nutrient supplements and animal feed supplements derived from an anaerobic bacterial process are generated through a myriad of cell rupturing and protein fractionation/purification processes. Bacterial fermentation systems and methods of obtaining one or more protein-containing portions from a fermentation process using carbon monoxide-containing gaseous substrates increasing protein product yield from bacterial cells are provided. The invention further provides compositions of protein-rich nutrient supplements with useful applications for intake by a variety of different animals and humans.

14 Claims, 24 Drawing Sheets

SYSTEM AND PROCESS FOR INCREASING PROTEIN PRODUCT YIELD FROM BACTERIAL CELLS

CROSS-REFERENCE TO RELATED APPLICATIONS

This application claims benefit of U.S. provisional patent application Ser. No. 62/674,604, filed May 21, 2018, the above-referenced application is herein incorporated by reference.

BACKGROUND OF THE INVENTION

Microbial fermentation occurs when a microorganism is provided with a carbon substrate that it can utilize and process into various products, which can be recovered, separated, and purified. Chosen carbon substrates depend on the type of microorganisms used and their metabolic pathways, and the type of microorganisms used are based on identifying and selecting a microbial strain that has the capabilities to bring the type of desired products. Carbon substrates can include carbon monoxide (CO), carbon dioxide ($CO_2$), methanol, methyl, ethanol, n-alkanes, glucose, cellulose, bagasse, molasses, and sulfite waste. Useful products and substances generated by bacterial fermentation include ethanol, lactic acid, acetate, and other biofuels and chemicals, which can be used as a source of energy and a variety of additional applications.

As an example, bacterial fermentation by anaerobic microorganisms, including acetogenic microorganisms, may produce fermentation products (e.g., ethanol, butanol, acetate, butyrate, butyric acid, 2,3-butanediol, and other related products) through fermentation of gaseous substrates such as carbon monoxide (CO), hydrogen gas ($H_2$), and/or carbon dioxide ($CO_2$). Ethanol and butanol are often used as liquid fuels relating to transportation, whereas acetate and 2,3-butanediol are used in the chemical industry. Examples of bioethanol-producing acetogens used for microbial fermentation include those from the genus *Clostridium* and *Acetobacterium*. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlfi* ATCC No. 55988 and 55989.

In addition to the fermentation products, large scale microbial fermentation also produces a large amount of microbial fermentation culture broth and may require purging of a large portion of the dead or inactive cells. Recovery of excess bacterial cells from excess or purged cultural broth into microbial biomass can lead to the generation of single cell proteins (SCP) and other components for re-use as source of proteins, amino acids, and carbohydrates that are useful as a feedstock for an animal feed, and/or animal feed nutrients or supplements. All animals require amino acids, the building blocks of proteins necessary for optimal growth, reproduction, lactation, and maintenance. Amino acids absorbed in the cow's small intestine are derived from proteins that are digested in the rumen and generally its digestion system must supply 10 essential amino acids, which cannot be self-produced by the cow, including arginine, histidine, isoleucine, leucine, lysine, methionine, phenylalanine, threonine, tryptophan, and valine. Ideally, the relative proportions of each of the essential amino acids absorbed would exactly match the cow's required amino acid supply, because a shortage of one can limit the utilization of others.

However, current methods targeting single cell proteins often directly incorporate microbial cells as whole cell biomass to be used for animal feed or aquaculture. In microbial fermentation processes, the fermentation broth includes bacterial cells as well as cell debris. These methods do not differentiate the two, and often contain biomass contents which may be harmful to the animal or aquaculture (e.g., fishes or shrimps, etc). For example, microbial whole cell biomass may contain high nucleic acid content that is not suitable for ingestion or other contents that cannot not be properly digested. Most of these prior methods do not process the whole cell biomass by additional cell-rupturing or cell disruption techniques prior to incorporation the whole cell biomass into animal feeds. In addition, current methods of recovering bacterial proteins from bacterial fermentation do not yield high enough protein content suitable for nutrition-related purposes. There is a need for a method and a system for obtaining protein-rich supplements from a bacterial fermentation process, and composition of any such nutrient supplements and animal feeds.

SUMMARY OF THE INVENTION

Embodiments of the invention provide methods, systems, and compositions for producing and obtaining protein-rich nutrient supplements and/or animal feeds that are derived from microbial cell biomass after an anaerobic bacterial fermentation process using a myriad of cell rupturing and protein fractionation and purification techniques. The protein-rich nutrient supplements can be used as feedstock directly or together with other nutrients as supplements for human or animals.

In one embodiment, a bacterial fermentation system producing a protein-containing portion from a fermentation process is provided and includes one or more fermentation vessels, one or more cell separators, one or more processing chambers, one or more cell rupturing devices, and one or more fractionators. In another embodiment, the invention further provides a composition of a protein-rich nutrient supplement generated from a fermentation process using anaerobic bacteria with useful applications for intake by a variety of different animals and humans.

In still another embodiment, a method is provided for obtaining a high recovery rate of a protein-containing product purified from anaerobic bacteria cells. In one aspect, the method includes fermenting a gaseous substrate with anaerobic bacteria cells into a fermentation liquid broth inside a fermentation vessel, wherein the fermentation liquid broth is at a first pH value, separating an amount to the fermentation liquid broth being delivered from the fermentation vessel at a starting cell concentration into a cell-free permeate solution and a cell-containing suspension containing the anaerobic bacteria cells, and supplying one or more pH-adjusting agents to adjust the pH of cell-containing suspension, wherein pH of the cell-containing suspension is adjusted to a second pH value higher than the first pH value.

The method further includes rupturing cell membranes of the anaerobic bacteria cells contained within the cell-containing suspension into a homogenate having the protein-containing product at a first protein recovery rate, wherein the first protein recovery rate is a percentage of a protein concentration (grams per liter) of the protein-containing product divided by the starting cell concentration (grams per liter) and fractionating the homogenate into a first protein-containing portion at a second protein recovery rate and a protein-containing cell debris portion at a third protein recovery rate.

Another embodiment of the invention provides a system for increasing a recovery rate of a protein-containing product purified from anaerobic bacteria cells. The system includes a fermentation vessel connected to a gas inlet line for flowing a gaseous substrate into the fermentation vessel containing the anaerobic bacteria cells to ferment the gaseous substrate by the anaerobic bacteria cells into a fermentation liquid broth at a first pH value and a cell separator connected to the fermentation vessel to receive the fermentation liquid broth from the fermentation vessel and separate the fermentation liquid broth into a cell-containing suspension containing the anaerobic bacteria cells.

The system further includes one or more rupturing devices being connected to one or more first outlets of the first separator to rupture cell membranes of the anaerobic bacteria cells contained within the cell-containing suspension into a homogenate at a second pH value, wherein the second pH value is higher than the first pH value and one or more fractionators connected to the one or more rupturing devices to receive the homogenate from the one or more rupturing devices and fractionate the homogenate into one or more protein-containing portions having the protein-containing product and one or more protein-containing cell debris portions.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE INVENTION

Figure 1A:
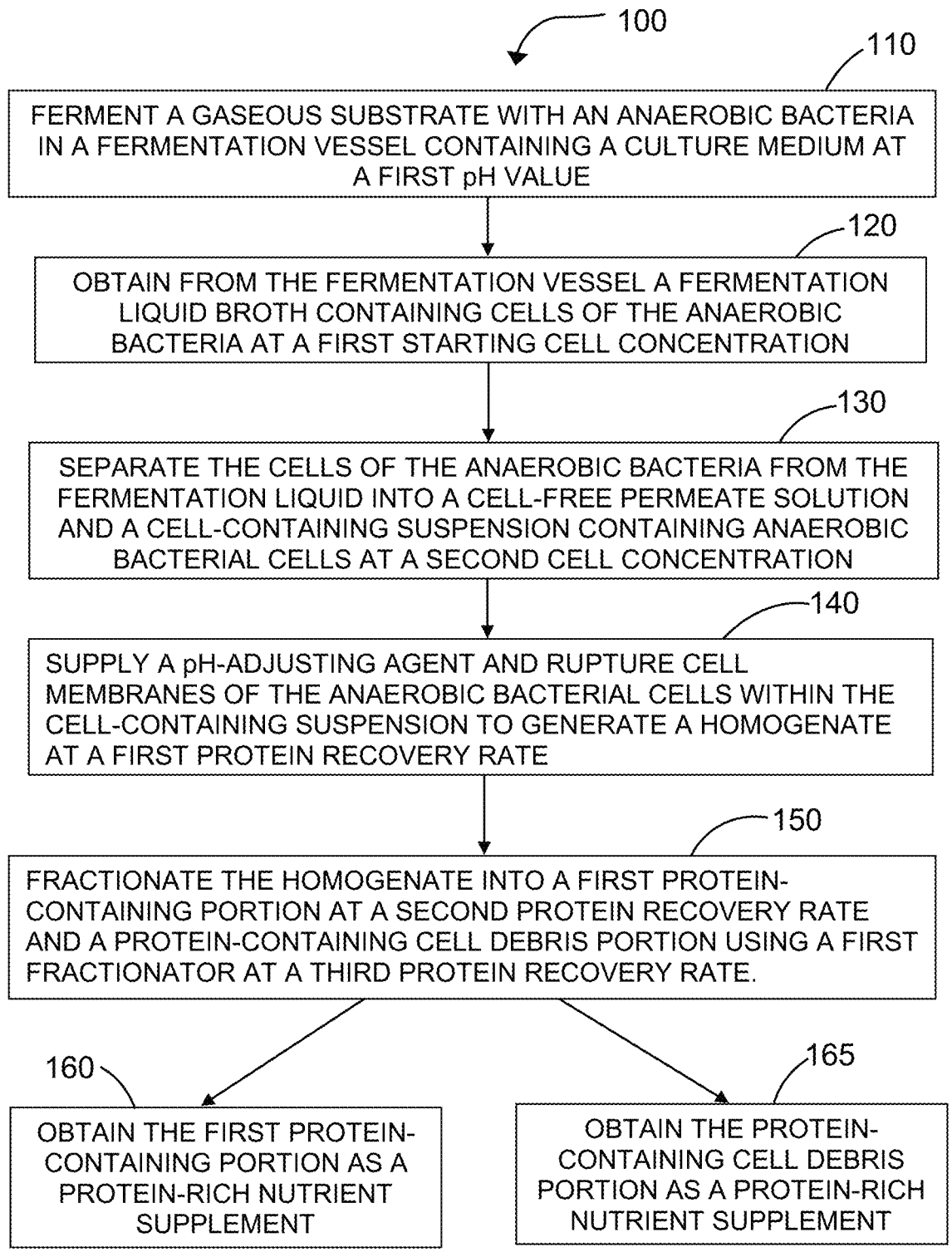
FIG. 1A illustrates a flow chart of a method of processing a cell-containing suspension from a fermentation process having a culture of an anaerobic bacteria therein and obtaining a first protein-containing portion and/or a protein-containing cell debris portion as a protein-rich nutrient supplement according to one or more embodiments of the invention.

Embodiments of the invention provide methods, systems, and compositions for increasing protein-rich nutrient supplements and/or animal feeds production that are derived from microbial cell biomass after an anaerobic bacterial fermentation process using a myriad of cell rupturing and protein fractionation and purification techniques. More specifically, the invention relates to a method of separating a microbial biomass out of a fermentation process, rupturing the cells of the microbial biomass into a homogenate and fractionating and purifying one or more protein-containing portions from the homogenate so that the one or more protein-containing portions can be further processed into a composition as a nutrient supplement ingestible by both animals and humans. The protein-rich nutrient supplements can be used as feedstock directly or together with other nutrients as supplements for human or animals.

Protein-rich nutrient supplements and animal feed supplements can be processed and obtained from one or more protein-containing portions after a fermentation process in a bacterial fermentation system using one or more gaseous substrates, such as syngas, carbon source substrates, carbon monoxide (CO)-containing gas, carbon dioxide ($CO_2$), hydrogen gas ($H_2$), syngas, and combinations thereof. The invention further provides compositions of protein-rich nutrient supplements with useful applications for intake by animals and humans.

In one aspect, a process for increasing a recovery rate of a protein-containing product purified from anaerobic bacteria cells is provided. The process includes fermenting a gaseous substrate with anaerobic bacteria cells into a fermentation liquid broth inside a fermentation vessel, wherein the fermentation liquid broth is at a first pH value, and separating the fermentation liquid broth being delivered from the fermentation vessel into a cell-free permeate solution and a cell-containing suspension containing the anaerobic bacteria cells. The process further includes supplying one or more pH-adjusting agents to adjust the pH of cell-containing suspension, wherein pH of the cell-containing suspension is adjusted to a second pH value higher than the first pH value and rupturing cell membranes of the anaerobic bacteria cells contained within the cell-containing suspension into a homogenate having the protein-containing product at a first protein recovery rate, wherein the first protein recovery rate is a percentage of a protein concentration (grams per liter) of the protein-containing product divided by the starting cell concentration (grams per liter).

In another aspect, the homogenate is fractionated into a first protein-containing portion at a second protein recovery rate and a protein-containing cell debris portion at a third protein recovery rate using a first fractionator before delivering the first protein-containing portion to a second fractionator. In still another aspect, the first protein-containing portion is fractionated into a second protein-containing portion using a second fractionator prior to collecting the second protein-containing portion.

In one embodiment, the first protein recovery rate is between 10% and 95%, such as between 30% and 85%, or between 50% and 80%. In one aspect, the second protein recovery rate is between 10% and 85%, such as between 30% and 80%. In another aspect, the third protein recovery rate is between 10% and 75%, such as between 45% and 65%. In another embodiment, the first protein-containing portion and/or the protein-containing cell debris portion can be processed and produced as protein-rich nutrient supplements. In another aspect, the first protein-containing portion is produced as a protein-rich nutrient supplement having a protein content of about 10% or larger, such as 40% or larger, 50% or larger, 60% or larger, 70% or larger, or 80% or greater, 90% or greater, such as between about 10% to about 80% of protein content, or between about 10% to about 95% of protein content, e.g., between about 10% to about 98% of protein content.

In one aspect, the second pH value is in a range of 5 to 12. In another aspect, the second pH value is in a range of 7 to 12. In one embodiment, the one or more pH-adjusting agents is selected from the group consisting of sodium hydroxide, potassium hydroxide, ammonium hydroxide, bicarbonate, hydrochloric acid, nitric acid, phosphoric acid, hydrogen chloride, and any agents that could be used to raise or lower the pH value of a solution and a combination thereof.

In one aspect, one or more pH-adjusting agents to the cell-containing suspension is added prior to the rupturing the cell membranes of the anaerobic bacteria cells. In another aspect, the one or more pH-adjusting agents to the cell-containing suspension is added after the rupturing the cell membranes of the anaerobic bacteria cells.

In still another aspect, the method may also include holding the cell-containing suspension containing the anaerobic bacterial cells in a cell-containing holding tank and delivering the cell-containing suspension from the cell-containing holding tank at a delivery rate to a rupturing device. The cell-containing holding tank can serve as a storage vessel or a pretreatment chamber for the cell-containing suspension. In one example, the cell-containing holding tank is used to conduct a pretreatment step of treating the cell-containing suspension containing the anaerobic bacterial cells with one or more additives, including pH-adjusting agents at the second pH value, supplied through an inlet line that is connected to the cell-containing holding tank. Examples of the additives include, but are not limited to a surfactant, detergent, EDTA, Tween-20, Triton X-100, sodium dodecyl sulfate, CHAPS, an enzyme, protease, lysozyme, benzonase, nuclease, a pH-adjusting agent, and a combination thereof.

In another aspect, the method further includes treating the cell-containing suspension containing the anaerobic bacterial cells with one or more additives prior to the rupturing of the cell membranes of the anaerobic bacterial cells. Alternatively, the method includes treating the cell-containing suspension containing the anaerobic bacterial cells with one or more additives after the rupturing process and prior to the separating the first protein-containing portion from the cell-containing cell debris portion.

In still another aspect, the systems and methods of the invention may further provide concentrating the cell-containing suspension containing the cells of the anaerobic bacteria into a second cell-containing suspension. In one example, the second cell-containing suspension is delivered to a cell-containing holding tank to be concentrated and/or stored therein. In another example, the second cell-containing suspension in the holding tank is subjected to a pretreatment step of treating the second cell-containing suspension containing the anaerobic bacterial cells with one or more additives supplied through an inlet connected to the cell-containing holding tank. Then, the second cell-containing suspension is delivered out of the holding tank into a rupturing device. The rupturing device ruptures the cell membranes of the anaerobic bacterial cells within the second cell-containing suspension and generates a homogenate. Additional protein-containing portions are then separated from a cell-containing cell debris portion within the homogenate.

In still another aspect, the method may further include delivering the first protein-containing portion to one or more fractionators, fractionating the first protein-containing portion into a second protein-containing portion and/or a third or more protein-containing portion using the one or more fractionators, and collecting the second and the third or more protein-containing portions. Example of fractionators includes, but are not limited to, a solid-liquid fractionator, a centrifugation device, a continuous centrifuge, a decanter centrifuge, a disc-stack centrifuge, a filtration device, a hollow fiber filtration device, a spiral wound filtration device, a ceramic filter device, a cross-flow filtration device, a size exclusion device, one or series of size exclusion columns, one or series ion exchange columns, one or series of carbon polymer columns, a flow-through magnetic fractionator, an ultrafiltration device, one or series of affinity chromatography columns, one or series of gel filtration columns, and combinations thereof.

In one embodiment, the first protein-containing portion can be delivered to a filtration device to be filtered through the filtration device and fractionated into a retentate portion and a filtrate portion so that the filtrate portion is produced as the protein-rich nutrient supplement. In another embodiment, the retentate portion is produced as the protein-rich nutrient supplement. In still another embodiment, the first protein-containing portion can be delivered to a centrifuge and fractionated into a supernatant protein-containing portion and a pellet protein-containing portion by centrifugation so that the supernatant protein-containing portion and/or the pellet protein-containing portion are produced as the protein-rich nutrient supplement.

Another embodiment of the invention provides a system for increasing a recovery rate of a protein-containing product purified from anaerobic bacteria cells. The system includes a fermentation vessel connected to a gas inlet line for flowing a gaseous substrate into the fermentation vessel containing the anaerobic bacteria cells to ferment the gaseous substrate by the anaerobic bacteria cells into a fermentation liquid broth at a first pH value and a cell separator connected to the fermentation vessel to receive the fermentation liquid broth from the fermentation vessel and separate the fermentation liquid broth into a cell-containing suspension containing the anaerobic bacteria cells.

The system further includes one or more rupturing devices being connected to one or more first outlets of the first separator to rupture cell membranes of the anaerobic bacteria cells contained within the cell-containing suspension into a homogenate at a second pH value, wherein the second pH value is higher than the first pH value and one or more fractionators connected to the one or more rupturing devices to receive the homogenate from the one or more rupturing devices and fractionate the homogenate into one or more protein-containing portions having the protein-containing product and one or more protein-containing cell debris portions.

In still another embodiment of the invention, the second pH value is higher than the first pH value by supplying one or more pH-adjusting agents into one or more first outlets of the first separator to adjust the pH of cell-containing suspension. In another embodiment, the second pH value is higher than the first pH value by supplying one or more pH-adjusting agents into one or more rupturing devices to adjust the pH of cell-containing suspension.

In one embodiment of the invention, the system further includes a holding tank connected to the one or more rupturing devices and the cell separator to receive the cell-containing suspension being outflowed from the cell separator prior to rupturing the cell membranes of the anaerobic bacteria cells. In one embodiment, the second pH value is higher than the first pH value by supplying one or more pH-adjusting agents into the holding tank and adjust a pH of the cell-containing suspension within the holding tank. In an alternative embodiment, the second pH value is higher than the first pH value by supplying one or more pH-adjusting agents into one or more second outlets of the holding tank being connected to the one or more rupturing devices to adjust the pH of cell-containing suspension within the one or more rupturing devices. In one embodiment of the invention, the second pH value is in a range of 5 to 12.

In one embodiment of the invention, the cell separator of the system is selected from the group consisting of filtration devices, hollow fiber filtration devices, spiral wound filtration devices, ultrafiltration devices, ceramic filter devices, cross-flow filtration devices, size exclusion column filtration devices, filtration devices with cross flow filters, centrifugation devices, and combinations thereof.

In one embodiment of the invention, the one or more fractionators of the system are selected from the group consisting of a solid-liquid fractionator, a centrifugation device, a continuous centrifuge, a decanter centrifuge, a disc-stack centrifuge, a filtration device, a hollow fiber filtration device, a spiral wound filtration device, a ceramic filter device, a cross-flow filtration device, a size exclusion device, one or series of size exclusion columns, one or series ion exchange columns, one or series of carbon polymer columns, a flow-through magnetic fractionator, and combinations thereof.

In one embodiment of the invention, the system further includes one or more dehydration chambers to receive one or more portions obtained from the one or more fractionators and dehydrate the one or more portions to produce the protein-rich nutrient supplement, wherein the one or more portions are selected from the group consisting of the first protein-containing portion, the protein-containing cell debris portion, and combinations thereof, wherein the one or more dehydration chambers are selected from the group consisting of a spray drying device, a drum dryer, and a freeze dryer, a lyophilization device, and combinations thereof.

In one embodiment, cell rupturing is accomplished by a microfluidizer. In another embodiment, cell rupturing is accomplished using a sonicator. In still another embodiment, cell rupturing is accomplished using a microfluidizer with a processing pressure in the range of 5,000 to 25,000 pounds per square inch (psi). In still another embodiment, cell rupturing is accomplished using a microfluidizer with a processing pressure in the range of 15,000 to 20,000 pounds per square inch (psi). In yet another embodiment, cell rupturing is accomplished using a microfluidizer with a processing pressure of 15,000 pounds per square inch (psi).

In one aspect, the bacterial fermentation system includes a first cell separator connected to the fermentation vessel and a rupturing device. The first cell separator receives a fermentation liquid at a first cell concentration from the fermentation vessel and separates the fermentation liquid into a cell-free permeate solution and a cell-containing suspension at a second cell concentration. In another aspect, the bacterial fermentation system further includes a cell-containing holding tank connected to the first cell separator to receive an amount of the first cell-containing suspension. In still another aspect, the bacterial fermentation system further includes a second cell separator connected to a fourth outlet line of the fermentation vessel to receive a second flow of the fermentation liquid broth from the fermentation vessel and separate the second flow of the fermentation liquid broth into a second cell-containing suspension and a second cell-free permeate solution.

I. Processing of Microbial Biomass to Generate Fermentation-Derived Proteins

A bacterial fermentation process generally includes fermenting a gaseous substrate, such as syngas or carbon monoxide (CO)-containing gaseous substrate by bacteria, such as an anaerobic bacteria or an acetogenic bacteria, among others, and generating fermentation products which include carbon dioxide ($CO_2$), ethanol, butanol, butyric acid, acetic acid, etc. More importantly, after an anaerobic bacterial fermentation process, large amounts of microbial biomass are obtained. The large amounts of microbial biomass can be purged during or after the bacterial fermentation process. Upon completion of the cell purge or during the bacterial fermentation process, such large amount of microbial biomass can be useful for other applications. However, further complex processing is required to extract high quantities of fermentation-derived proteins to high quality (i.e., with no harmful substances or contaminants) for them to be useful, for example, as a nutritious supplements or animal feedstock. Specifically, the present invention includes a process of extracting such fermentation-derived proteins out of a cell biomass from a bacterial fermentation process. More specifically, the present invention includes systems for a bacterial fermentation process to extract one or more fermentation-derived protein-containing portions out of cell mass or microbial biomass for processing into nutrient supplements and animal feeds.

FIG. 1A is a flow chart of one example of a method 100 of producing a protein-rich nutrient supplement from a bacterial fermentation system. The method 100 of bacterial fermentation of a gaseous substrates may be operated under conditions which favor formation of hydrocarbonaceous compounds, carbohydrates, specific proteins, specific amino acids, and/or other desired components, while maintaining desired fermentation products levels, such as alcohol productivity levels.

Step 110 includes fermenting a gaseous substrate with anaerobic bacteria in a fermentation vessel containing a culture medium at a first pH value. At step 110, a fermentation medium is added to a fermentation vessel to carry out a bacterial fermentation process. In addition, one or more gaseous substrates are delivered into the fermentation vessel and be fermented by a bacterial culture, such as a culture containing anaerobic bacteria. Initially, the liquid fermentation medium contained in the fermentation vessel may include various types of suitable bacterial culture medium, fermentation medium or liquid nutrient medium. The nutrient medium includes one or more vitamins and several minerals in an effective amount to permit growth of the microorganism used and/or to favor specific products being generated.

A culture medium suitable for anaerobic bacterial growth suitable for a fermentation process in producing one or more oxygenated hydrocarbonaceous compounds such as various types of ethanol, butanol, acetic acid, etc., among others using syngas such as carbon monoxide and hydrogen gas or another other suitable substrate can be used. One example of a suitable fermentation medium is described in U.S. Pat. No. 7,285,402, which is incorporated herein by reference. Other examples of suitable medium are described in U.S. Ser. Nos. 61/650,098 and 61/650,093, both of which are incorporated herein by reference.

In addition, the one or more gaseous substrates used in the bacterial fermentation process of the method 100 may include various synthesis gas (i.e., syngas), off-gases from a steel production process, off-gases from an iron production process, off-gases from a coal production process, or any other suitable gas sources from industrial production plants. In one embodiment, the gaseous substrates used in the bacterial fermentation process include a carbon monoxide (CO)-containing gaseous substrate and/or additional gases such as hydrogen gases, carbon dioxide (CO2), nitrogen gas (N2), and combinations thereof.

In one example, the carbon monoxide-containing gaseous substrates may be high volume carbon monoxide-containing industrial flue gases. In some aspects, a gas that includes carbon monoxide is derived from carbon-containing waste gases. Carbon-containing waste gases include industrial waste gases or the gasification of other municipal solid or liquid wastes. As such, such industrial processes represent effective processes for capturing carbon that would otherwise be exhausted into the surrounding environment. Examples of industrial flue gases include gases produced during ferrous metal products manufacturing, non-ferrous products manufacturing, petroleum refining processes, gasification of coal, gasification of biomass, electric power production, carbon black production, ammonia production, methanol production and coke manufacturing.

In one example, the carbon monoxide-containing syngas is introduced into the fermentation vessel at varying rates dependent on the size and type of fermentation vessel used. In one aspect, the syngas is introduced into the gas inlet at a rate of about 10 to about 50 ft$^3$/sec. In another aspect, syngas is introduced at a rate of about 25 to about 35 ft$^3$/sec. The term "syngas" or "synthesis gas" includes, but is not limited to, synthesis gas in a gas mixture that is rich in carbon monoxide (CO) and hydrogen (H$_2$), such as a gas mixture produced from steam reforming of natural gas or hydrocarbons to produce hydrogen, the gasification of coal, or other gases produced in some types of waste-to-energy gasification facilities. Syngas is combustible and is often used as a fuel source or as an intermediate for the production of other chemicals. Syngas can be provided from any known source.

For example, syngas may be sourced from the gasification of carbonaceous materials. Gasification involves partial combustion of biomass in an environment where the oxygen supply is restricted. The resulting gas mainly includes carbon monoxide gas and hydrogen gas. Syngas contains at least about 10 mole % carbon monoxide, or at least about 20 mole %, or 10 to about 100 mole %, or 20 to about 100 mole %, 30 to about 90 mole % carbon monoxide, or about 40 to about 80 mole % carbon monoxide, or about 50 to about 70 mole % carbon monoxide. The syngas will have a carbon monoxide/carbon dioxide molar ratio of at least about 0.75, or at least 1.0, or at least about 1.5. Suitable gasification methods and apparatuses thereof are provided in U.S. patent application Ser. Nos. 13/427,144, 13/427,193, and 13/427,247, as well as U.S. Pat. App. Nos. 61/516,667, 61/516,704, and 61/516,646, all of which are incorporated herein by reference.

Further, at step 110, a bacterial culture is inoculated into the fermentation vessel. The fermentation medium is sterilized to remove undesirable microorganisms and the bacterial fermentation vessel or fermentation bioreactor is inoculated with a chosen microorganism or mixed bacterial culture. In one aspect, the bacteria used in the bacterial culture is anaerobic bacteria. Examples of the anaerobic bacteria used includes acetogenic bacteria, such as those of the genus *Clostridium*, e.g., strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Each of these references is incorporated herein by reference. Other suitable bacteria include those of the genus *Moorella*, including *Moorella* sp. HUC22-1, and those of the genus *Carboxydothermus*. In one embodiment, a mixed bacterial culture is used, wherein the mixed bacterial culture includes two or more bacterial microorganisms.

Useful bacteria to culture in this fermentation process of method 100 include *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ERI2 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and combinations thereof. Other acetogenic or anaerobic bacteria may also be selected for use in the method 100 described herein.

In one example, the bacteria used include acetogenic bacterial cells having a genomic DNA G+C content of about 50% or less. The acetogenic bacteria may be active, inactive or a combination of both. In this aspect, G+C content may be determined by any methods known in the art. For example, the genome may be sequenced using methods such as those described in Sambrook et al. (1989) Molecular Cloning: A Laboratory Manual (Cold Spring Harbor Laboratory Press, Cold Spring Harbor) (also known as "Maniatis", which is incorporated herein by reference). G+C content may then be determined manually or by using any number of programs, such as for example, Bohlin et al. "Analysis of Intragenomic GC Content Homogeneity within Prokaryotes", BMC Genomics 2010, 11:464, which is incorporated herein by reference. Other methods for determining G+C content include U.S. Pat. No. 8,143,037, Mesbah et al. (1989) "Measurement of Deoxyguanosine/Thymidine Ratios in Complex Mixtures by High-Performance Liquid Chromatorgraphy for Determination of the Mole Percentage Guanine+Cytosine of DNA. J. Chromatogr. 479: 297-306, and Tanner et al., "*Costridium ljungdahlii* sp. *nov.*, an Acetogenic Species in Clostridial rRNA Homology Group I", International Journal of Systematic Bacteriology, April 1993, p. 232-236, all of which are incorporated herein by reference.

At step 110, upon inoculation of the bacterial culture into the fermentation vessel, an initial feed gas supply rate is established for the effective growth of the initial population of the microorganisms (e.g., the anaerobic bacteria) and subsequent fermentation. The fermentation vessel provides an environment to culture anaerobic bacteria. Suitable fermentation vessel may include, but is not limited to, one or more of the following: a continuous stirred tank reactor (CSTR), an immobilized cell reactor (ICR), a trickle bed reactor (TBR), moving bed biofilm reactor (MBBR), a bubble column, a gas lift fermenter, a membrane reactor (e.g., a hollow fiber membrane bioreactor (HFMBR)), a static mixer, a vessel, a piping arrangement, a tower, a loop reactor, and combinations thereof. In the method 100, any known fermentation vessels or fermentation bioreactors may be utilized. Some examples of bioreactors are described in U.S. Ser. Nos. 61/571,654 and 61/571,565, filed Jun. 30, 2011, U.S. Ser. No. 61/573,845, filed Sep. 13, 2011, U.S. Ser. Nos. 13/471,827 and 13/471,858, filed May 15, 2012, and U.S. Ser. No. 13/473,167, filed May 16, 2012, all of which are incorporated herein by reference.

In one embodiment, the fermentation vessel includes a first bioreactor connected to a second bioreactor, wherein the first bioreactor feeds a fermentation liquid into the second bioreactor, wherein ethanol production takes place in the second bioreactor. For example, the fermentation vessel may be a two-stage CSTR system for improved culture stability. As an example, the fermentation vessel may optionally include a first Growth Stage with a first CSTR chamber and a second Production Stage with a second CSTR chamber.

In one example, the Growth Stage CSTR is fed with a liquid culture medium and unconverted substrate gas from the Production Stage CSTR is fed into the Growth Stage CSTR. In general, the Production Stage CSTR is fed with a fresh gas feed, and a fresh medium feed as well as a bacterial culture feed from the Growth Stage CSTR. Optionally, cell recycle is used to get the bacterial cells out of the Production Stage CSTR, separated form fermentation products and sent back to the Production Stage CSTR to obtain high bacterial fermentation efficiency. In general, bacterial cells are not recycled to the Growth Stage CSTR. U.S. patent Ser. No. 10/311,655 describes a continuous fermentation process and is herein incorporated by reference. The terms "fermentation", fermentation process," "bacterial fermentation process," "fermentation reaction," "bacterial fermentation reaction" and the like are intended to encompass both the growth phase and product biosynthesis phase of the process. In one aspect, fermentation refers to conversion of carbon monoxide to alcohol. In one aspect, the bacterial fermentation process begins with the addition of a suitable fermentation medium and one or more gaseous substrates to the fermentation vessel containing bacteria therein.

In general, a fermentation liquid broth is generated inside the fermentation vessel once a bacterial fermentation process has started. The fermentation liquid broth may include one or more fermentation products, in addition to the culture medium, the one or more gaseous substrates, and the bacteria, contained inside the fermentation vessel. The fermentation products contained within the fermentation liquid broth and produced by the bacterial fermentation process inside the fermentation vessel may include one or more oxygenated hydrocarbonaceous compounds, such as alcohols, etc., including, but not limited to, ethanol, 2-butanol, 2-butanone, 2,3-butanediol, acetone, butadiene, butane, butanol, butyrate, butyric acid, ethylene, and fatty acids, acetic acids, and combinations thereof.

In one aspect, a mixture of ethanol and acetic acid can be produced. In another aspect, the mixture of ethanol and butanol are produced. In one example, ethanol is produced in the fermentation vessel at a specific productivity greater than 10 g/L per day, whereas free acetic acid concentration is kept at less than 5 g/L of free acetic acid. Ethanol and acetate found in the fermentation liquid broth may be in a ratio of ethanol to acetate ranging from 1:1 to 20:1.

The fermentation liquid broth contained inside the fermentation vessel may contain ethanol in diluted concentration and may need to be further processed in quality and/or its concentration. For example, the fermentation products contained in the fermentation liquid broth can be delivered out of the fermentation vessel and into a distillation chamber or other types of reactors to be distilled into a final distillation production at higher concentration, and further processed and recovered.

The fermentation liquid broth may also include dead or inactive bacterial cells. These bacterial cells are otherwise known as bacterial cells or cells of anaerobic bacteria. An accumulation of cells from the bacterial fermentation process in large quantity is known as cell mass or spent biomass. The term "inactive acetogenic bacteria" or "inactive bacterial cells" refers to dead cells which have lost their ability to replicate after having gone through the bacterial fermentation process. The term "cell mass" refers to bacterial cells forming a microbial biomass as a whole. The microbial biomass may accumulate during bacterial fermentation and are useful to be processed by the methods and systems described herein into fermentation-derived proteins. The fermentation liquid broth may also include various proteins, amino acids, carbohydrates, nucleic acids, and other moieties. Examples of nucleic acid include nucleotides, such as DNA, RNA and any derivatives and analogs thereof. Due to the accumulation of cell mass or microbial biomass in the fermentation broth, the fermentation broth itself may provide a significant caloric value. The fermentation liquid broth may have a dry matter content that is around 0.5%, 1%, 5%, 10%, 20%, 25%, 30%, 35%, 40%, 45%, and around 50%.

As shown in FIG. 1A, at step 120 of the method 100, an amount of a fermentation liquid broth containing cells of the anaerobic bacteria at a first concentration and the fermentation products are delivered out of the bacterial fermentation vessel. In general, when the cells reached steady-state growth inside the fermentation vessels, the fermentation liquid broth containing bacteria cells may be delivered out of the fermentation vessel. For a fermentation process after a steady-state bacterial growth stage, the first starting cell concentration of the first batch of bacterial cells contained within the fermentation liquid broth may be 0.5 g/L (dry cell mass) or higher, such 1.0 g/L or higher, or 2.0 g/L or higher, or 5.0 g/L or higher, or 15.0 g/L or higher, or 30.0 g/L or higher.

At step 130, the cells of the anaerobic bacteria from the fermentation liquid broth are separated into a cell-free permeate solution and a cell-containing suspension, using for example, one or more cell separators. At this step, the goal is to separate and remove the bacterial cells from the fermentation liquid broth and obtain the cell-free permeate solution and the cell-containing suspension separately. The cell-free permeate solution contains mainly the fermentation products generated by the fermentation process and is ready for further processing by distillation and other processes. The cell-containing suspension is comprised mainly of bacterial cells after the fermentation process. The bacterial cells within the cell-containing suspension can be measured at a second concentration (or second cell density), and in one embodiment, the second concentration of the bacterial cells within the cell-containing suspension is equal to or higher than the first concentration of the bacterial cells contained within the fermentation liquid broth.

To maintain a desired cell concentration of microbial culture in the fermentation vessel, the bacterial fermentation process includes purging a portion of the fermentation liquid broth. Increased cell concentration gives rise to operation-related problems during fermentation, e.g., an unwanted increase in the concentration of free acetic acid, such that the production of acetate becomes favored over the production of ethanol. Thus, it is important to monitor cell density and conduct periodic or continuous cell purges of the fermentation liquid broth. The term "cell density" means mass of microorganism cells per unit volume of fermentation medium, for example, grams/liter.

Stabilization of cell concentration in the bacterial fermentation vessel is accomplished by purging bacterial cells from the fermentation vessel to a cell concentration less than the stable steady state concentration that utilizes all reducing gas or nutrient substrates in the bioreactor and increasing the aqueous feed rate when the free acetic acid portion of the acetate present in the fermentation bioreactor broth exceeds a high concentration (e.g., a free acetic acid concentration of 1 g/L or higher, or 2 g/L or higher). Large scale, continuous bacterial fermentation can be maintained for a long time (e.g., for many months) by maintaining a constant cell concentration within the fermentation vessel without additional culture supplementation. Bacterial culture within the fermentation vessel is fed one or more gases (e.g., CO, $CO_2$, $H_2$, and other carbon source substrates) along with a liquid nutrient medium containing vitamins and other essential nutrients during this period.

Suitable cell separators that can be used to separate the cell-free permeate solution from the cell-containing suspension within the fermentation liquid broth include, but are not limited to, any filtration devices, hollow fiber filtration devices, spiral wound filtration devices, ultrafiltration devices, ceramic filter devices, cross-flow filtration devices, size exclusion column filtration devices, or combinations thereof. Suitable filters that can be used in the filtration-type cell separators of the invention include, but are not limited to, spiral wound membranes/filters, cross flow filters. In addition, another suitable means of cell separation from cell-free permeate is through the use of one or more centrifugation devices.

In one embodiment, the cell-separator used at step 130 functions to separate bacterial cells into the cell-containing suspension and the cell-free permeate solution and/or concentrate the cell-containing suspension to be at a higher concentration than the cell concentration within the fermentation liquid broth prior to cell separation by the cell separator. In an alternative embodiment, the cells within the fermentation liquid broth can be separated and concentrated by sending it several passes through the cell separator (e.g., by several passes through one or more filter-type filtration devices or centrifugations by one or more centrifuge several times at the same or different centrifugation speeds).

In a preferred embodiment, after cell separation, the cell concentration (or cell density) within the cell-containing suspension is higher than the cell concentration of the fermentation liquid broth. In one aspect of the invention, one or more filtration devices with spiral wound filters are used to concentrate cells by sending the fermentation liquid broth through the spiral wound filters several passes.

In another aspect, cell recycle is performed, and is generally referred to as the separation of a bacterial cell containing suspension from a cell-free liquid permeate solution and returning all or part of those separated bacterial cells back to the fermentation vessel. In one embodiment, ultrafiltration by a cell separator, such as a filtration device, is used to accomplish cell separation and/or cell recycle.

In still another aspect, during steady state bacterial growth for the bacteria cultured within the fermentation vessel, a cell purge from the fermentation vessel is conducted to collect bacterial cells into higher concentrations of the cell-containing suspension or semi-dry microbial biomass. In one embodiment, a cell purge requires an amount of fermentation liquid broth containing bacterial cells and other substances found in a fermentation medium. For example, the cell purge may be a fermentation or fermentation liquid broth removed from the fermentation vessel during bacterial fermentation. In another embodiment, the cell purge may require obtaining a concentrated cell-containing suspension by removing the fermentation liquid at a first cell concentration from the fermentation vessel and further concentrating the cells to have a cell-containing suspension at a second cell concentration. The cell-containing suspension has a higher cell density than the cell density of the fermentation liquid removed from the fermentation vessel. These steps provide for the efficient removal of certain particulates and allows for a high yield of protein content in the final protein-rich nutrient supplement that is produced from the method 100.

In one aspect, the cell purge occurs during a continuous bacterial fermentation. In another aspect, the cell purge occurs after bacterial fermentation, wherein the bacterial fermentation process is paused or stopped to permit the removal of microbial biomass from the fermentation vessel.

Next, step 140 of the method 100 includes supplying a pH-adjusting agent and rupturing cell membranes of the anaerobic bacterial cells within the cell-containing suspension to generate a homogenate at a first protein recovery rate. The pH-adjusting agent can be selected from a group consisting of sodium hydroxide, potassium hydroxide, ammonium hydroxide, bicarbonate, hydrochloric acid, nitric acid, phosphoric acid, hydrogen chloride, any agents that could be used to raise or lower the pH value of a solution, and a combination thereof.

At step 140 of the method 100, the bacterial cells contained within the cell-containing suspension are ruptured into a homogenate. A rupturing device can be used to rupture and/or lyse the cell membranes of bacterial cells within the cell-containing suspension. Examples of the rupturing deice for rupturing bacterial cells include, but are not limited to, various types of microfluidics devices, sonication devices, ultrasonic devices, mechanical disruption devices, French press, freezers, heaters, heat exchangers, distillation columns, any device that applies heat to cause a temperature change, high temperature reactors, homogenizers, and combinations thereof, among others.

As shown in FIG. 1A, after the bacterial cells within the cell-containing suspension are broken-open and/or ruptured, the resulting ruptured cell mixture, e.g., a homogenate, can be further processed at step 150 by separating out a protein-containing portion from a cell debris portion within the homogenate of the microbial biomass and further purifying and extracting additional protein-containing portions to generate a protein-rich nutrient supplement. Such separation is contemplated to be performed by the use of one or more fractionators. In one aspect, one or more protein-containing portions are obtained and the one or more protein-containing portion may also include free amino acids, total amino acids, and peptides.

At Step 150, suitable examples of the one or more fractionators for fractioning the homogenate include, but are not limited to, various types of solid-liquid fractionators, centrifugation devices, continuous centrifuges, decanter centrifuges, disc-stack centrifuges, a filtration devices, a hollow fiber filtration device, a spiral wound filtration device, a ceramic filter device, a cross-flow filtration device, a size exclusion device, one or series of size exclusion columns, one or series ion exchange columns, one or series of carbon polymer columns, a flow-through magnetic fractionator, an ultrafiltration device, one or series of affinity chromatography columns, one or series of gel filtration columns, and combinations thereof, among others.

In one embodiment, at step 150, the homogenate obtained after rupturing of bacterial cells by one or more rupturing devices is delivered to a first fractionator, and a first protein-containing portion and a first protein-containing cell debris portion are obtained. In one aspect, the first protein-containing portion has a protein content of at least 1% or more, 3% or more, 5% or more, 10% or more, 20% or more, 30% or more, 40% or more, 50% or more, 60% or more, 70% or more, 80% or more, or 95% or more.

Figure 2A:
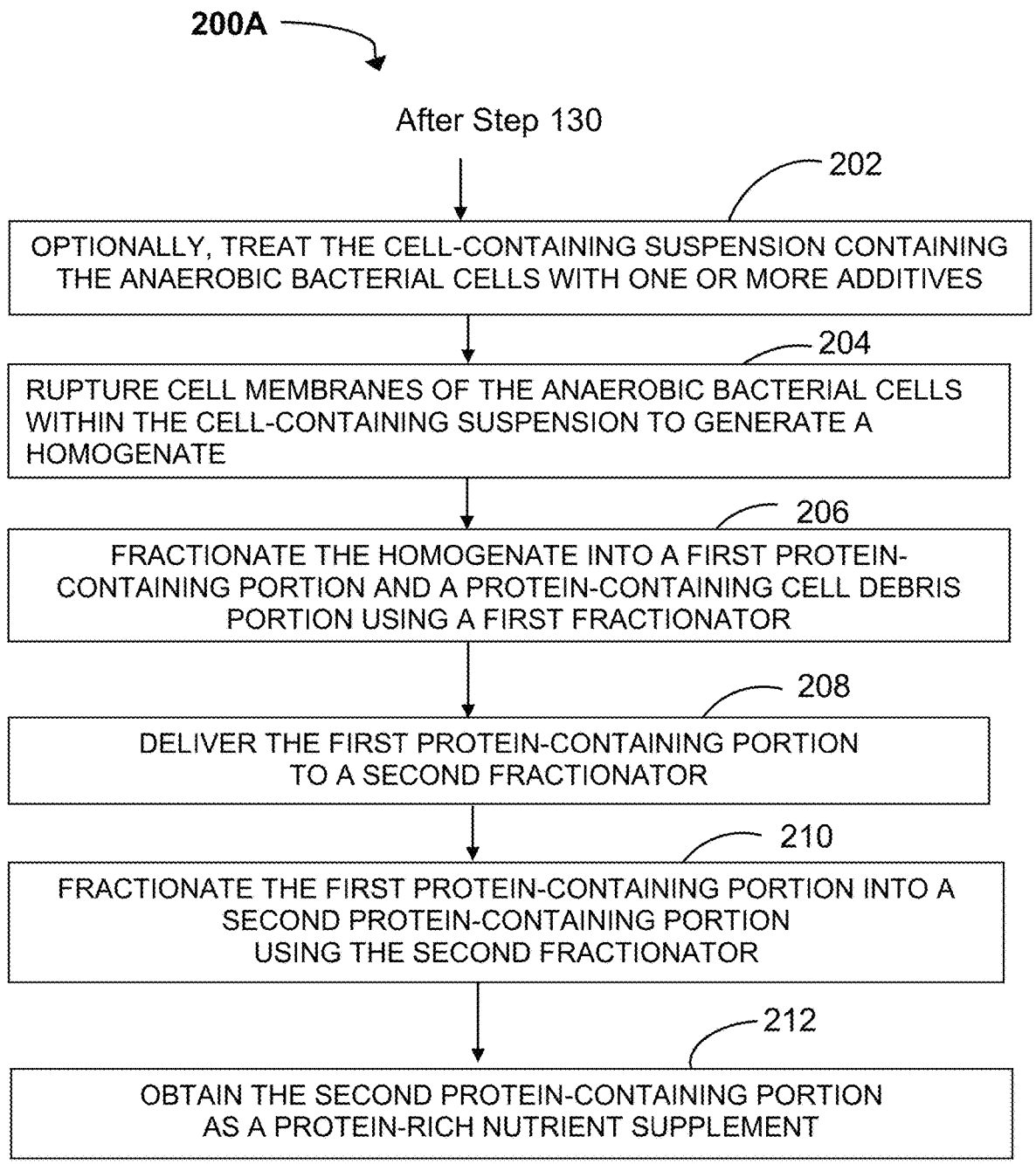
FIG. 2A illustrates a flow chart of a method of processing a cell-containing suspension from a fermentation process having a culture of an anaerobic bacteria therein and obtaining a second protein-containing portion as a protein-rich nutrient supplement according to one or more embodiments of the invention.
Figure 2B:
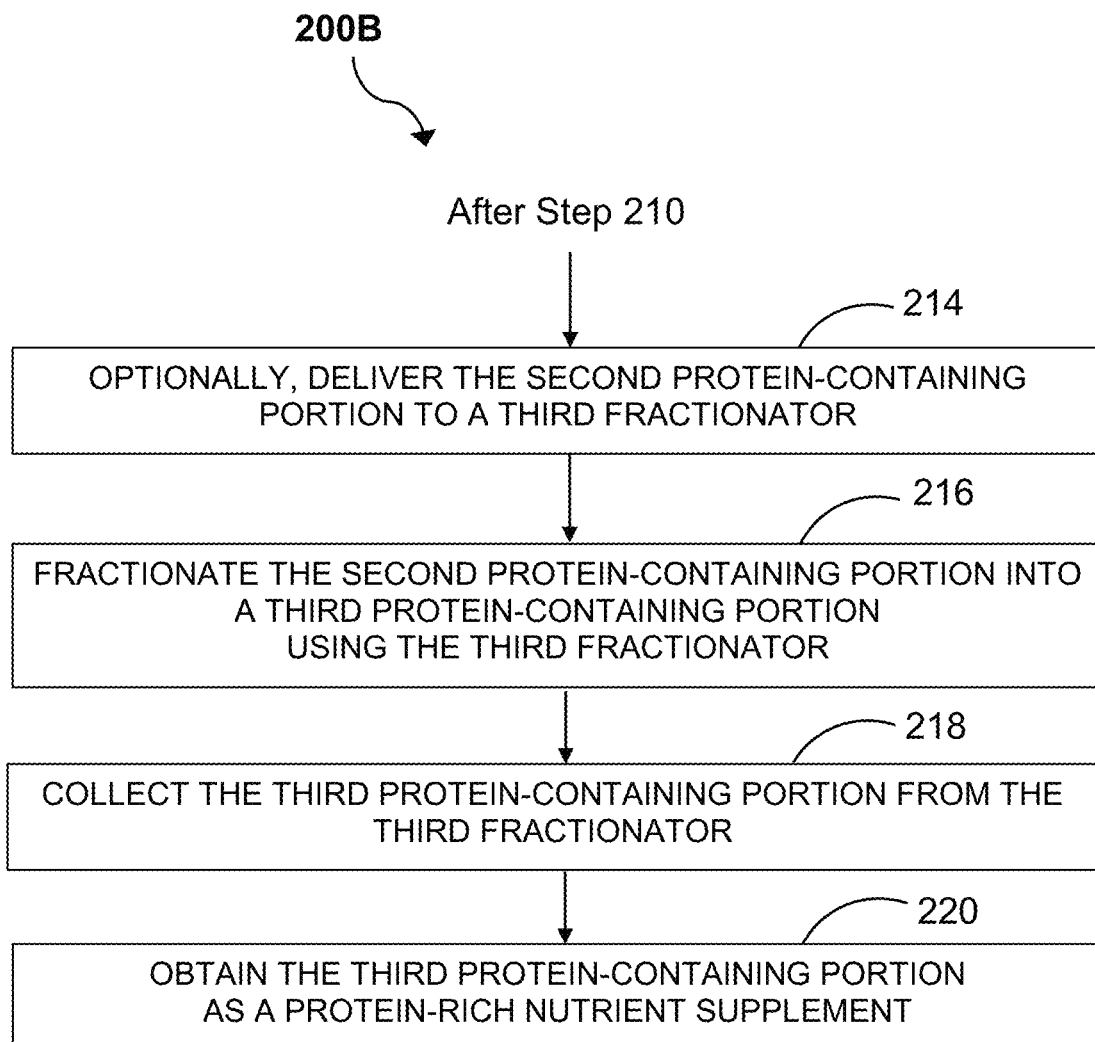
FIG. 2B illustrates a flow chart of another method of processing a cell-containing suspension from a fermentation process having a culture of an anaerobic bacteria therein and obtaining a third protein-containing portion as a protein-rich nutrient supplement according to one or more embodiments of the invention.

In one embodiment, at step 160, the first protein-containing portion derived from the homogenate can be directly incorporated into protein-rich nutrient supplement compositions, cell growth medium supplement/composition, pharmaceutical compositions, and/or an animal feed (e.g., fish feed, shrimp feed, feed for chicken, etc.). Such incorporation may require drying of the first protein-containing portion into low moisture content (e.g., paste or powder forms) and direct blending of the first protein-containing portion with other ingredients (e.g., additional animal feed nutrients, pharmaceutical fillers, blending agent, plasticizers, etc.) for making one or more types of nutrient supplements. The step 160 described herein may include additional processing steps of adjusting the pH of the first protein-containing portion, addition of one or more solubility enhancers, removal of harmful proteins from the first protein-containing portion, and/or combinations thereof to increase and enhance the quality and concentration of first protein-containing portion. In addition, the first protein-containing portion may undergo further downstream processing by performing extraction and purification of bacterial fermentation-derived protein and repurposing it for use as a protein-rich nutrient supplement. Such examples are shown in FIGS. 2A and 2B.

Alternatively, at step 165, the first protein-containing cell debris portion derived from the homogenate can be directly incorporated into protein-rich nutrient supplement compositions, pharmaceutical compositions, cell growth medium supplement/composition, and/or an animal feed (e.g., fish feed, shrimp feed, feed for chicken, etc.). Similarly, additional processing steps of adjusting the pH of the first protein-containing cell debris portion, addition of one or more solubility enhancers to the protein-containing cell debris portion, removal of harmful proteins from the first protein-containing cell debris portion, and/or combinations thereof may be needed to increase and enhance the quality and concentration of first protein-containing cell debris portion. In one aspect, if the soluble proteins of the first protein-containing cell debris portion alone are recovered, then the recovered proteins can be obtained and directly incorporated as a nutrient-rich supplement for animal intake or human intake. However, for the first protein-containing cell debris portion to be incorporated into high quality nutrient-rich supplements for human intake, further downstream processing to purify and recover nutrients and protein contents may be required. In another aspect, the insoluble proteins recovered in this method can undergo further downstream processing and then be combined with the first protein-containing portion and produced as a protein-rich nutrient supplement.

Figure 1B:
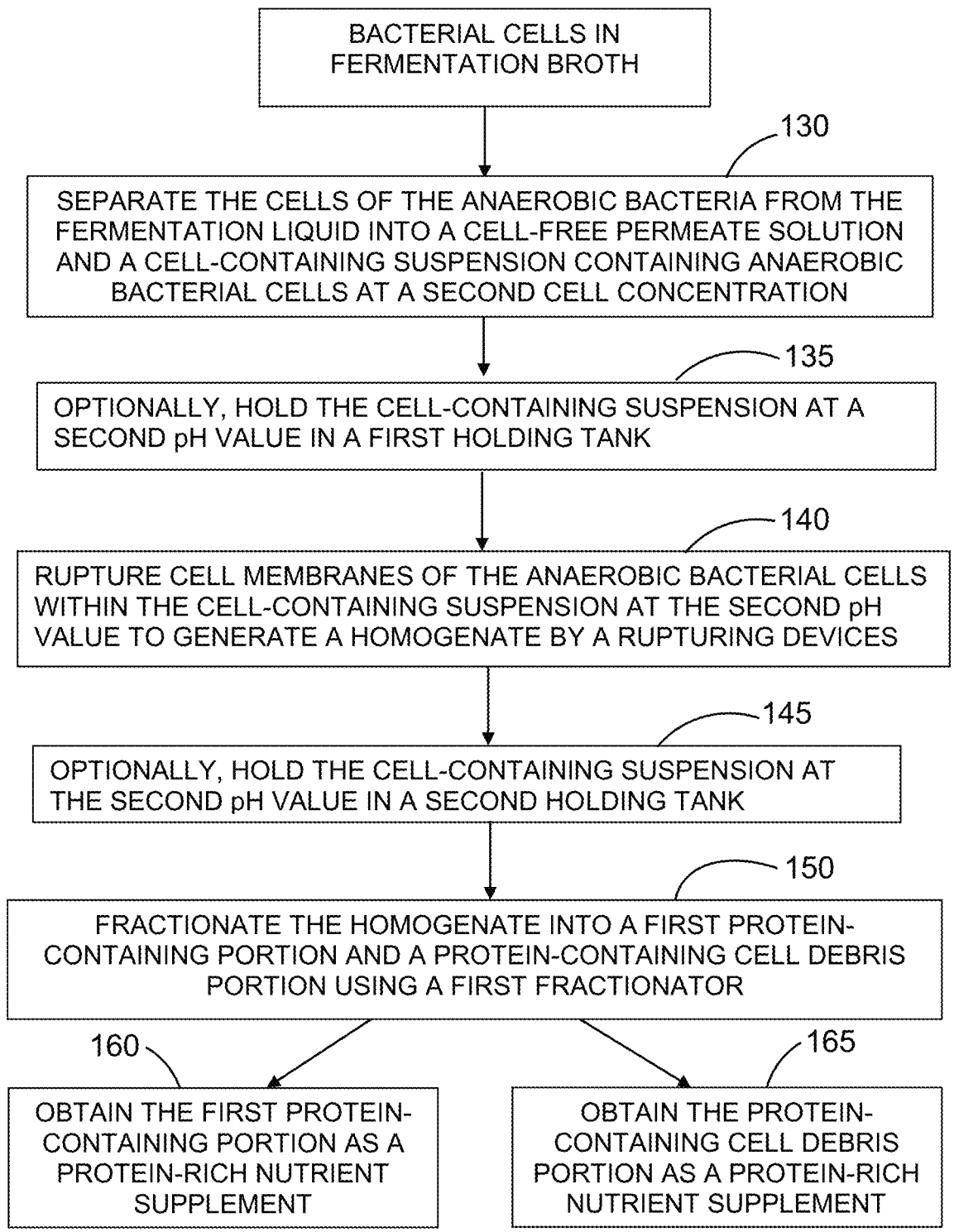
FIG. 1B illustrates a flow chart of another method of processing a cell-containing suspension from a fermentation process having a culture of an anaerobic bacteria therein and obtaining a first protein-containing portion and/or a protein-containing cell debris portion as a protein-rich nutrient supplement according to one or more embodiments of the invention.

FIG. 1B is a flow chart of another example of a method 100 of producing a protein-rich nutrient supplement from a bacterial fermentation system. The method 100 of bacterial fermentation of a gaseous substrates may be operated under conditions which favor formation of hydrocarbonaceous compounds, carbohydrates, specific proteins, specific amino acids, and/or other desired components, while maintaining desired fermentation products levels, such as alcohol productivity levels.

Step 130 of the method 100 includes separating the cells of the anaerobic bacteria from the fermentation liquid into a cell-free permeate solution and a cell-containing suspension containing anaerobic bacterial cells at a second cell concentration. Optionally, step 135 of the method 100 includes holding the cell-containing suspension at a second pH value in a first holding tank.

Step 140 of the method 100 includes rupturing cell membranes of the anaerobic bacterial cells within the cell-containing suspension at a second pH value to generate a homogenate by a rupturing device. Optionally, step 145 of the method 100 includes holding the cell-containing suspension after being ruptured at a second pH value in a first holding tank.

Step 150 of the method 100 includes fractionating the homogenate into a first protein-containing portion and a protein-containing cell debris portion using a first fractionator. Step 160 of the method 100 includes obtaining the first protein-containing portion as a protein-rich nutrient supplement. Step 165 of the method 100 includes obtaining the protein-containing cell debris portion as a protein-rich nutrient supplement.

FIG. 2A is one example of a method 200A of processing a cell-containing suspension containing anaerobic bacterial cells from a fermentation process (e.g., a cell-containing suspension at a second concentration from the step 130 of the method 100) to obtain a second protein-containing portion as a protein-rich nutrient supplement. In the method, there is an optional processing step of treating the cell-containing suspension with one or more additives at step 202 prior to rupturing the cell membranes of the aerobic cells within cell-containing suspension and generating the homogenate.

In the cell pre-treatment process of step 202, the cell-containing suspension can be processed in a pre-treatment chamber or a holding tank for pre-treatment and treated with one or more additives to assist and increase cell rupturing efficiency to break down the cell walls and cell membranes of the anaerobic bacterial cells at step 204. In one aspect, the concentrated bacterial cells enter a holding tank where they are housed until the rupturing device is ready for larger volume of cells to be processed together. In another aspect, while housed in the holding tank, the bacterial cells can undergo pretreatment in preparation of generating a protein-rich supplement with high protein content and appropriate for consumption. In still another aspect, one or more additives added in the pre-treatment process at step 202 may also help to optimize the conditions for rupturing the bacterial cells at step 204 and generate the homogenate at high quality.

Suitable additives to be used at step 202 include, but are not limited to, detergents, pH-adjusting agents, enzymes, nuclease, protease, hydrolases, alkaline buffer, acidic buffer, or combinations thereof. In one embodiment, the step 202 of the method 200A includes reducing the nucleic acid content of the cell-containing suspension of fermentation-derived bacterial cells. Such pretreatment process is accomplished by treating the bacterial cells with nucleases. Examples of nucleases used include, but are not limited to, deoxyribonucleases, ribonucleases, benzonases, and nuclease. Nuclease treatment of the cell-containing suspension can be further assisted by alkaline hydrolysis and chemical extraction, such as ammonium sulfate precipitation, ethanol precipitation, polyethyleneimine precipitation. In one aspect, the nucleic acid content of the cell-containing suspension is reduced to about 1.5% to 5%, or about 2% to 18%.

At step 206, after cell rupturing, the homogenate can be subjected to additional extraction and purification processes, such as being fractionated into the first protein-containing portion and a protein-containing cell debris portion using a first fractionator. Example of the first fractionator for fractioning the homogenate includes, but are not limited to, various types of solid-liquid fractionators, centrifugation devices, continuous centrifuges, decanter centrifuges, disc-stack centrifuges, a filtration devices, a hollow fiber filtration device, a spiral wound filtration device, a ceramic filter device, a cross-flow filtration device, a size exclusion device, one or series of size exclusion columns, one or series ion exchange columns, one or series of carbon polymer columns, a flow-through magnetic fractionator, an ultrafiltration device, one or series of affinity chromatography columns, one or series of gel filtration columns, and combinations thereof, among others.

Alternatively, the cell-containing suspension of concentrated bacterial cells may go directly to a rupturing device at step 204 and are then subjected to pre-treatment process as mentioned at step 202 to help optimize the conditions for separating and fractionating the homogenate at step 206. In another aspect, the proteins recovered from the method 200A can undergo further downstream processing and then be combined with the first protein-containing portion and produced as a protein-rich nutrient supplement.

At step 208, the first protein-containing portion is delivered to a second fractionator and fractionated into a second protein-containing portion using the second fractionator at step 210. Examples of the second fractionator for fractioning the protein-containing portion include, but are not limited to, various types of solid-liquid fractionators, centrifugation devices, continuous centrifuges, decanter centrifuges, disc-stack centrifuges, a filtration devices, a hollow fiber filtration device, a spiral wound filtration device, a ceramic filter device, a cross-flow filtration device, a size exclusion device, one or series of size exclusion columns, one or series ion exchange columns, one or series of carbon polymer columns, a flow-through magnetic fractionator, an ultrafiltration device, one or series of affinity chromatography columns, one or series of gel filtration columns, and combinations thereof, among others.

At step 212, the second protein-containing portion obtained can be formulated into a protein-rich nutrient supplement, pharmaceutical compositions, cell growth medium/composition, and/or an animal feed (e.g., fish feed, shrimp feed, feed for chicken, etc.). Such incorporation may require drying of the second protein-containing portion into low moisture content (e.g., paste or powder forms) and direct blending of the second protein-containing portion with other ingredients (e.g., additional animal feed nutrients, pharmaceutical fillers, blending agent, plasticizers, etc.) for making one or more types of nutrient supplements.

As an example, the homogenate from step 204 may enter a filtration device to yield a first protein-containing portion (e.g., the filtrate protein-containing portion after filtration by the filtration device). The filtrated protein-containing portion is a partially purified protein product. In one embodiment, the filtrated protein-containing portion is then centrifuged (e.g., by a second fractionator/centrifuge) to yield additional soluble protein fractions and cell solids portions. Such second protein-containing portions can be used individually or in combination as the protein-rich nutrient supplements.

As another example, the homogenate from step 204 may undergo centrifugation, after which a supernatant protein-containing portion is collected. The supernatant protein-containing portion enters a filtration device, wherein a second filtrate protein-containing portion is collected. As yet another example, the first protein-containing portion only enters a filtration device, after which a filtrate protein-containing portion is collected and used as a protein-rich supplement. As yet another example, the first protein-containing portion only undergoes centrifugation, after which a fractionated protein or supernatant is collected as the protein-containing portion. Separation of one or more protein-containing portions and cell-debris proteins is accomplished by one or more fractionators.

In one aspect, a fermentation system that has two fractionators is used. In another embodiment, a fermentation system that has three fractionators is used. FIG. 2B is one example of a method 200B of processing a cell-containing suspension from a fermentation process where three fractionators are used to obtain a third protein-containing portion as a protein-rich nutrient supplement according to one or more embodiments of the invention.

As shown in FIG. 2B, the method 200B includes delivering the second protein-containing portion to a third fractionator at step 214 and a third protein-containing portion is fractionated from and extracted out of the second protein-containing portion at step 216. The third protein-containing portion is collected at step 218 and the third protein-containing portion is collected and obtained as a protein-rich supplement at step 220.

As an example, the second protein-containing portion from step 210 may be delivered to a third fractionator (e.g., a filtration device) to yield a filtrate protein-containing portion collected and used as a protein-rich supplement. As another example, the second protein-containing portion undergoes centrifugation, after which a supernatant protein-containing portion and a pellet cell debris portion are collected. The filtrate protein-containing portion is collected from the filtration device and produced as the protein-rich nutrient supplement with a protein content of around 1 to 3%, 3% to 7%, 7% to 10%, around 10% to 14%, around 11% to 20%, around 21% to 35%, and around 35% or more.

In one embodiment, one or more protein-containing portions obtained from steps 160, 165, 212, 220 are delivered to a dehydration chamber, after which a dehydrated protein-containing portion is collected and produced as a protein-rich nutrient supplement. Alternatively, there are two or more dehydration chambers, wherein each protein-containing portion from each step is delivered to a separate, individual dehydration chamber. The dehydration chamber receives the protein-containing portions and dries them into low moisture paste forms or dry power forms, ready to be blended into protein-rich nutrient supplements for human intake and/or animal feeds. Suitable examples of the dehydration chambers include, but are not limited to, an oven dryer, a spray drying chamber, a drum dryer, and a freeze dryer, a lyophilization device, a vacuum dryer, and combinations thereof.

In one embodiment, the present invention is a method of producing a protein-rich nutrient supplement from a fermentation process using anaerobic bacteria. The method includes fermenting a gaseous substrate with anaerobic bacteria in a fermentation vessel, obtaining from the fermentation vessel an amount of a fermentation liquid containing cells of the anaerobic bacteria at a first concentration, separating the cells of the anaerobic bacteria from the fermentation liquid into a cell-free permeate solution and a cell-containing suspension containing anaerobic bacterial cells at a second concentration, rupturing cell membranes of the anaerobic bacterial cells within the cell-containing suspension into a homogenate, and separating a first protein-containing portion from a cell debris portion within the homogenate.

In one aspect, the method includes fermenting a gaseous substrate with anaerobic bacteria in a fermentation vessel. The gaseous substrate is a CO-containing gaseous substrate of one or more gases that flows into the fermentation vessel. The one or more gases used is selected from the group consisting of carbon source substrates, carbon monoxide (CO), carbon dioxide ($CO_2$), hydrogen ($H_2$) gas, syngas, and combinations thereof. Anaerobic bacteria include, but are not limited to, one or more strains of acetogenic bacteria, such as from the genus *Clostridium, Acetobacterium*, and similar variants thereof. The fermentation vessel provides an environment that is hospitable for culturing *Clostridium* bacteria, wherein there is a fermentation medium that flows into the fermentation vessel to provide nutrients, vitamins, and other essential minerals to the bacteria.

The method further includes obtaining from the fermentation vessel an amount of a fermentation liquid containing cells of the anaerobic bacteria at a first cell concentration. Collections of the fermentation liquid may be sent to one or more apparatuses within the bacterial fermentation system. In one aspect, subsequent manipulated amounts of fermentation liquid are at a second, third, and fourth cell concentration. In most aspects, the second cell concentration of a manipulated fermentation liquid is greater than the first cell concentration of a first fermentation liquid.

The method further includes a first cell separator receiving an amount of fermentation liquid that contains anaerobic bacterial cells. The first cell separator separates the fermentation liquid into a first cell-containing suspension containing anaerobic bacterial cells and a first cell-free permeate solution. The fermentation liquid delivered to first cell separator has a first cell concentration. The first cell-containing suspension generated by the first cell separator has a second cell concentration. The second cell concentration of the first cell-containing suspension is higher than the first cell concentration of the fermentation liquid. The first cell-free permeate solution is sent to a processing chamber connected to the first cell separator. In some aspects, some of the first cell-containing suspension is sent back to the fermentation vessel.

In another aspect, a first flow of the first fermentation liquid is sent to a first cell separator to further process for ethanol production. A second flow of the second fermentation liquid is sent to a second cell separator to further process for the production of a protein-containing product that can be used as a protein-rich nutrient supplement.

The method of the present invention provides a simultaneous approach of generating a high productivity of ethanol production, while re-purposing useful moieties found within bacterial cells used in the fermentation process. The fermentation liquid collected is at a first concentration of anaerobic bacterial cells. The cell separator generates a cell-containing suspension at a second concentration of anaerobic cells. In one embodiment, the cell separator sends the cell-containing suspension at a second concentration to a rupturing device. In another embodiment, the cell separator sends the cell-containing suspension to a holding tank.

Once a collection is made, the collection can be further processed to separate the cells of the anaerobic bacteria from the fermentation liquid into a cell-free permeate solution and a cell-containing suspension containing the anaerobic bacterial cells at a second concentration. The second concentration of the cell-containing suspension is higher than the first concentration of fermentation liquid containing anaerobic bacterial cells. The cell-free permeate solution is sent back to a processing chamber that distills ethanol for ethanol production. This provides for an efficient system that does not discard still useful cell-free permeate solution containing ethanol.

The method further includes rupturing cell membranes of the anaerobic bacterial cells within the cell-containing suspension into a homogenate. In one aspect, this takes place in a rupturing device. The cell-containing suspension containing cells of anaerobic bacteria enters the rupturing device, wherein the cell-containing suspension is subjected to high forces (e.g., mechanical, sound, or pressure). The high shear force ruptures the cell membranes of the cells, causing the cells to break open and for the contents of the cells to be free-floating as they enter the cell-containing suspension. The rupturing device generates a homogenate that can be further processed to obtain a first protein-containing portion. The homogenate contains several moieties generally found in fermentation-derived bacterial cells, including proteins, metals (e.g., Ca, Cl, Co, K Mg, Ni, P, S, Se, W, Zn, Na, Fe), lipids, nucleic acids, and sugars.

To obtain a first protein-containing portion, the method further includes separating a first protein-containing portion from a cell debris portion within the homogenate. In one aspect, the homogenate is centrifuged, and then filtered, to yield a first protein-containing portion. The first protein-containing portion is delivered to a first fractionator, which separates a second protein-containing portion from the first protein-containing portion and allows collection of a second protein-containing portion from the first fractionator.

In one aspect, the method includes dehydrating the first protein-containing portion separated from the cell debris portion of the homogenate. In this aspect, the system has a dehydration chamber connected to a first fractionator. The first fractionator delivers the first protein-containing portion into the dehydration chamber, wherein the dehydration chamber generates a dried protein-containing portion produced as a protein-rich nutrient supplement.

In another aspect, the method includes dehydrating the cell debris portion of the homogenate. In this aspect, the rupturing device delivers the cell debris portion into a dehydration chamber, to be prepared for further downstream processing. The cell debris portion is an insoluble fraction containing a high level of protein content. Typically, this includes cell wall or cell membrane components that are insoluble. It may also contain small concentrations of nucleic acid or protein aggregates. In most aspects, the majority of the nucleic acid is released into the first protein-containing portion. Sometimes these protein aggregates are difficult to solubilize and will remain in the cell debris portion. Determinations of protein content in the first protein-containing portion and the cell debris portion is based on an assumption of mass balance around the total cell mass and the protein amounts, soluble and insoluble. By way of example, a calculation of insoluble protein recovery includes subtracting the mass of the soluble protein from the total cell mass to yield an approximation of the insoluble mass.

II. Bacterial Fermentation Systems for Processing an Acetogenic Biomass to Yield a Fermentation-Derived Protein The bacterial fermentation system includes, but is not limited to, one or more inlet lines for delivering pH adjusting agents into the system, a bacterial fermentation vessel, one or more rupturing devices, one or more cell separators, and one or more fractionators. In addition, one or more dehydration chambers are connected to the one or more rupturing devices and/or the one or more fractionators to increase the protein-concentration of the protein-containing portions obtained and reduce their moisture content. Optionally, the bacterial fermentation system further includes one or more holding tanks, storage chambers, and/or pre-treatment chambers for holding bacterial cells or cell-containing suspensions.

Figure 3A:
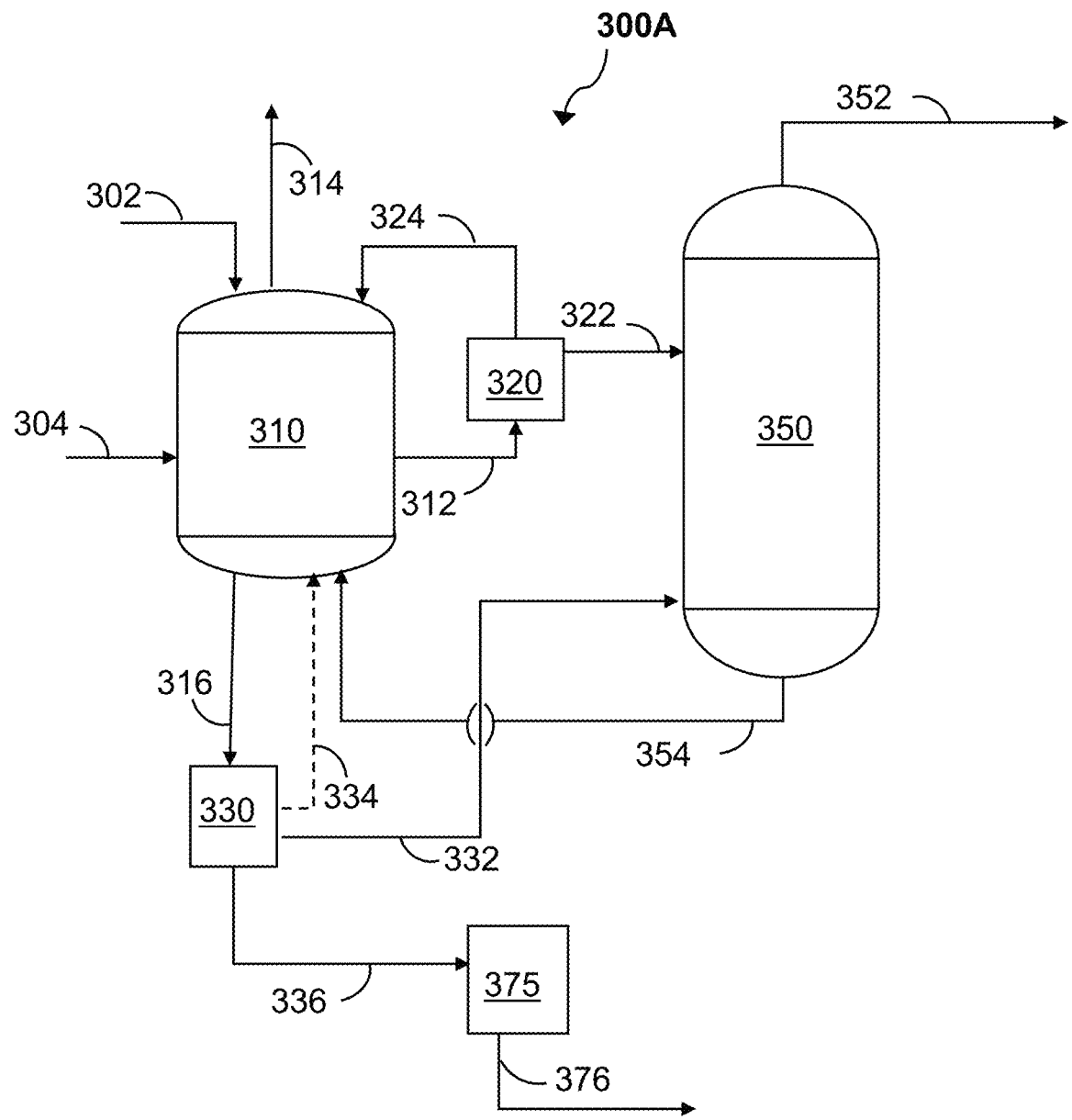
FIG. 3A illustrates a schematic of a bacterial fermentation system 300A for producing a cell-containing suspension and one or more oxygenated hydrocarbonaceous compounds from a fermentation process using a culture of an anaerobic bacteria, where the bacterial fermentation system 300A includes one or more cell separators, one or more processing chambers, and optionally, one or more dehydration chambers, according to one or more embodiments of the invention.

FIGS. 3A-3B, 4A-4H, 5A-5E, and 6 illustrate such exemplary bacterial fermentation systems for producing a cell-containing suspension and one or more oxygenated hydrocarbonaceous compounds from a fermentation process using a culture of an anaerobic bacteria. FIG. 3A is a schematic of a bacterial fermentation system 300A for producing a cell-containing suspension and one or more oxygenated hydrocarbonaceous compounds, where two cell separators and one dehydration chamber are used.

In FIG. 3A, the bacterial fermentation system 300A includes a fermentation vessel 310, a cell separator 320, a cell separator 330, a processing chamber 350, and optionally, a dehydration chamber 375. The bacterial fermentation system 300A can be, in one embodiment, a continuous bacterial fermentation system. Alternatively, the bacterial fermentation system 300A can be, a batch bacterial fermentation system.

Two or more inlet lines, e.g., an inlet line 302 and an inlet line 304, are connected to the fermentation vessel 310. The inlet line 302 can be used for delivery of gaseous substrates, additional supplements, and/or other solid or liquid substrates into the fermentation vessel 310. The inlet line 304 can be used for delivery of a fermentation medium or other culture medium into the fermentation vessel 310. Conversion of the gaseous substrates and the fermentation medium takes place in the fermentation vessel 310. The fermentation medium used herein includes conventional bacterial growth media containing vitamins, salts, and minerals sufficient to permit growth of selected anaerobic bacteria. Vitamins in the form of a vitamin cocktail are added into the fermentation medium. Vitamins include several from the B vitamin family, including, but not limited to, thiamine (B1), pantothenic acid (B5), biotin (B7), other amino acids and combinations thereof.

Inside the fermentation vessel 310, the gaseous substrates and the fermentation medium are fermented by the anaerobic bacteria contained within the fermentation vessel 310 into a fermentation liquid broth, containing cells of the anaerobic bacteria at a first concentration. The reactor gas is then released from the bacterial fermentation system 300A by the outlet line 314. The fermentation vessel 310 provides an environment to ferment the gaseous substrate with anaerobic bacteria. In one aspect, the gaseous substrate is one or more gases consisting of carbon source substrates, carbon monoxide (CO), carbon dioxide ($CO_2$), hydrogen gas ($H_2$), and syngas, whereas the anaerobic bacteria is one or more anaerobic bacterium selected from the genus *Clostridium, Acetobacterium*, and variants thereof.

The fermentation vessel 310 may include three or more outlet lines, e.g., an outlet line 314, an outlet line 316, and an outlet line 312. The outlet line 314 can be used for delivery of gases, vent gases, extra gases to be exhausted out of the fermentation vessel 310. The outlet line 312 can be used for delivery of a portion of the fermentation liquid broth out of the bacterial fermentation system 300A to the cell separator 320. The outlet line 316 can be used for delivery of a portion of the fermentation liquid broth out of the bacterial fermentation system 300A to the cell separator 330. Portions of the fermentation liquid broth from the fermentation vessel 310 are delivered and supplied to the cell separator 320 and cell separator 330, each by outlet line 312 and outlet line 316, respectively. Inside each of the cell separator 320 and cell separator 330, the cells of the anaerobic bacteria contained within the fermentation liquid broth (containing bacterial cells at a first concentration) are separated into a cell-free permeate solution and a retentate solution (e.g., a cell-containing suspension containing anaerobic bacteria cells at a second concentration).

An outlet line 322 and an outlet 332 are used to deliver cell-free permeate solutions out of the cell separator 320 and a cell separator 330, respectively, and into the processing chamber 350. Inside the processing chamber 350, the cell-free permeate solution is processed into an oxygenated hydrocarbonaceous compound. The processing chamber 350 may also recycle distillation aqueous contents, including water, back to the fermentation vessel 310 through an outlet line 354. In one example, the distillate may mainly include water, and may also contain other contents. For example, general distillation aqueous stream contains 95% of water, about 5% of acetic acid, and some other contents. Then, the processing chamber 350 sends out a final product of an oxygenated hydrocarbonaceous compound through an outlet line 352 for further downstream processing. In one embodiment, the processing chamber 350 is a distillation chamber where cell-free permeate solution is processed and distilled into high quality oxygenated hydrocarbonaceous compound (e.g., high concentration and/or anhydrous form of ethanol, butanol, such as 95% w/w or higher concentration of ethanol, etc).

The cell-containing suspension obtained after passing through the cell separator 320 can be delivery via an outlet line 324 back to the fermentation vessel 310 for cell recycle so that the cells within the cell-containing suspension may undergo further fermentation process. On the other hand, the cell-containing suspension obtained after passing through the cell separator 330 can be concentrated by the cell separator 330 and delivered via an outlet line 336 to the dehydration chamber 375 to be ruptured into a mixture and dried. The dehydration chamber 375 can be an oven dryer, a paddle dryer, a spray drying device, a drum dryer, a lyophilization device, and combinations thereof. A portion of the cell-containing suspension, containing anaerobic bacteria cells, in the cell separator 330 is then delivered back to the fermentation vessel 310 via an outlet line 334 for further fermentation process.

One example of processing of the cell-containing suspension into a protein-rich supplement is to subject the cell-containing suspension at a high temperature of about 100 degree Celsius or higher (e.g., at 250 degree Celsius or higher) inside a high temperature processing chamber, e.g., the spray drying dehydration chamber, to rupture the cells and reduce moisture content of the cell-containing suspension into paste or powder forms. Another example of processing of the cell-containing suspension is to subject the cell-containing suspension at a temperature of about 0 degree Celsius or lower inside a low temperature processing chamber.

An outlet line 376 is connected to the dehydration chamber 375 to deliver the ruptured and dehydrated form of the cell-containing suspension out of the dehydration chamber 375 to be ready for blending into compositions of protein-rich supplements. After the dehydration process is undergone in the dehydration chamber 375, a protein-rich nutrient supplement is obtained and collected from the bacterial fermentation system 300A via the outlet line 376.

Figure 3B:
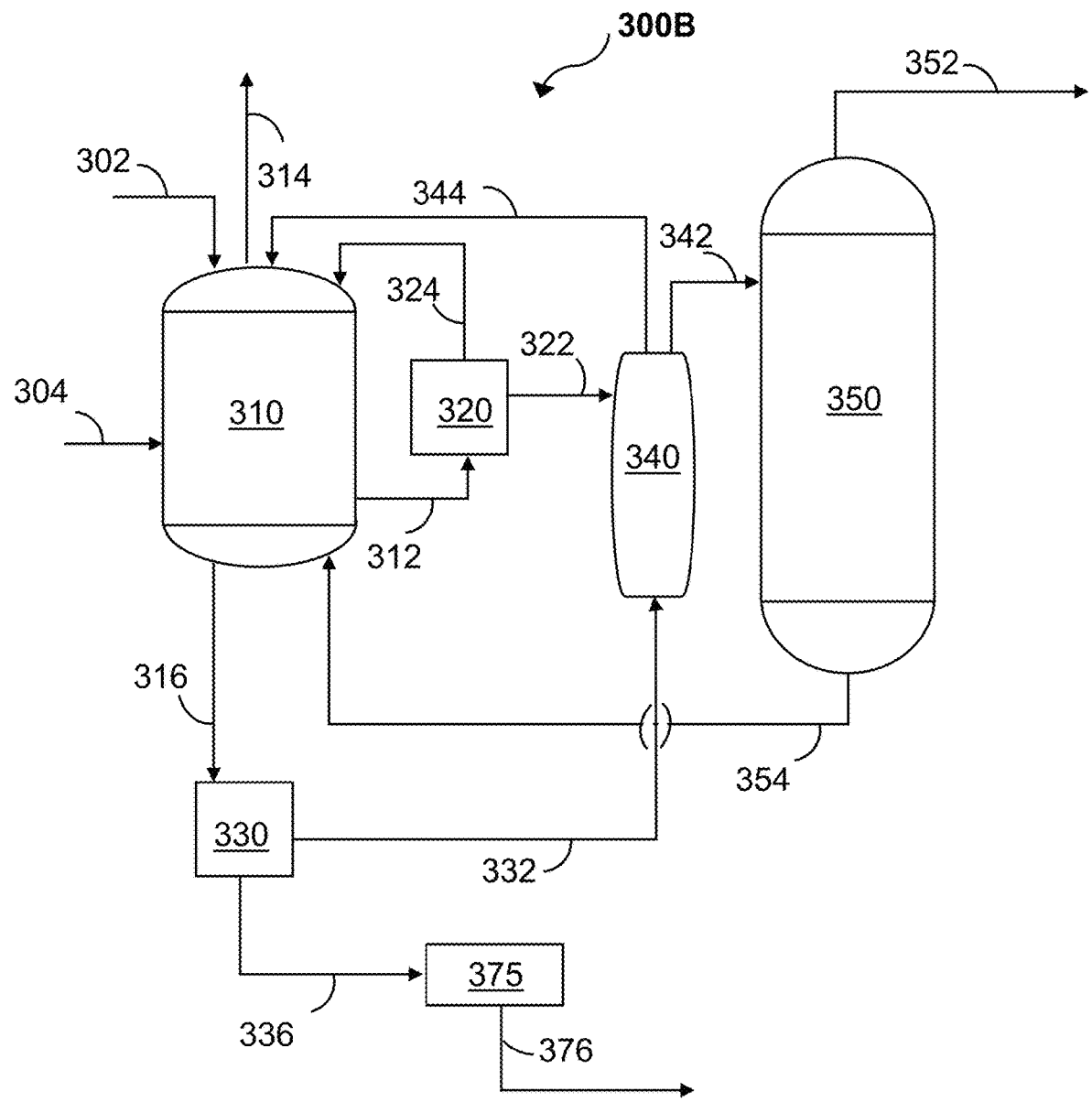
FIG. 3B illustrates a schematic of a bacterial fermentation system 300B for producing one or more cell-containing suspensions and one or more oxygenated hydrocarbonaceous compounds from a fermentation process using a culture of an anaerobic bacteria, where the bacterial fermentation system 300B includes two cell separators, a cell-free holding tank, a processing chamber, and optionally, a dehydration chamber, according to one or more embodiments of the invention.

FIG. 3B is a schematic of a bacterial fermentation system 300B for producing a cell-containing suspension and one or more oxygenated hydrocarbonaceous compounds, where two cell separators, one holding tank and one dehydration chamber are used. In FIG. 3B, the bacterial fermentation system 300B includes the fermentation vessel 310 connected to the inlet line 302, the inlet line 304 and several outlet lines, the cell separator 320 connected to the outlet line 312, the outlet line 322, and the outlet line 324, the cell separator 330 connected to the outlet line 316 and the outlet line 336, and the dehydration chamber 375 connected to the outlet lines 336 and the outlet line 376, as discussed above.

In addition, the bacterial fermentation system 300B further includes a holding tank or a storage tank for holding and storing portions of the cell-free permeate solutions. For example, a holding tank 340 (e.g., a cell-free permeate holding tank) is connected to the cell separator 320 and the cell separator 330 via the outlet line 322 and an outlet line 332, respectively. The cell-free permeate solutions obtained after cell separation by the cell separator 320 and the cell separator 330 can undergo pretreatment or storage into large quantity in preparation for processing the cell-free permeate solutions being held in the holding tank 340 into a final product of high-quality form of an oxygenated hydrocarbonaceous compound. In one embodiment, the cell-free permeate solution is further processed for ethanol production within a processing chamber 350 being delivered from holding tank 340 via an outlet line 342. Afterward, processed final products of oxygenated hydrocarbonaceous compounds are delivered out of the processing chamber 350 via the outlet line 352, and water, acetic acid, nutrients, and other materials produced from the processing chamber 350 can be recycled back to the fermentation vessel 310 via an outlet line 354.

Figure 4A:
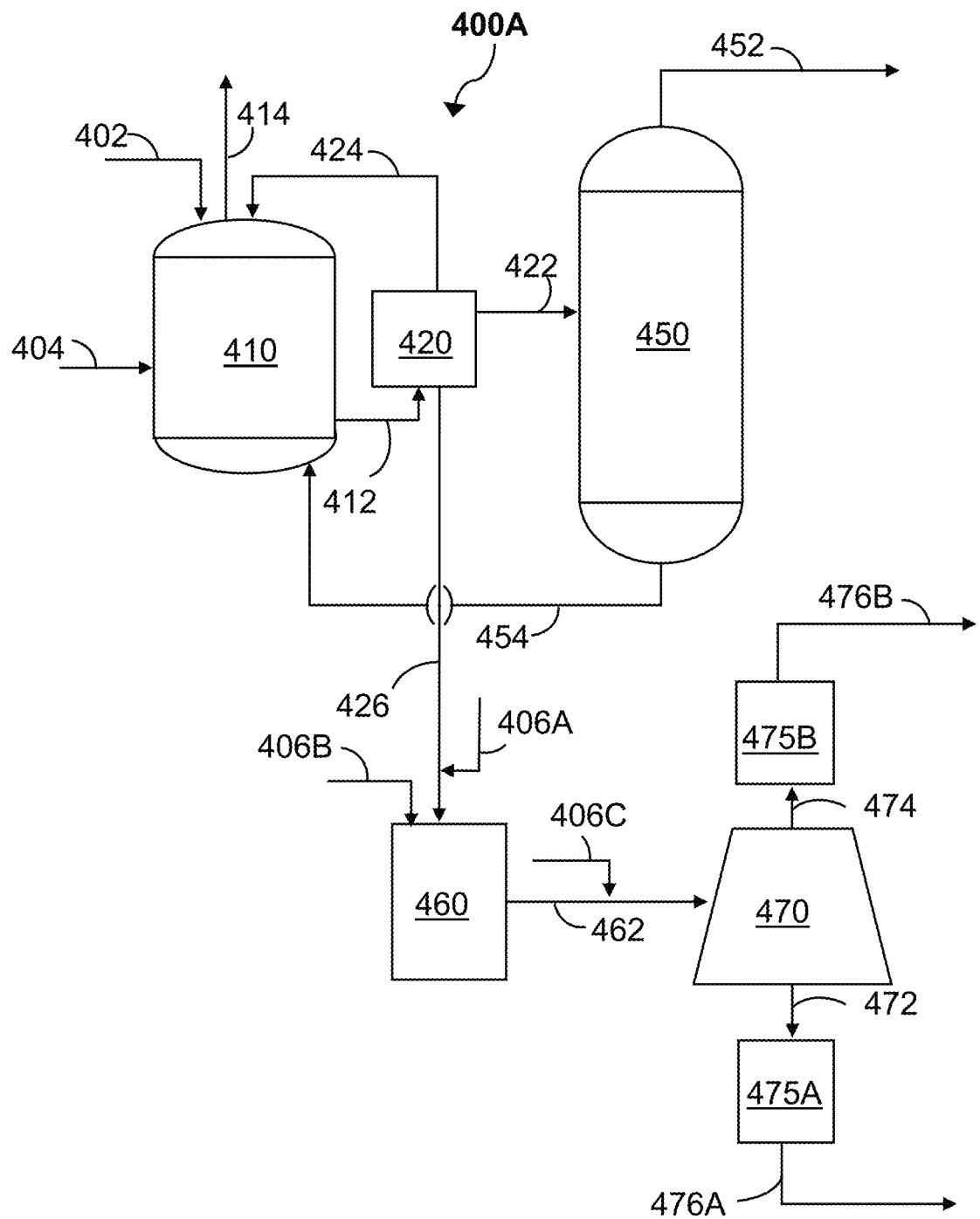
FIG. 4A shows a schematic of a bacterial fermentation system 400A with one or more cell separators, one or more processing chambers, one or more rupturing devices, one or more fractionators, one or more dehydration chambers and one or more inlet lines for delivering pH adjusting agents into the system for a fermentation process using a culture of an anaerobic bacteria according to one or more embodiments of the invention.

FIG. 4A shows a schematic of a bacterial fermentation system 400A with one or more inlet lines for delivering pH adjusting agents into the fermentation process, one fermentation vessel, one cell separator, one processing chamber, one rupturing device, one fractionator, and two dehydration chambers for a fermentation process using a culture of an anaerobic bacteria according to one or more embodiments of the invention and obtaining a protein-rich nutrient supplement from bacterial fermentation. The bacterial fermentation system 400A includes an inlet line 402, an inlet line 404, an inlet line 406A, an inlet line 406B, an inlet line 406C, a fermentation vessel 410, an outlet line 412, an outlet line 414, a cell separator 420, an outlet line 422, an outlet line 424, a processing chamber 450, an outlet line 452, an outlet line 454, a rupturing device 460, an outlet line 462, a fractionator 470 an outlet line 472, an outlet line 474, a dehydration chamber 475A, a dehydration chamber 475B, an outlet line 476A, and an outlet line 476B.

The bacterial fermentation system 400A can be, in one embodiment, a continuous bacterial fermentation system. First, a flow of fermentation medium is supplied to the bacterial fermentation system 400A by the inlet line 402. Next, a flow of gaseous substrates is supplied to the bacterial fermentation system 400A by the inlet line 404. The flow of gaseous substrates and the fermentation medium then enter into the fermentation vessel 410 that cultures anaerobic bacteria. The fermentation vessel 410 provides an environment to ferment the gaseous substrate with anaerobic bacteria. Conversion of the gaseous substrates and the fermentation medium takes place in the fermentation vessel 410. Inside the fermentation vessel 410, the gaseous substrates and the fermentation medium are fermented facilitated by the anaerobic bacteria contained within the fermentation vessel into a fermentation liquid broth, containing cells of the anaerobic bacteria at a first concentration. Unreacted reactant gases are then released and exhausted from the bacterial vessel 410 by the outlet line 414.

Further, the fermentation liquid broth is delivered and supplied to the cell separator 420 by outlet line 412. Inside the cell separator 420, the cells of the anaerobic bacteria contained within the fermentation liquid broth are separated into a cell-free permeate solution and a cell-containing anaerobic bacteria cells at a second concentration. The cell-free permeate solution in the cell separator 420 is then delivered to the processing chamber 450 via the outlet line 422. An amount of the cell-containing suspension, containing anaerobic bacteria cells, in the cell separator 420 is then delivered back to the fermentation vessel 410 via the outlet line 424 to undergo further fermentation process. Another amount of the cell-containing suspension, containing anaerobic bacteria cells, in the cell separator 420 is delivered via the outlet line 426 to the rupturing device 460.

In one embodiment, the fermentation system 400A further includes an inlet line 406A connected to the outlet line 426 for delivering pH-adjusting agents into the fermentation system and adjusting the pH value of the cell-containing suspension, containing anaerobic bacteria cells delivered out of the cell separator 420. Treating cells with pH-adjusting agents makes the cell membrane more malleable to mechanical disruption of the bacterial cells. This pH-adjusting can take place before the cell-containing suspension enters into the rupturing device 460. Alternatively, pH-adjusting can take place when the cell-containing suspension enters into the rupturing device 460. Alternatively, the pH-adjusting can take place after the cell-containing suspension is ruptured by the rupturing device 460 and a homogenate containing the anaerobic bacterial cells are treated with one or more pH-adjusting agents.

In one embodiment, the pH value of the cell-containing suspension can be adjusted to a value higher than the pH value of the fermentation broth liquid before the cell-containing suspension enters into the rupturing device 460. In one embodiment, the pH value of the cell-containing suspension can be adjusted to 5 before the cell-containing suspension enters into the rupturing device 460. In another embodiment, the pH value of the cell-containing suspension can be adjusted to 6 before the cell-containing suspension enters into the rupturing device 460. In another embodiment, the pH value of the cell-containing suspension can be adjusted to 7 before the cell-containing suspension enters into the rupturing device 460. In another embodiment, the pH value of the cell-containing suspension can be adjusted to 8 before the cell-containing suspension enters into the rupturing device 460. In another embodiment, the pH value of the cell-containing suspension can be adjusted to 9 before the cell-containing suspension enters into the rupturing device 460. In another embodiment, the pH value of the cell-containing suspension can be adjusted to 10 before the cell-containing suspension enters into the rupturing device 460. In another embodiment, the pH value of the cell-containing suspension can be adjusted to 11 before the cell-containing suspension enters into the rupturing device 460. In another embodiment, the pH value of the cell-containing suspension can be adjusted to 12 before the cell-containing suspension enters into the rupturing device 460. In another embodiment, the pH value of the cell-containing suspension can be adjusted to any value between 5 and 12 before the cell-containing suspension enters into the rupturing device 460.

Inside the processing chamber 450, the cell-free permeate solution is processed into an oxygenated hydrocarbonaceous compound. The processing chamber 450 also recycles water back to the fermentation vessel 410 via the outlet line 454. In total, the processing chamber 450 sends out 95% ethanol through the outlet line 452 for further downstream processing.

Inside the rupturing device 460, the cell membranes of the anaerobic bacterial cells contained within the cell-containing suspension are ruptured to generate a homogenate. The homogenate is sent to the fractionator 470 through the outlet line 462. In one aspect, the outlet line 474 is connected to the fractionator 470 that delivers a first protein-containing portion to be produced as the protein-rich nutrient supplement. The outlet line 472 is connected to the fractionator 470 that allows a cell debris portion to flow into another apparatus for further downstream processing. In another aspect, one or more of protein-containing fractions after one or more fractionators to remove unwanted contaminants and debris are added back together and produced as a protein-rich nutrient supplement.

Exemplary rupturing device that can be used herein includes, but is not limited to, a microfluidics device, a sonication device, an ultrasonic device, a mechanical disruption device, a French press, a freezer, a heater, a pasteurization device, a heat exchanger, a distillation column, a device that increases the temperature of process streams and holding tanks, an UV sterilization device, a gamma ray sterilization device, a reactor, a homogenizer, and combinations thereof.

One example of the rupturing device 460 is a device that causes an irreversible change to the structure of cell membranes and cell walls of bacterial microorganisms to allow further manipulation of the contents of the bacterial cells. Contents of the bacterial cells include nucleic acids, amino acids, proteins, glycogen, pigments, lipid droplets, crystals, and other nutrients, such as different forms of carbon, nitrogen, sulfur, calcium, etc.

In one aspect, the rupturing device 460 breaks open the cells by rupturing cell membranes of anaerobic bacterial cells by use of high force. High shearing forces are applied to the anaerobic bacterial cells within the cell-containing suspension, such as by sound, pressure, or mechanical means. In the present invention, the method includes sending to a rupturing device 460 a cell-containing suspension containing the anaerobic bacterial cells at a second concentration. The rupturing device 460 breaks open the cells by rupturing cell membranes of the cells with a strong force (e.g., mechanical, sound, pressure) and generates a homogenate, wherein there is better accessibility to useful moieties within the bacterial cells, e.g., protein, given the ruptured state of the bacterial cells. Alternatively, the method includes delivering the homogenate to a second rupturing device before the homogenate is delivered to a first fractionator. The second rupturing device further ruptures the cells of the homogenate, after which a protein-rich nutrient supplement is produced.

As an example, the rupturing device 460 is a microfluidics device. The microfluidics device includes, but is not limited to, reaction chambers, tubes, pumps, flanged pipes, rings, gaskets, high-pressure check valves. The reaction chamber of the microfluidics device can be a ceramic reaction chamber, an abrasion-resistant chamber, a spool reaction chamber, that is single-slotted, multi-slotted and has micro-channeling.

As another example, the rupturing device 460 is an enzymatic treatment device. As yet another example, the rupturing device is an ultrasonic device. The ultrasonic device is an ultrasonic probe or an ultrasonic bath. The ultrasonic device shears cells by use of high frequency sound waves to agitate and rupture cells. As yet another example, the rupturing device is a freezing device. The freezing device has a freeze and thaw cycle, wherein the bacterial cells enter multiple rounds of the freeze and thaw cycle, wherein the cells are frozen and then thawed in a buffer. As yet another example, the rupturing device is a mechanical rupturing device. The mechanical rupturing device includes mechanical blades or beads to break down cell walls and/or cell membranes of the bacterial cells.

In another alternative embodiment, the fermentation system 400A further includes an inlet line 406B connected to the rupturing device 460 for delivering pH-adjusting agents into the fermentation system and adjusting the pH value of the anaerobic bacteria cells within the rupturing device 460. In one embodiment, the pH value of the cell-containing suspension can be adjusted to a value higher than the pH value of the fermentation broth liquid before the cell-containing suspension enters into the rupturing device 460. In another embodiment, the pH value of the cell-containing suspension can be adjusted to any value between 5 and 12 within the rupturing device 460.

In another alternative embodiment, the fermentation system 400A further includes an inlet line 406C connected to the outlet line 462 for delivering pH-adjusting agents into the fermentation system and adjusting the pH value of the homogenate ruptured from the cell-containing solution containing the anaerobic bacterial cells. In another embodiment, the pH value of the homogenate after being ruptured from the cell-containing solution containing the anaerobic bacterial cells can be adjusted to a value higher than the pH value of the fermentation broth liquid before the homogenate enters into the fractionator 470. In another embodiment, the pH value of the homogenate after being ruptured from the cell-containing solution containing the anaerobic bacterial cells can be adjusted to 5 before the homogenate enters into the fractionator 470. In another embodiment, the pH value of the homogenate after being ruptured from the cell-containing solution containing the anaerobic bacterial cells can be adjusted to 6 before the homogenate enters into the fractionator 470. In another embodiment, the pH value of the homogenate after being ruptured from the cell-containing solution containing the anaerobic bacterial cells can be adjusted to 7 before the homogenate enters into the fractionator 470. In another embodiment, the pH value of the homogenate after being ruptured from the cell-containing solution containing the anaerobic bacterial cells can be adjusted to 8 before the homogenate enters into the fractionator 470. In another embodiment, the pH value of the homogenate after being ruptured from the cell-containing solution containing the anaerobic bacterial cells can be adjusted to 9 before the homogenate enters into the fractionator 470. In another embodiment, the pH value of the homogenate after being ruptured from the cell-containing solution containing the anaerobic bacterial cells can be adjusted to 10 before the homogenate enters into the fractionator 470. In another embodiment, the pH value of the homogenate after being ruptured from the cell-containing solution containing the anaerobic bacterial cells can be adjusted to 11 before the homogenate enters into the fractionator 470. In another embodiment, the pH value of the homogenate after being ruptured from the cell-containing solution containing the anaerobic bacterial cells can be adjusted to 12 before the homogenate enters into the fractionator 470. In another embodiment, the pH value of the homogenate after being ruptured from the cell-containing solution containing the anaerobic bacterial cells can be adjusted to any value between 5 and 12 before the homogenate enters into the fractionator 470.

The pH-adjusting agents which can be delivered into the system via inlet lines 406A, 406B, and 406C include sodium hydroxide, potassium hydroxide, ammonium hydroxide, bicarbonate, hydrochloric acid, nitric acid, phosphoric acid, hydrogen chloride and any agents that could be used to raise or lower the pH value of a solution.

Inside the fractionator 470, the homogenate is then fractionated into a first protein-containing portion and a protein-containing cell debris portion. Next, the first protein-containing cell debris portion is delivered to the dehydration chamber 475A via the outlet line 472. Then, the first protein-containing portion is delivered to the dehydration chamber 475B via the outlet line 474. Exemplary fractionators include, but are not limited to, various types of solid-liquid fractionators, centrifugation devices, continuous centrifuges, decanter centrifuges, disc-stack centrifuges, a filtration devices, a hollow fiber filtration device, a spiral wound filtration device, a ceramic filter device, a cross-flow filtration device, a size exclusion device, one or series of size exclusion columns, one or series ion exchange columns, one or series of carbon polymer columns, a flow-through magnetic fractionator, an ultrafiltration device, one or series of affinity chromatography columns, one or series of gel filtration columns, and combinations thereof.

After the dehydration process undergone in the dehydration chamber 475A and dehydration chamber 475B, a protein-rich nutrient supplement can be obtained and collected via both of the outlet lines 476A and 476B, each from the dehydration chamber 475A and the dehydration chamber 475B, respectively.

Figure 4B:
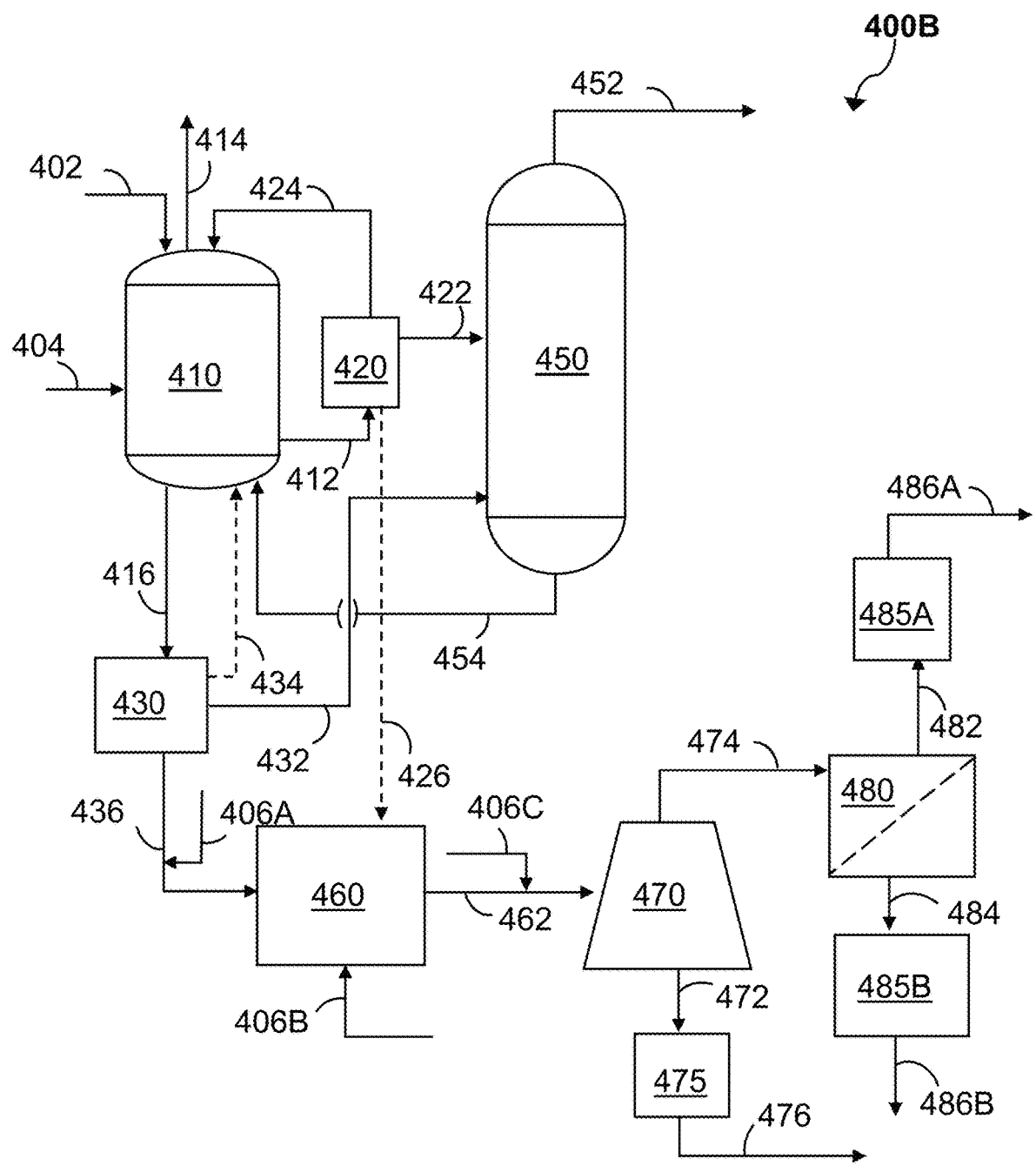
FIG. 4B shows a schematic of a bacterial fermentation system 400B with one or more inlet lines for delivering pH adjusting agents into the system, two cell separators, one processing chamber, one rupturing device, two fractionators and three dehydration chambers for a fermentation process using a culture of an anaerobic bacteria according to one or more embodiments of the invention.

FIG. 4B shows a schematic of a bacterial fermentation system 400B with one or more inlet lines for delivering pH-adjusting agents into the fermentation system, one fermentation vessel, two cell separators, one processing chamber, one rupturing device, two fractionators, and three dehydration chambers to obtain protein-rich nutrient supplements from a bacterial fermentation process. The bacterial fermentation system 400B includes the inlet line 402, the inlet line 404, an inlet line 406A, an inlet line 406B, an inlet line 406C, the fermentation vessel 410, the outlet line 412, the outlet line 414, an outlet line 416, a cell separator 420, the outlet line 422, the outlet line 424, the outlet line 426, a cell separator 430, an outlet line 432, an outlet line 434, an outlet line 436, the processing chamber 450, the outlet line 452, the outlet line 454, the rupturing device 460, the outlet line 462, a fractionator 470, the outlet line 472, the outlet line 474, the dehydration chamber 475, the outlet line 476, a fractionator 480, an outlet line 482, an outlet line 484, a dehydration chamber 485A, an outlet line 486A, a dehydration chamber 485B, and an outlet line 486B.

In one aspect, the cell separator 430 is a cell concentrator. For the present invention, the method includes collecting from the fermentation vessel an amount of a fermentation liquid broth containing the cells of the anaerobic bacteria at a first concentration. This collection is delivered through the outlet line 416 that connects the fermentation vessel 410 to the cell separator 430. In the cell separator 430, the fermentation liquid broth is separated into a cell-free permeate solution and a cell-containing suspension containing the anaerobic bacterial cells at a first concentration and concentrated to a second concentration (for example, with a high concentration of cells, higher than the first concentration of the fermentation liquid broth). The cell-free permeate solution is sent to the processing chamber 450 through the outlet line 432 that connects the processing chamber 450 and the cell separator 430. The cell-containing suspension containing the cells at the second concentration is sent to the rupturing device 460 through the outlet line 436 that connects the rupturing device 460 to the cell separator 430.

In one embodiment, the fermentation system 400B further includes an inlet line 406A connected to the outlet line 436 for delivering pH-adjusting agents into the fermentation system and adjusting the pH value of the cell-containing suspension, containing anaerobic bacteria cells delivered out of the cell separator 430. Treating cells with pH-adjusting agents makes the cell membrane more malleable to mechanical disruption of the bacterial cells. This pH-adjusting can take place before the cell-containing suspension enters the rupturing device 460. Alternatively, pH-adjusting can take place during when the cell-containing suspension enters the rupturing device 460. Alternatively, the pH-adjusting can take place after the cell-containing suspension is ruptured by the rupturing device 460 and a homogenate containing the anaerobic bacterial cells are treated with one or more pH-adjusting agents.

In one embodiment, the pH value of the cell-containing suspension can be adjusted to a value higher than the pH value of the fermentation broth liquid before the cell-containing suspension enters the rupturing device 460. In another embodiment, the pH value of the cell-containing suspension can be adjusted to a value, such as 5, 6, 7, 8, 9, 10, 11 and 12, before the cell-containing suspension enters the rupturing device 460. In another embodiment, the pH value of the cell-containing suspension can be adjusted to any value between 5 and 12 before the cell-containing suspension enters the rupturing device 460.

In another alternative embodiment, the fermentation system 400B further includes an inlet line 406B connected to the rupturing device 460 for delivering pH-adjusting agents into the fermentation system and adjusting the pH value of the anaerobic bacteria cells within the rupturing device 460. In one embodiment, the pH value of the cell-containing suspension can be adjusted to a value higher than the pH value of the fermentation broth liquid before the cell-containing suspension enters into the rupturing device 460. In another embodiment, the pH value of the cell-containing suspension can be adjusted to a value, such as 5, 6, 7, 8, 9, 10, 11 and 12, within the rupturing device 460. In another embodiment, the pH value of the cell-containing suspension can be adjusted to any value between 5 and 12 within the rupturing device 460.

In one aspect, after being processed by the rupturing device 460, the homogenate is delivered to the fractionator 470 to separate into a protein-containing portion and a cell debris portion. The fractionator 470 is connected to the rupturing device 460 via the outlet line 462. The fractionator 470 has at least two outlet lines, where the outlet line 472 is used to deliver the cell debris portion and the second outlet line 474 is used to deliver the protein-containing portion.

In another alternative embodiment, the fermentation system 400B further includes an inlet line 406C connected to the outlet line 462 for delivering pH-adjusting agents into the fermentation system and adjusting the pH value of the homogenate ruptured from the cell-containing solution containing the anaerobic bacterial cells. In one embodiment, the pH value of the homogenate can be adjusted to a value higher than the pH value of the fermentation broth liquid before the homogenate enters into the fractionator 470. In another embodiment, the pH value of the homogenate can be adjusted to a value, such as 5, 6, 7, 8, 9, 10, 11 and 12, before the homogenate enters into the fractionator 470. In another embodiment, the pH value of the homogenate after being ruptured from the cell-containing solution containing the anaerobic bacterial cells can be adjusted to any value between 5 and 12 before the homogenate enters into the fractionator 470.

The pH-adjusting agents which can be delivered into the system via inlet lines 406A, 406B, and 406C include sodium hydroxide, potassium hydroxide, ammonium hydroxide, bicarbonate, hydrochloric acid, nitric acid, phosphoric acid, hydrogen chloride and any agents that could be set to raise or lower the pH value of a solution.

In one aspect, the first protein-containing portion is delivered to a fractionator 480 to further separate out a second protein-containing portion from the first protein-containing portion. The fractionator 480 is connected to the fractionator 470 via an outlet 474. The fractionator 480 has at least two outlets, wherein from a first outlet 482 flows cell debris and from a second outlet 484 flows a second protein-containing portion. The method further includes collecting the second protein-containing portion from the second fractionator. In still another aspect, there are two or more fractionators. In yet another aspect, there is only one fractionator within the bacterial fermentation system used for the present invention, from which a first protein-containing portion is collected. Exemplary fractionators include, but are not limited to, various types of solid-liquid fractionators, centrifugation devices, continuous centrifuges, decanter centrifuges, disc-stack centrifuges, a filtration devices, a hollow fiber filtration device, a spiral wound filtration device, a ceramic filter device, a cross-flow filtration device, a size exclusion device, one or series of size exclusion columns, one or series ion exchange columns, one or series of carbon polymer columns, a flow-through magnetic fractionator, an ultrafiltration device, one or series of affinity chromatography columns, one or series of gel filtration columns, and combinations thereof.

Figure 4C:
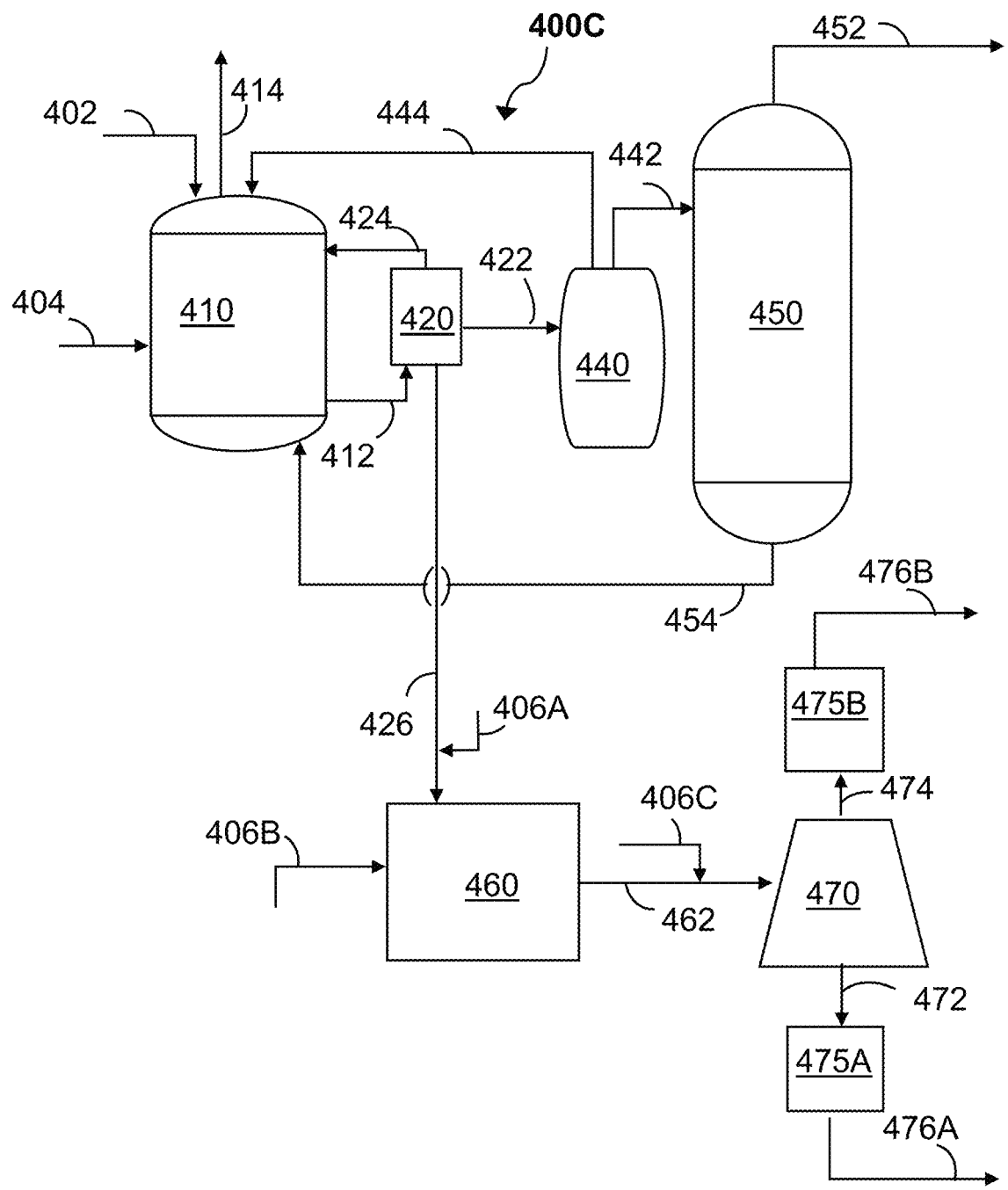
FIG. 4C shows a schematic of a bacterial fermentation system 400C with one or more inlet lines for delivering pH adjusting agents into the system, one cell separator, one cell-free holding tank, one processing chamber, one rupturing device, one fractionator, and two or more dehydration chambers for a fermentation process using a culture of an anaerobic bacteria according to one or more embodiments of the invention.

FIG. 4C shows a schematic of a bacterial fermentation system 400C with one or more inlet lines for delivering pH-adjusting agents into the fermentation system, one fermentation vessel, one cell separator, one cell-free holding tank, one processing chamber, one rupturing device, one fractionator, and two dehydration chambers to obtain protein-rich nutrient supplements from a bacterial fermentation process. The bacterial fermentation system 400C includes an inlet line 402, an inlet line 404, an inlet line 406A, an inlet line 406B, an inlet line 406C, a fermentation vessel 410, an outlet line 412, an outlet line 414, a cell separator 420, an outlet line 422, an outlet line 424, an outlet line 426, a cell-free holding tank 440, an outlet line 442, an outlet line 444, a processing chamber 450, an outlet line 452, an outlet line 454, a rupturing device 460, an outlet line 462, a fractionator 470, an outlet line 472, an outlet line 474, a dehydration chamber 475A, an outlet line 476A, a dehydration chamber 475B, and an outlet line 476B.

Figure 4D:
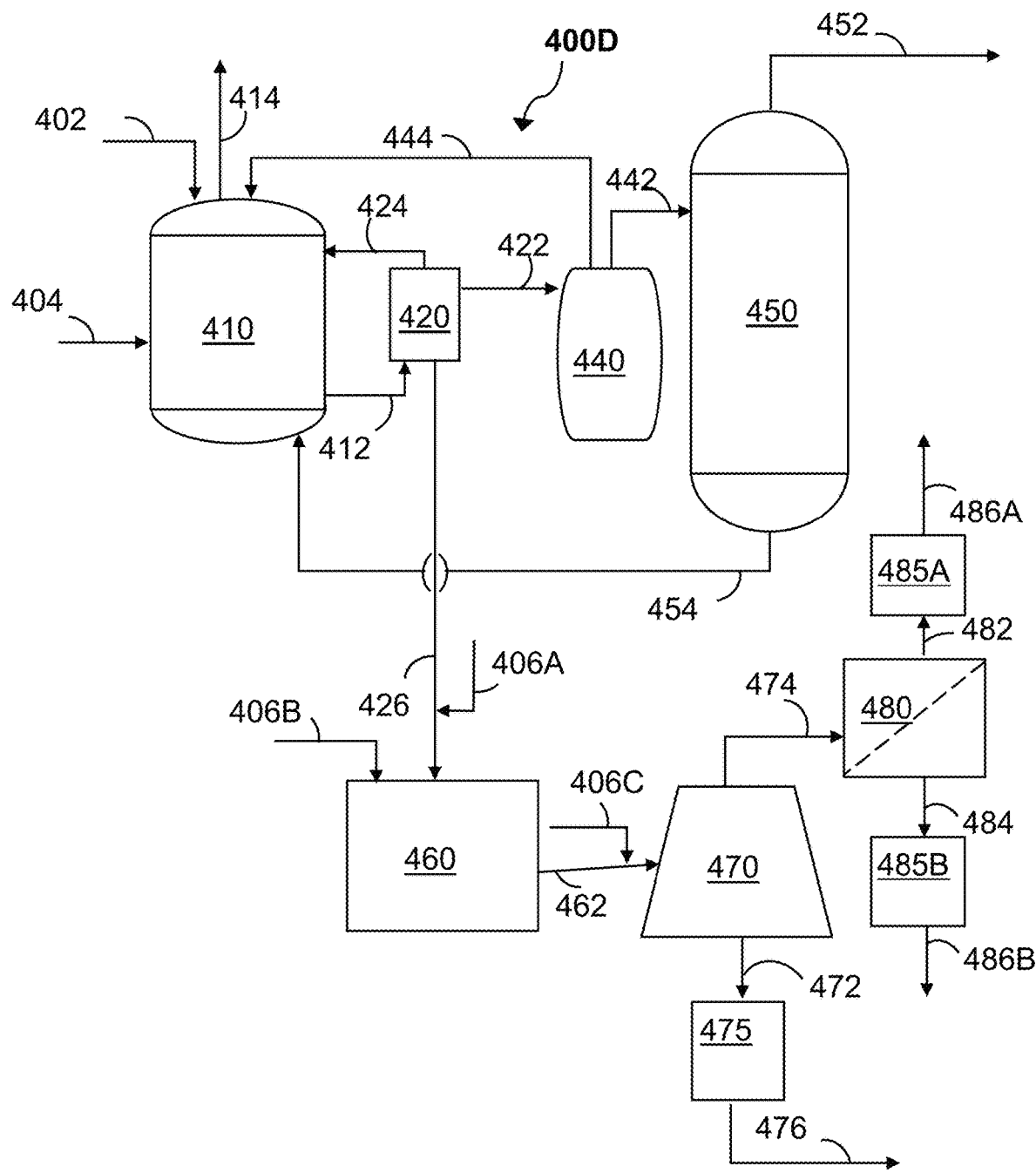
FIG. 4D shows a schematic of a bacterial fermentation system 400D with one or more inlet lines for delivering pH adjusting agents into the system, one cell separator, one cell-free holding tank, one processing chamber, one rupturing device, two fractionators, and optionally, additional dehydration chambers for a fermentation process using a culture of an anaerobic bacteria according to one or more embodiments of the invention.

FIG. 4D shows a schematic of a bacterial fermentation system 400D with one or more inlet lines for delivering pH-adjusting agents into the fermentation system, one fermentation vessel, one cell separator, one cell-free holding tank, one processing chamber, one rupturing device, two fractionators, and three dehydration chambers to obtain protein-rich nutrient supplements from a bacterial fermentation process. The bacterial fermentation system 400D includes an inlet line 402, an inlet line 404, an inlet line 406A, an inlet line 406B, an inlet line 406C, a fermentation vessel 410, an outlet line 412, an outlet line 414, a cell separator 420, an outlet line 422, an outlet line 424, an outlet line 426, a cell-free holding tank 440, an outlet line 442, an outlet line 444, a processing chamber 450, an outlet line 452, an outlet line 454, a rupturing device 460, an outlet line 462, a fractionator 470, an outlet line 472, an outlet line 474, a dehydration chamber 475, an outlet line 476, a fractionator 480, an outlet line 482, an outlet line 484, a dehydration chamber 485A, an outlet line 486A, a dehydration chamber 485B, and an outlet line 486B.

Figure 4E:
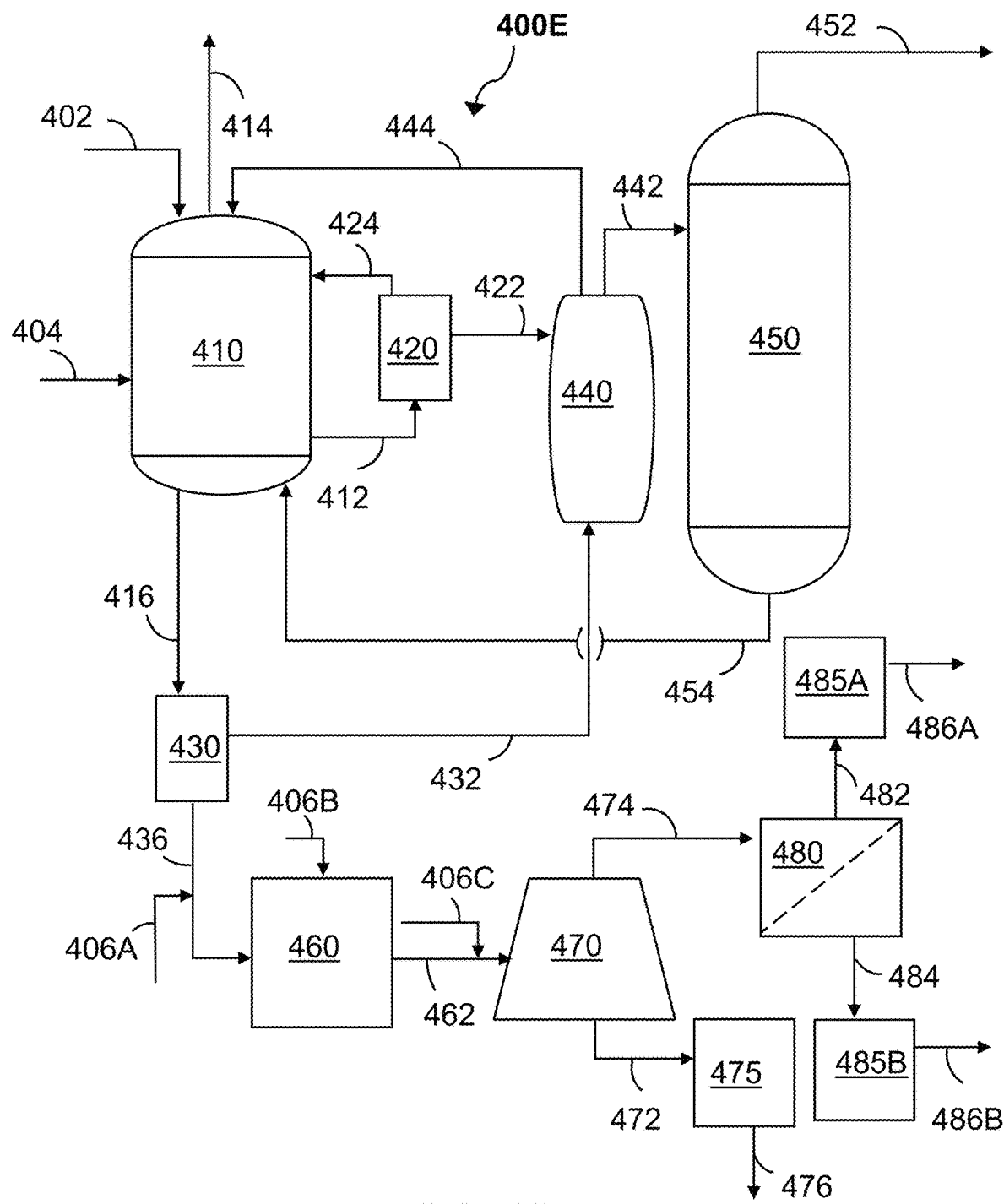
FIG. 4E shows a schematic of a bacterial fermentation system 400E with one or more inlet lines for delivering pH adjusting agents into the system, two cell separators, one cell-free holding tank, one processing chamber, one rupturing device, two fractionators, and optionally, three dehydration chambers for a fermentation process using a culture of an anaerobic bacteria according to one or more embodiments of the invention.

FIG. 4E shows a schematic of a bacterial fermentation system 400E with one or more inlet lines for delivering pH-adjusting agents into the fermentation system, one fermentation vessel, two cell separators, one cell-free holding tank, one processing chamber, one rupturing device, two fractionators, and three dehydration chambers to obtain protein-rich nutrient supplements from a bacterial fermentation process. The bacterial fermentation system 400E includes an inlet line 402, an inlet line 404, an inlet line 406A, an inlet line 406B, an inlet line 406C, a fermentation vessel 410, an outlet line 412, an outlet line 414, a cell separator 420, an outlet line 422, an outlet line 424, a cell separator 430, an outlet line 432, an outlet line 436, a cell-free holding tank 440, an outlet line 442, an outlet line 444, a processing chamber 450, an outlet line 452, an outlet line 454, a rupturing device 460, an outlet line 462, a fractionator 470, an outlet line 472, an outlet line 474, a dehydration chamber 475, an outlet line 476, a fractionator 480, an outlet line 482, an outlet line 484, a dehydration chamber 485A, an outlet line 486A, a dehydration chamber 485B, and an outlet line 486B.

Figure 4F:
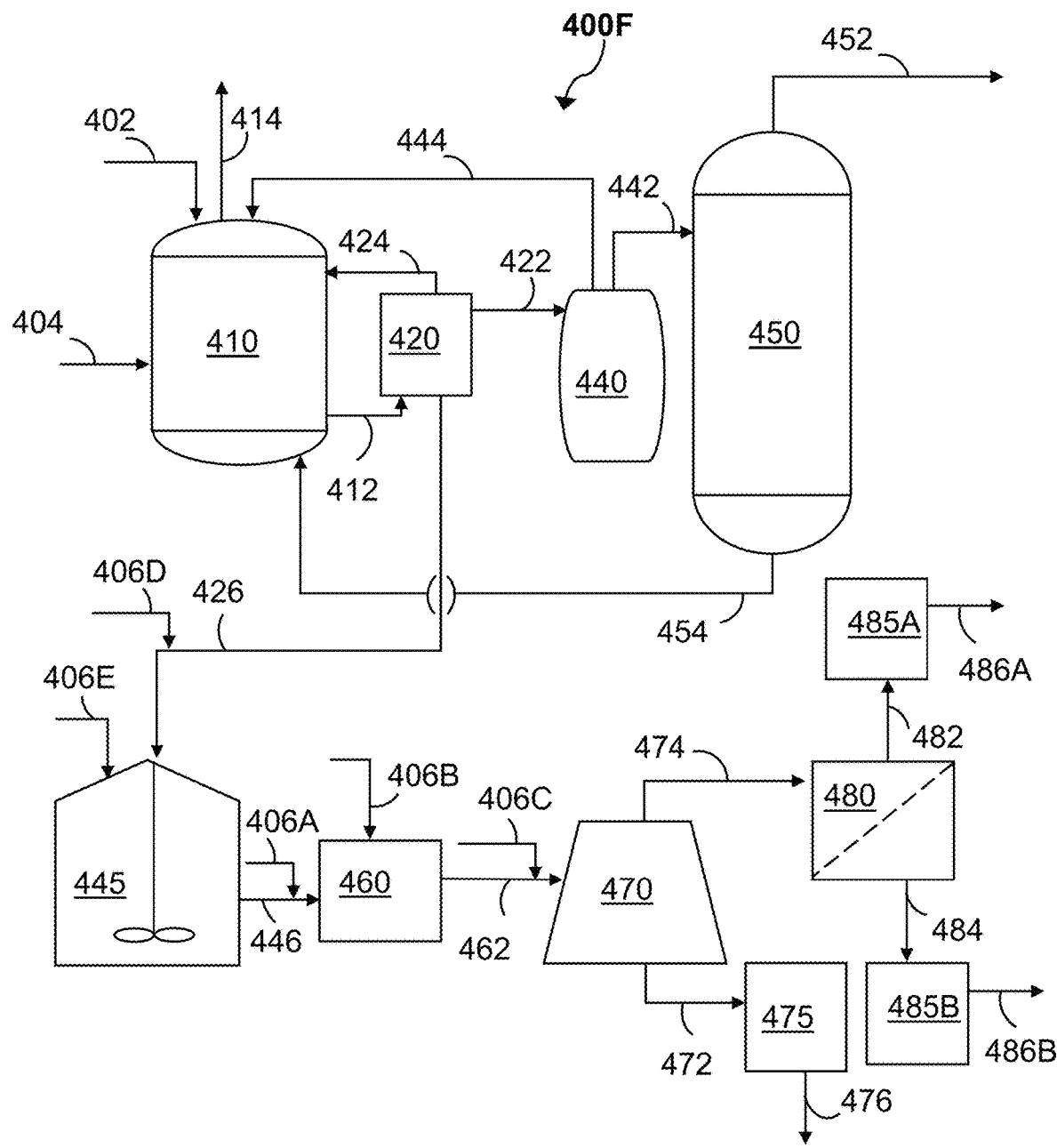
FIG. 4F shows a schematic of a bacterial fermentation system 400F with one or more inlet lines for delivering pH adjusting agents into the system, one cell separator, one cell-free holding tank, one processing chamber, one cell-containing holding tank, one rupturing device, two fractionators, and optionally, three dehydration chambers for a fermentation process using a culture of an anaerobic bacteria according to one or more embodiments of the invention.

FIG. 4F shows a schematic of a bacterial fermentation system 400F with one or more inlet lines for delivering pH-adjusting agents into the fermentation system, one fermentation vessel, one cell separator, one cell-free holding tank, one processing chamber, one cell-containing holding tank, one rupturing device, two fractionators, and three dehydration chambers to obtain protein-rich nutrient supplements from a bacterial fermentation process. The bacterial fermentation system 400F includes an inlet line 402, an inlet line 404, an inlet line 406A, an inlet line 406B, an inlet line 406C, an inlet line 406D, an inlet line 406E, a fermentation vessel 410, an outlet line 412, an outlet line 414, a cell separator 420, an outlet line 422, an outlet line 424, an outlet line 426, a cell-free holding tank 440, an outlet line 442, an outlet line 444, a cell-containing holding tank 445, an outlet line 446, a processing chamber 450, an outlet line 452, an outlet line 454, a rupturing device 460, an outlet line 462, a fractionator 470, an outlet line 472, an outlet line 474, a dehydration chamber 475, an outlet line 476, a fractionator 480, an outlet line 482, an outlet line 484, a dehydration chamber 485A, an outlet line 486A, a dehydration chamber 485B, and an outlet line 486B.

In one embodiment, the fermentation system 400F includes an inlet line 406D connected to the outlet line 426 for delivering pH-adjusting agents into the fermentation system and adjusting the pH value of the cell-containing suspension, containing anaerobic bacteria cells delivered out of the cell separator 420. Treating cells with pH-adjusting agents makes the cell membrane more malleable to mechanical disruption of the bacterial cells. This pH-adjusting can take place before the cell-containing suspension enters into the cell-containing holding tank 445. Alternatively, pH-adjusting can take place during when the cell-containing suspension enters into the cell-containing holding tank 445. Alternatively, this pH-adjusting can take place before the cell-containing suspension enters into the rupturing device 460, during when the cell-containing suspension enters into the rupturing device 460, or after the cell-containing suspension is ruptured by the rupturing device 460 and a homogenate containing the anaerobic bacterial cells are treated with one or more pH-adjusting agents.

In one embodiment, the pH value of the cell-containing suspension can be adjusted to a value higher than the pH value of the fermentation broth liquid before the cell-containing suspension enters into the cell-containing holding tank 445. In another embodiment, the pH value of the cell-containing suspension can be adjusted to a value, such as 5, 6, 7, 8, 9, 10, 11 and 12 before the cell-containing suspension enters into the rupturing device 460. In another embodiment, the pH value of the cell-containing suspension can be adjusted to any value between 5 and 12 before the cell-containing suspension enters into the rupturing device 460.

In one aspect, the bacterial fermentation system 400F includes a holding tank (e.g., the cell-containing holding tank 445) to house bacterial cells sent from the bacterial fermentation vessel. In one embodiment, the holding tank is a storage vessel that stores anaerobic bacterial cells of the microbial biomass collected from the fermentation vessel. This alleviates concerns over bottleneck issues when the bacterial cells are traveling from the fermentation vessel 410 into the rupturing device 460, with the bacterial cells being continuously collected from the bacterial fermentation vessel 410 and delivered to the rupturing device 460 without overloading the rupturing device 460. The delivery rate of the concentrated bacterial cells into the rupturing device 460 may be at a lower rate than the delivery rate of the fermentation liquid broth out of the cell separator/concentrator.

In another embodiment, the holding tank (e.g., the cell-containing holding tank 445) serves as a pretreatment device, where the bacterial cells are subjected to one or more additives to increase rupturing efficiency. Treating cells with additives makes the cell membrane more malleable to mechanical disruption of the bacterial cells. This pretreatment can take place before the cell-containing suspension enters the rupturing device 460. Alternatively, the pretreatment can take place after the cell-containing suspension is ruptured by the rupturing device 460 and a homogenate containing the anaerobic bacterial cells are treated with one or more additives. Examples of the cell-containing holding tank 445 include, but are not limited to, process chambers, tanks, stainless steel tanks, plastic tanks, etc.

In the bacterial fermentation system 400F, the cell-containing suspension containing the cells can pre-treated with one or more additives inside the cell-containing holding tank 445. The one or more additives may be added to the cell-containing holding tank 445 via the inlet line 406E, for example, surfactants, detergents, EDTA, Triton X-100, Tween-20, sodium dodecyl sulfate, CHAPS, enzymes, proteases, lysozyme, benzonase, nuclease, ribonucleases (RNases), deoxyribonucleases (DNases), hydrolysis-inducing agents, pH-adjusting agents, and a combination thereof. One example of an additive as a pH-adjusting agent is sodium hydroxide. Another example of an additive as a pH-adjusting agent is hydrogen chloride.

In one embodiment, the pH value of the cell-containing suspension can be adjusted to a value higher than the pH value of the fermentation broth liquid before the cell-containing suspension within the cell-containing holding tank 445. In another embodiment, the pH value of the cell-containing suspension can be adjusted to a value, such as 5, 6, 7, 8, 9, 10, 11 and 12, within the cell-containing holding tank 445. In another embodiment, the pH value of the cell-containing suspension can be adjusted to any value between 5 and 12 within the cell-containing holding tank 445.

The pH-adjusting agents which can be delivered into the system via inlet lines 406A, 406B, 406C, 406D, and 406E include sodium hydroxide, potassium hydroxide, ammonium hydroxide, bicarbonate, hydrochloric acid, nitric acid, phosphoric acid, hydrogen chloride and any agents that could be used to raise or lower the pH value of a solution.

In one aspect, the pretreatment device is connected to the cell separator/concentrator (e.g., the cell separator 420 and/or the cell separator 430), which is connected to the fermentation vessel 410. In another aspect, the pretreatment device is connected to the fermentation vessel 410 directly, wherein a component of the pretreatment device is a cell separator and concentrator. The pretreatment device includes a pretreatment chamber and inlets (e.g., the inlet line 406) to introduce specific additives to render the cell membranes of the bacterial cells more malleable to other rupturing techniques. The type of additive(s) used and the type of rupturing device used can be any number of combinations to increase the rupturing efficiency of the cells.

Figure 4G:
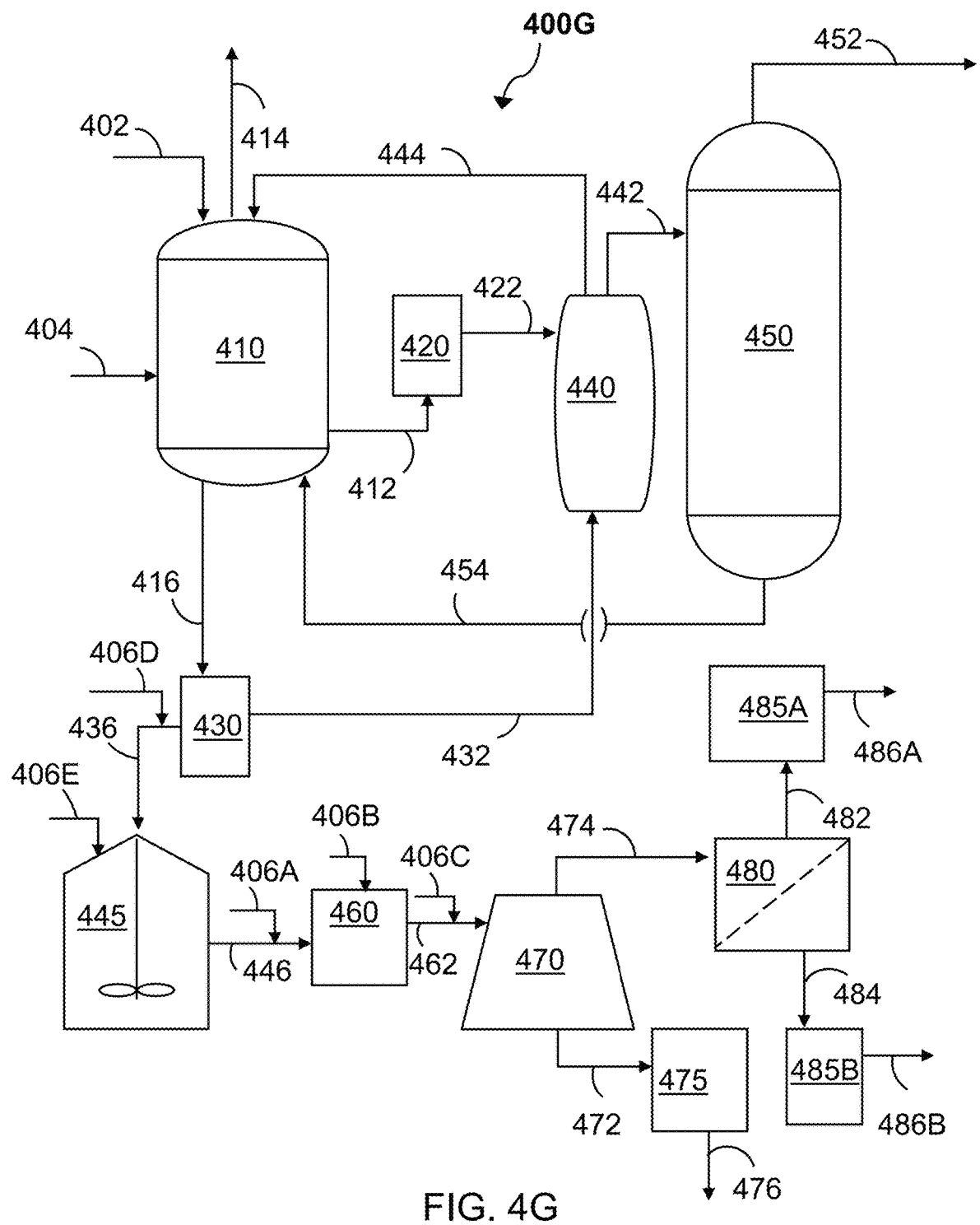
FIG. 4G shows a schematic of a bacterial fermentation system 400G with one or more inlet lines for delivering pH adjusting agents into the system, two cell separators, one cell-free holding tank, one processing chamber, one cell-containing holding tank, one rupturing device, two fractionators, and optionally, three dehydration chambers for a fermentation process using a culture of an anaerobic bacteria according to one or more embodiments of the invention.

FIG. 4G shows a schematic of a bacterial fermentation system 400G with one or more inlet lines for delivering pH-adjusting agents into the fermentation system, one fermentation vessel, two cell separators, one cell-free holding tank, one processing chamber, one cell-containing holding tank, one rupturing device, two fractionators, and three dehydration chambers to obtain protein-rich nutrient supplements from a bacterial fermentation process. The bacterial fermentation system 400G includes an inlet line 402, an inlet line 404, an inlet line 406A, an inlet line 406B, an inlet line 406C, an inlet line 406D, an inlet line 406E, a fermentation vessel 410, an outlet line 412, an outlet line 414, an outlet line 416, a cell separator 420, an outlet line 422, an outlet line 424, a cell separator 430, an outlet line 432, an outlet line 436, a cell-free holding tank 440, an outlet line 442, an outlet line 444, a cell-containing holding tank 445, an outlet line 446, a processing chamber 450, an outlet line 452, an outlet line 454, a rupturing device 460, an outlet line 462, a fractionator 470, an outlet line 472, an outlet line 474, a dehydration chamber 475, an outlet line 476, a fractionator 480, an outlet line 482, an outlet line 484, a dehydration chamber 485A, an outlet line 486A, a dehydration chamber 485B, and an outlet line 486B.

Figure 4H:
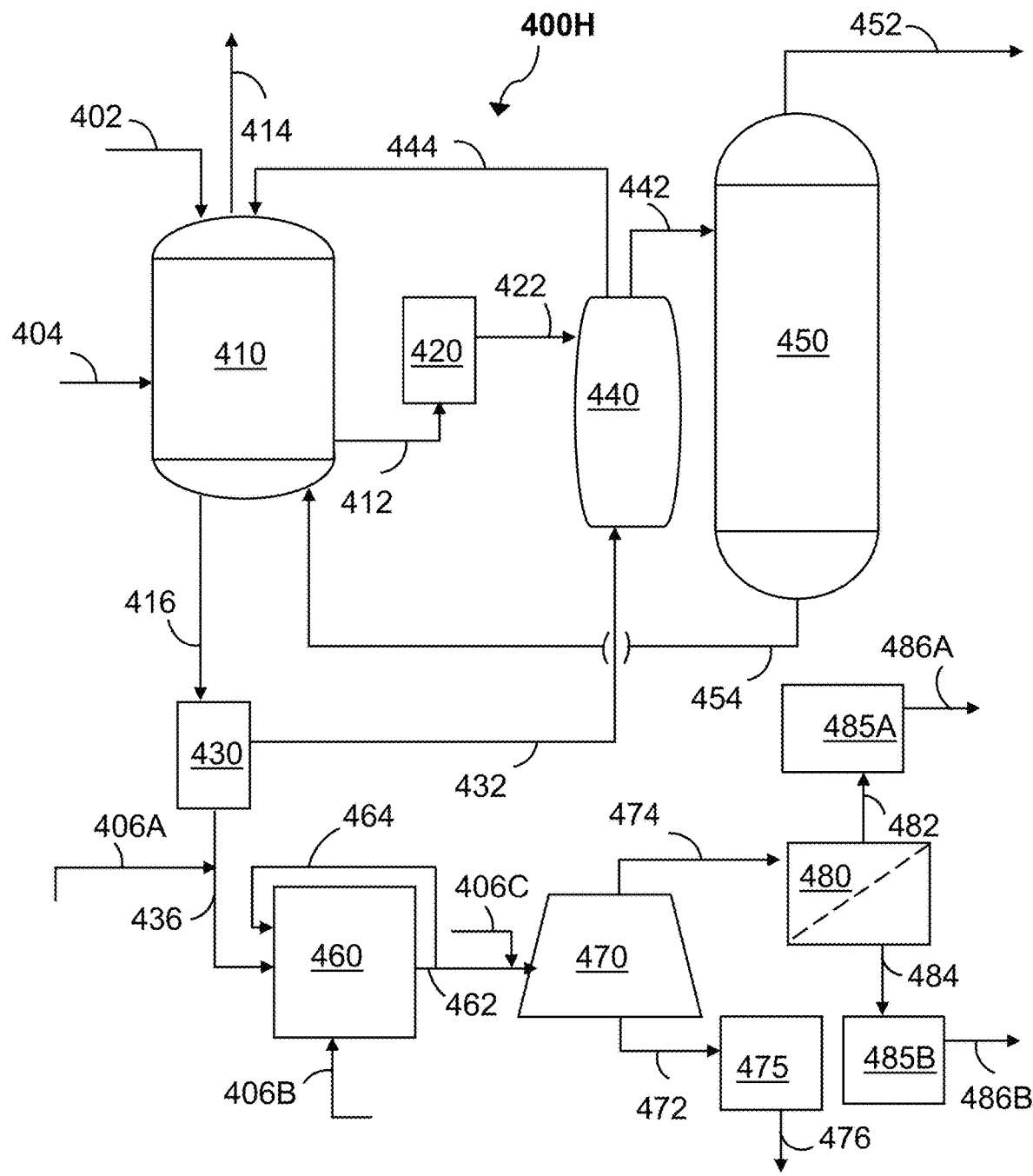
FIG. 4H shows a schematic of a bacterial fermentation system 400H with one or more inlet lines for delivering pH adjusting agents into the system, two cell separators, one cell-free holding tank, one processing chamber, one rupturing device, two fractionators, and optionally, three dehydration chambers for a fermentation process using a culture of an anaerobic bacteria according to one or more embodiments of the invention.

FIG. 4H shows a schematic of a bacterial fermentation system 400H with one or more inlet lines for delivering pH-adjusting agents into the fermentation system, one fermentation vessel, two cell separators, one cell-free holding tank, one processing chamber, one cell-containing holding tank, one rupturing device, two fractionators, and three dehydration chambers to obtain protein-rich nutrient supplements from a bacterial fermentation process. The bacterial fermentation system 400H includes an inlet line 402, an inlet line 404, an inlet line 406A, an inlet line 406B, an inlet line 406C, an inlet line 406D, an inlet line 406E, a fermentation vessel 410, an outlet line 412, an outlet line 414, an outlet line 416, a cell separator 420, an outlet line 422, an outlet line 424, a cell separator 430, an outlet line 432, an outlet line 436, a cell-free holding tank 440, an outlet line 442, an outlet line 444, a cell-containing holding tank 445, an outlet line 446, a processing chamber 450, an outlet line 452, an outlet line 454, a rupturing device 460, an outlet line 462, a return line 464, a fractionator 470, an outlet line 472, an outlet line 474, a dehydration chamber 475, an outlet line 476, a fractionator 480, an outlet line 482, an outlet line 484, a dehydration chamber 485A, an outlet line 486A, a dehydration chamber 485B, and an outlet line 486B.

In certain embodiments, the bacterial fermentation system 400H further includes one or more recycle lines. In one embodiment, the recycle line is a return line 464 connected to the rupturing device 460. The return line 464 takes a portion of the product mixtures from the rupturing device 460 and reenters into the rupturing device 460. This allows for multiple passes through the rupturing device 460, which, in turn, increases the ruptured amounts and protein concentrations of the protein-containing homogenate of anaerobic bacterial cell and ensures adequate accessibility to the protein compounds within the bacterial cells for further processing.

Figure 5A:
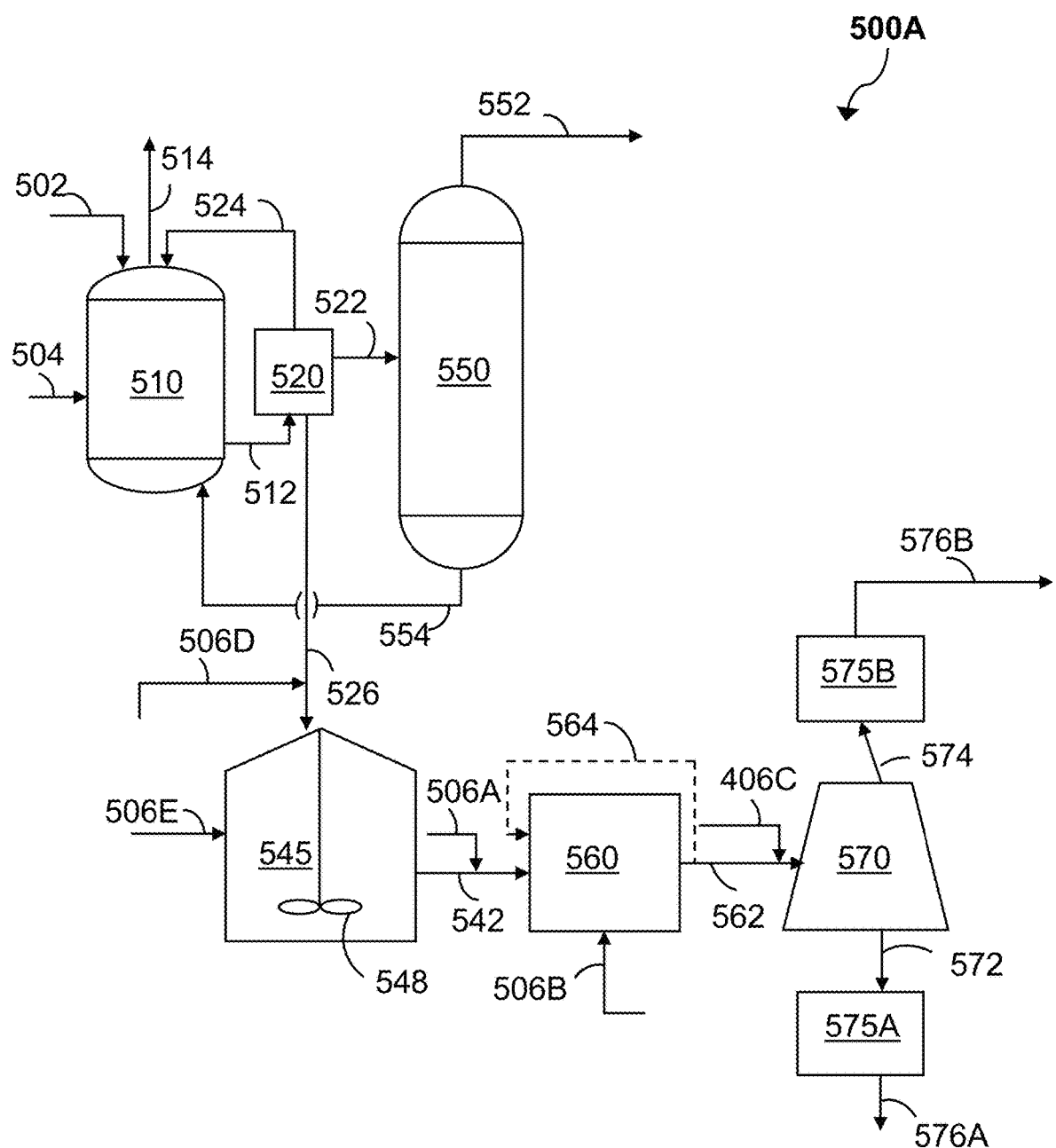
FIG. 5A is a schematic of an exemplary bacterial fermentation system for rupturing cells collected from an anaerobic bacterial fermentation process and obtaining one or more protein-containing portions from homogenates according to one or more embodiments of the invention.

FIG. 5A shows a schematic of a bacterial fermentation system 500A with one or more inlet lines for delivering pH-adjusting agents into the fermentation system, one fermentation vessel, one cell separator, one processing chamber, one cell-containing holding tank, one rupturing device, one fractionator, and two dehydration chambers to obtain protein-rich nutrient supplements from a bacterial fermentation process. The bacterial fermentation system 500A includes an inlet line 502, an inlet line 504, an inlet line 506A, an inlet line 506B, an inlet line 506C, an inlet line 506D, an inlet line 506E, a fermentation vessel 510, an outlet line 512, an outlet line 514, a cell separator 520, an outlet line 522, an outlet line 524, an outlet line 526, a processing chamber 550, an outlet line 552, an outlet line 554, a cell-containing holding tank 545, an inlet line 506, an outlet line 542, a mixer 548, a rupturing device 560, an outlet line 562, an outlet line 564, a fractionator 570, an outlet line 572, an outlet line 574, a dehydration chamber 575A, an outlet line 576A, a dehydration chamber 575B, and an outlet line 576B.

In the cell separator 520, the fermentation liquid broth from the fermentation vessel 510 is separated into a cell-free permeate solution and a cell-containing suspension containing the anaerobic bacterial cells at a second concentration. The cell-free permeate solution is sent to the processing chamber 550 through the outlet line 522 that connects the processing chamber 550 and the cell separator 520. The cell-containing suspension containing the anaerobic bacterial cells at a second concentration is sent to a cell-containing holding tank 545 through an outlet 526 that connects the cell-containing holding tank 545 to the cell separator 520.

The rupturing device 560 that delivers a homogenate is connected to a fractionator 570. In the fractionator 570, the method 500A includes separating the cell-containing suspension into a first protein-containing portion and a cell debris portion. The fractionator 570 is connected to the rupturing device 560 via an outlet 562. The fractionator 570 has at least two outlets, wherein from a first outlet 574 flows cell debris and from a second outlet 572 flows a first protein-containing portion. Types of fractionators used include, but are not limited to, various types of solid-liquid fractionators, centrifugation devices, continuous centrifuges, decanter centrifuges, disc-stack centrifuges, a filtration devices, a hollow fiber filtration device, a spiral wound filtration device, a ceramic filter device, a cross-flow filtration device, a size exclusion device, one or series of size exclusion columns, one or series ion exchange columns, one or series of carbon polymer columns, a flow-through magnetic fractionator, an ultrafiltration device, one or series of affinity chromatography columns, one or series of gel filtration columns, and combinations thereof.

In one example, the bacterial fermentation system 500A further includes the cell-containing holding tank 545 serving as a pretreatment chamber. The cell-containing suspension containing anaerobic bacterial cells is treated with one or more additives in the cell-containing holding tank 545. The cell-containing holding tank 545 is connected to the inlet line 506E that supplies one or more additives (e.g., detergents, enzymes, buffers, pH-adjusting agents etc.). The inlet 506E is generally turned off and can be turned on when needed. The cell-containing holding tank 545 holds the cell-containing suspension containing anaerobic bacterial cells until the cells reach high cell density (high concentrations) and can serve to provide timed deliveries of specific amounts of the cell-containing suspension to the rupturing device 560.

The mixer 548 inside the cell-containing holding tank 545 is an agitating device, such as an agitating device with propeller inside. The rupturing device 560 is connected to the cell-containing holding tank 545 via the outlet line 542. The rupturing device 560 generates a homogenate of the anaerobic bacterial cells. After a specific duration within the cell-containing holding tank 545, the cell-containing suspension is delivered to the rupturing device 560.

In one aspect, the fractionator 570 is connected to one or more dehydration chambers (e.g., the dehydration chambers 575A, 575B), which receive one or more protein-containing portions and dry them. Drying techniques used include drying, spray drying, lyophilizing, etc. The protein-containing portion is then further processed and blended into protein-rich nutrient supplements. The protein-containing portions may have a protein content of 10% or higher (such as between 10% and 80% or between 50% and 95%) of the protein-rich nutrient supplements.

In one embodiment, the fermentation system 500A includes an inlet line 506D connected to the outlet line 526 for delivering pH-adjusting agents into the fermentation system and adjusting the pH value of the cell-containing suspension, containing anaerobic bacteria cells delivered out of the cell separator 520. Treating cells with pH-adjusting agents makes the cell membrane more malleable to mechanical disruption of the bacterial cells. This pH-adjusting can take place before the cell-containing suspension enters into the cell-containing holding tank 545. Alternatively, pH-adjusting can take place during when the cell-containing suspension enters into the cell-containing holding tank 545 via inlet line 506E. Alternatively, this pH-adjusting can take place before the cell-containing suspension enters into the rupturing device 560 via inlet line 506A, during when the cell-containing suspension enters into the rupturing device 560 via inlet line 506B, or after the cell-containing suspension is ruptured by the rupturing device 560 via inlet line 506C and a homogenate containing the anaerobic bacterial cells are treated with one or more pH-adjusting agents.

The pH-adjusting agents which can be delivered into the system via inlet lines 506A, 506B, 506C, 506D and 506E include sodium hydroxide, potassium hydroxide, ammonium hydroxide, bicarbonate, hydrochloric acid, nitric acid, phosphoric acid, hydrogen chloride and any agents that could be used to raise or lower the pH value of a solution.

Figure 5B:
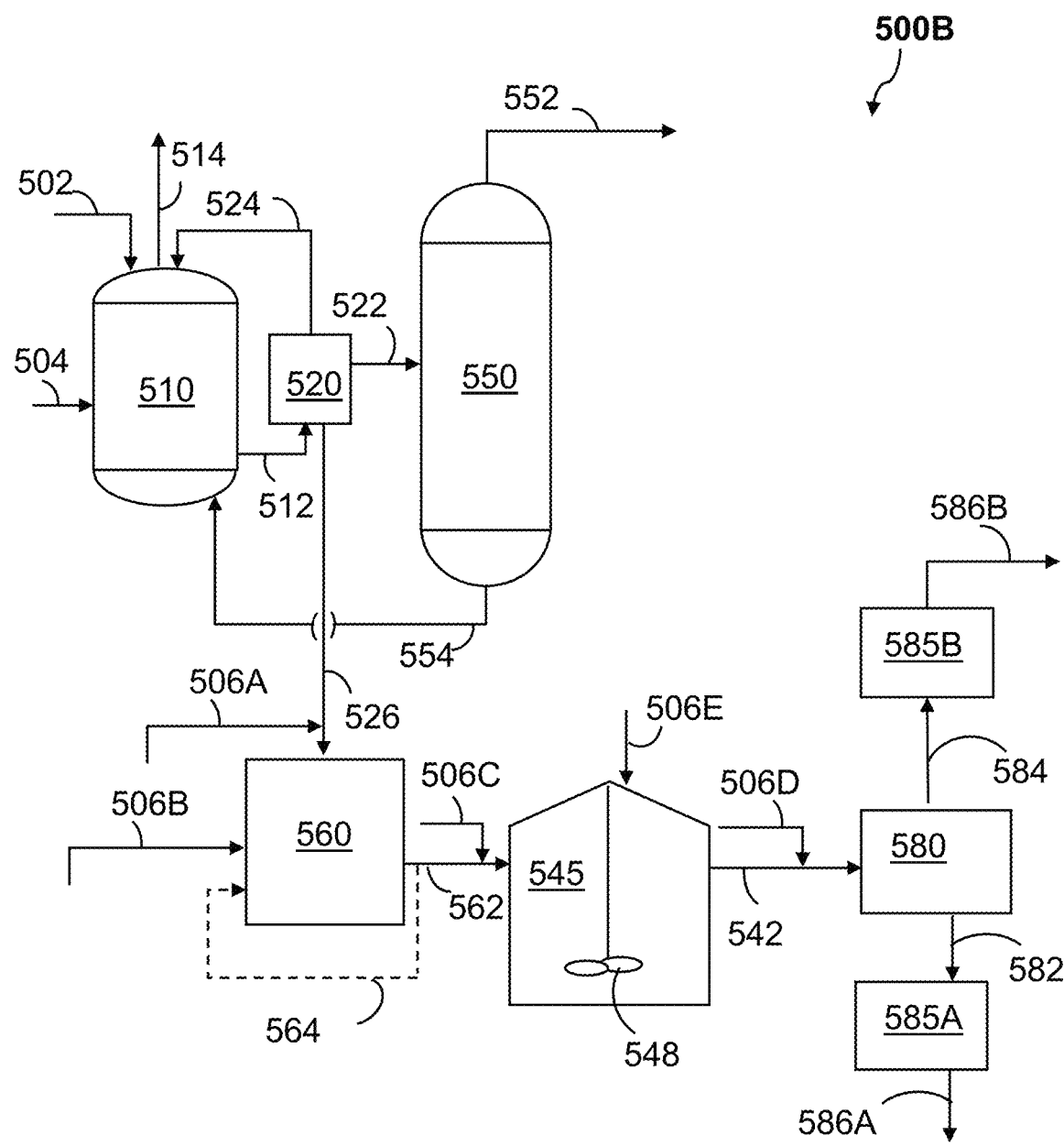
FIG. 5B is a schematic of another exemplary bacterial fermentation system for rupturing cells collected from an anaerobic bacterial fermentation process and obtaining one or more protein-containing portions from homogenates according to one or more embodiments of the invention.

FIG. 5B shows a schematic of a bacterial fermentation system 500B with one or more inlet lines for delivering pH-adjusting agents into the fermentation system, one fermentation vessel, one cell separator, one processing chamber, one rupturing device, one cell-containing holding tank, one fractionator, and two dehydration chambers to obtain protein-rich nutrient supplements from a bacterial fermentation process. The bacterial fermentation system 500B includes an inlet line 502, an inlet line 504, an inlet line 506A, an inlet line 506B, an inlet line 506C, an inlet line 506D, an inlet line 506E, a fermentation vessel 510, an outlet line 512, an outlet line 514, a cell separator 520, an outlet line 522, an outlet line 524, an outlet line 526, a processing chamber 550, an outlet line 552, an outlet line 554, a cell-containing holding tank 545, an inlet line 506, an outlet line 542, a mixer 548, a rupturing device 560, an outlet line 562, an outlet line 564, a fractionator 580, an outlet line 582, an outlet line 584, a dehydration chamber 585A, an outlet line 586A, a dehydration chamber 585B, and an outlet line 586B.

Figure 5C:
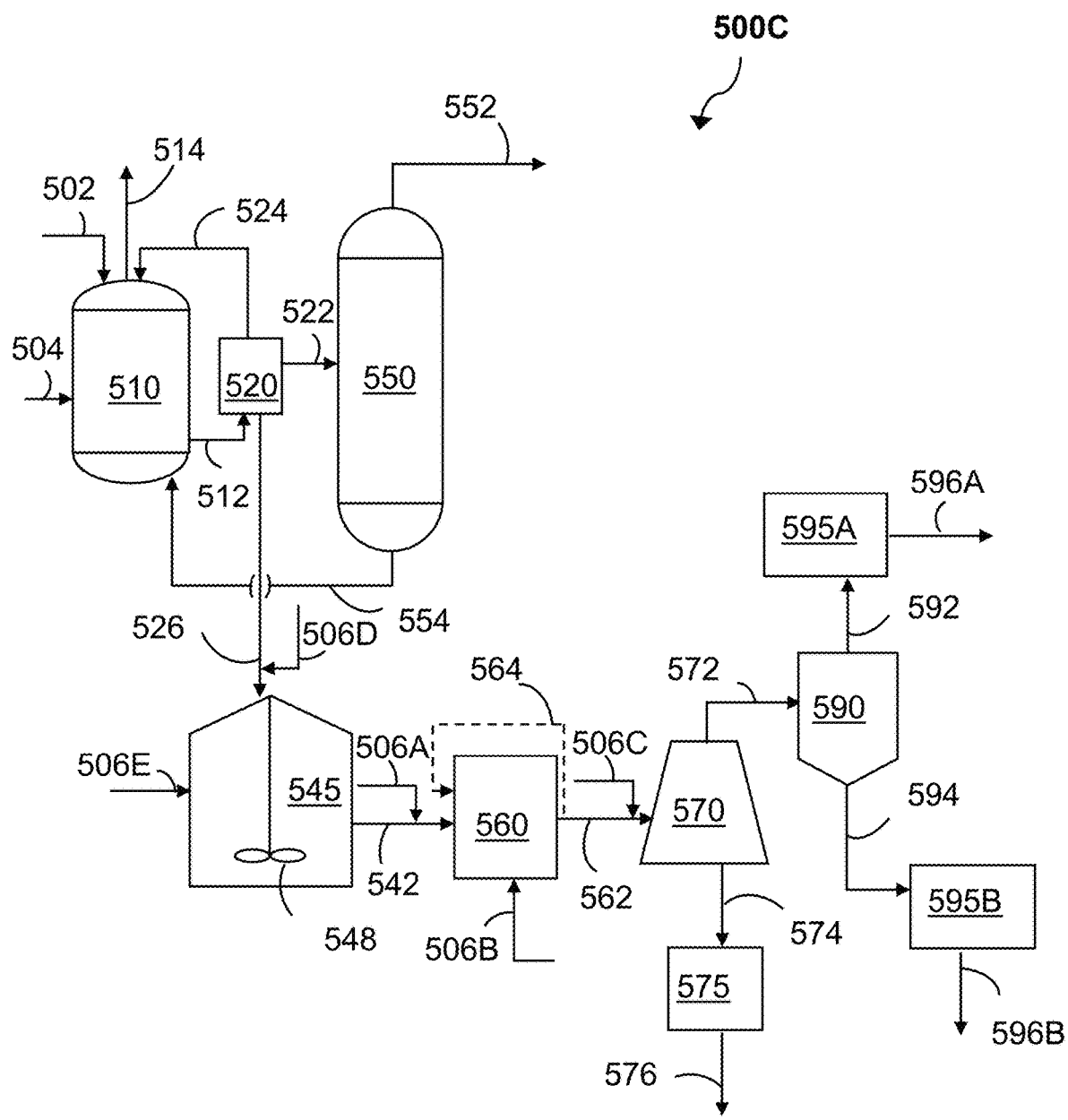
FIG. 5C is a schematic of another example of a bacterial fermentation system for rupturing cells collected from an anaerobic bacterial fermentation process and obtaining one or more protein-containing portions from homogenates according to one or more embodiments of the invention.

FIG. 5C shows a schematic of a bacterial fermentation system 500C with one or more inlet lines for delivering pH-adjusting agents into the fermentation system, one fermentation vessel, one cell separator, one processing chamber, one cell-containing holding tank, one rupturing device, two fractionators, and three dehydration chambers to obtain protein-rich nutrient supplements from a bacterial fermentation process. The bacterial fermentation system 500C includes an inlet line 502, an inlet line 504, an inlet line 506A, an inlet line 506B, an inlet line 506C, an inlet line 506D, an inlet line 506E, a fermentation vessel 510, an outlet line 512, an outlet line 514, a cell separator 520, an outlet line 522, an outlet line 524, an outlet line 526, a processing chamber 550, an outlet line 552, an outlet line 554, a cell-containing holding tank 545, an inlet line 506, a mixer 548, an outlet line 542, a rupturing device 560, an outlet line 562, an outlet line 564, a fractionator 570, the outlet line 572, the outlet line 574, the dehydration chamber 575, the outlet line 576, a fractionator 590, an outlet line 592, an outlet line 594, a dehydration chamber 595A, an outlet line 596A, a dehydration chamber 595B, and an outlet line 596B.

Figure 5D:
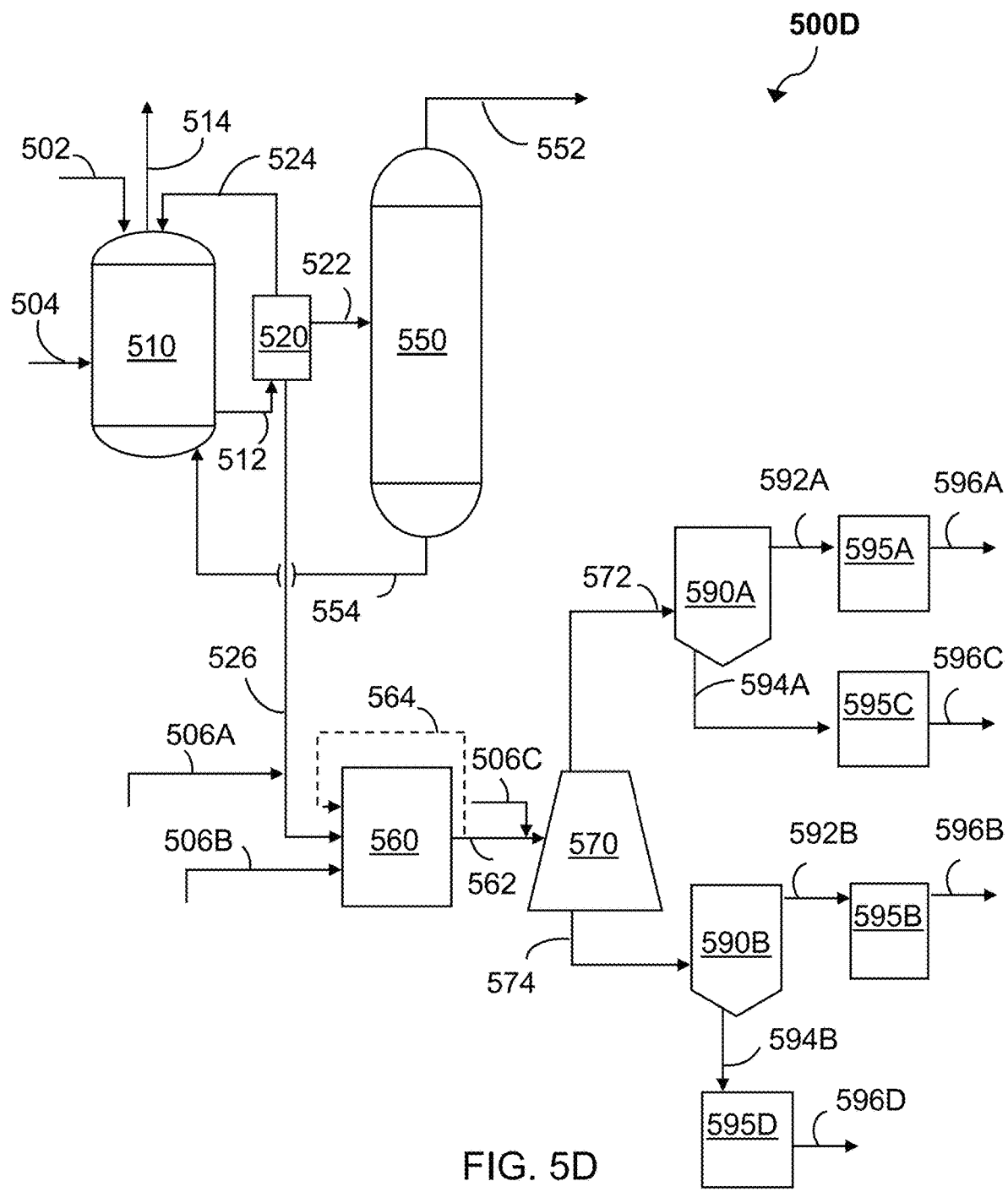
FIG. 5D is a schematic of yet another example of a bacterial fermentation system for rupturing cells collected from an anaerobic bacterial fermentation process and obtaining one or more protein-containing portions from homogenates according to one or more embodiments of the invention.

FIG. 5D shows a schematic of a bacterial fermentation system 500D with one or more inlet lines for delivering pH-adjusting agents into the fermentation system, one fermentation vessel, one cell separator, one processing chamber, one rupturing device, two fractionators, and four dehydration chambers to obtain protein-rich nutrient supplements from a bacterial fermentation process. The bacterial fermentation system 500D includes the inlet line 502, the inlet line 504, an inlet line 506A, an inlet line 506B, an inlet line 506C, a fermentation vessel 510, an outlet line 512, an outlet line 514, a cell separator 520, an outlet line 522, an outlet line 524, an outlet line 526, an processing chamber 550, an outlet line 552, an outlet line 554, a rupturing device 560, the outlet line 562, an outlet line 564, a fractionator 570, an outlet line 572, an outlet line 574, a fractionator 570, an outlet line 592A, an outlet line 594A, a fractionator 590, an outlet line 592B, an outlet line 594B, a dehydration chamber 595A, an outlet line 596A, a dehydration chamber 595B, an outlet line 596B, a dehydration chamber 595C, an outlet line 596C, a dehydration chamber 595D, and an outlet line 596D. In one aspect, the rupturing device 560 has a recycle stream line (e.g., the outlet line 564) that allows for multiple passes through the rupturing device 560.

Figure 5E:
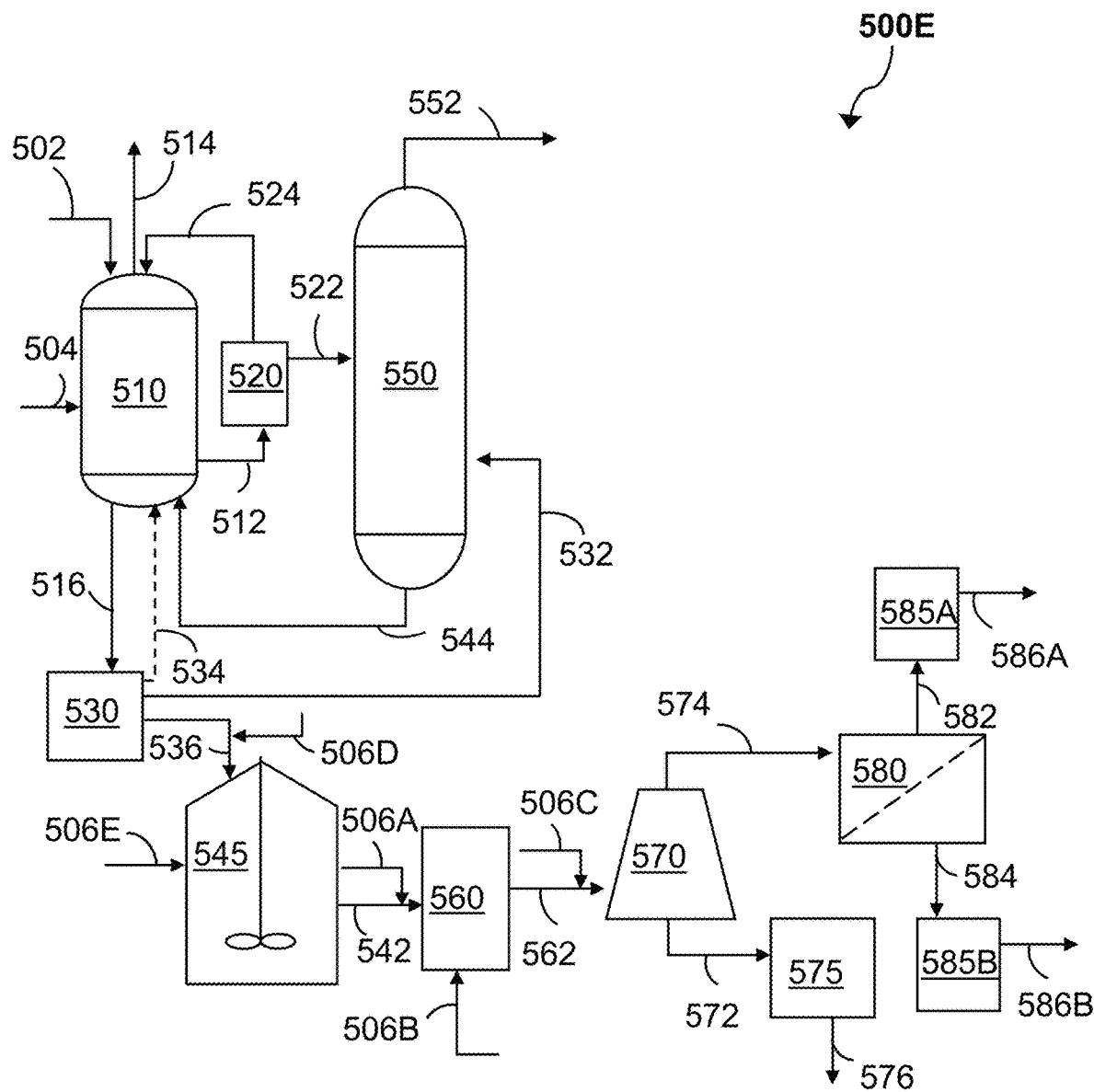
FIG. 5E is a schematic of another exemplary bacterial fermentation system for rupturing cells collected from an anaerobic bacterial fermentation process and obtaining one or more protein-containing portions from homogenates according to one or more embodiments of the invention.

FIG. 5E shows a schematic of a bacterial fermentation system 500E with one or more inlet lines for delivering pH-adjusting agents into the fermentation system, one fermentation vessel, two cell separators, one processing chamber, one cell-containing holding tank, one rupturing device, two fractionators, and three dehydration chambers to obtain protein-rich nutrient supplements from a bacterial fermentation process. The bacterial fermentation system 500E includes an inlet line 502, an inlet line 504, an inlet line 506A, an inlet line 506B, an inlet line 506C, an inlet line 506D, an inlet line 506E, a fermentation vessel 510, an outlet line 512, an outlet line 514, an outlet line 516, a cell separator 520, an outlet line 522, an outlet line 524, a processing chamber 550, an outlet line 552, an outlet line 544, a cell separator 530, an outlet line 532, an outlet line 534, an outlet line 536, a cell-containing holding tank 545, an inlet line 506, an outlet line 542, a mixer 548, a rupturing device 560, an outlet line 562, a fractionator 570, an outlet line 572, an outlet line 574, a dehydration chamber 575, the outlet line 576, a fractionator 580, an outlet line 582, an outlet line 584, a dehydration chamber 585A, an outlet line 586A, a dehydration chamber 585B, and an outlet line 586B.

Figure 6:
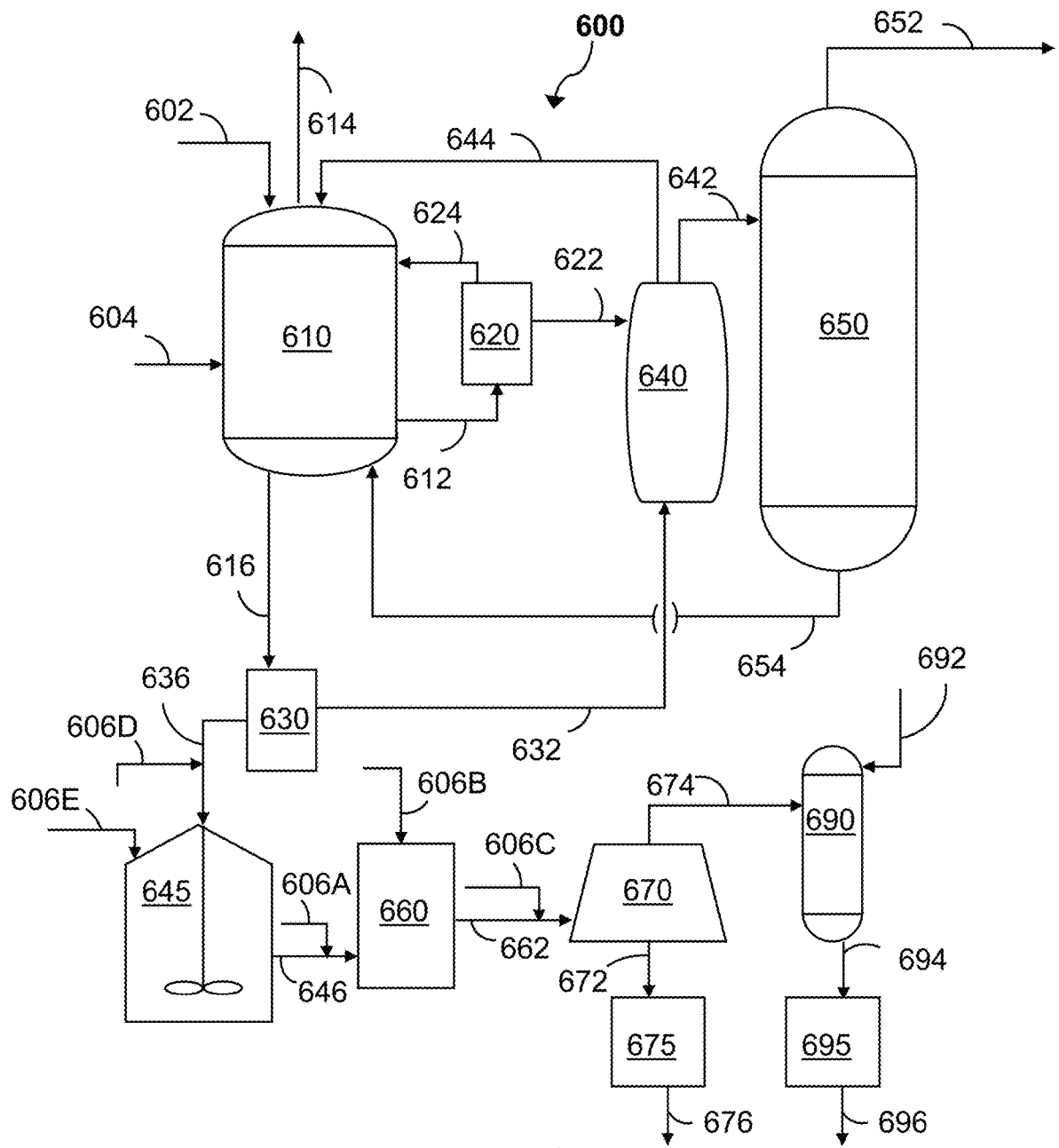
FIG. 6 is a schematic of still another example of a bacterial fermentation system for rupturing cells collected from an anaerobic bacterial fermentation process and obtaining one or more protein-containing portions from homogenates according to one or more embodiments of the invention.

FIG. 6 shows a schematic of a bacterial fermentation system 600 with one or more inlet lines for delivering pH-adjusting agents into the fermentation system, one fermentation vessel, two cell separators, one cell-free holding tank, one processing chamber, one cell-containing holding tank, one rupturing device, two fractionators, and two dehydration chambers to obtain protein-rich nutrient supplements from a bacterial fermentation process. The bacterial fermentation system 600 includes an inlet line 602, an inlet line 604, an inlet line 606A, an inlet line 606B, an inlet line 606C, an inlet line 606D, an inlet line 606E, a fermentation vessel 610, an outlet line 612, an outlet line 614, an outlet line 616, a cell separator 620, an outlet line 622, an outlet line 624, a cell-free holding tank 640, an outlet line 642, an outlet line 644, a processing chamber 650, an outlet line 652, an outlet line 654, a cell separator 630, an outlet line 632, an outlet line 636, a cell-containing holding tank 645, an inlet line 606, an outlet line 646, a rupturing device 660, an outlet line 662, a fractionator 670, an outlet line 672, an outlet line 674, a dehydration chamber 675, an outlet line 676, a fractionator 690, an inlet line 692, an outlet line 694, a dehydration chamber 695, and an outlet line 696.

In one embodiment, the fermentation system 600 includes an inlet line 606D connected to the outlet line 636 for delivering pH-adjusting agents into the fermentation system and adjusting the pH value of the cell-containing suspension, containing anaerobic bacteria cells delivered out of the cell separator 620. Treating cells with pH-adjusting agents makes the cell membrane more malleable to mechanical disruption of the bacterial cells. This pH-adjusting can take place before the cell-containing suspension enters into the cell-containing holding tank 645. Alternatively, pH-adjusting can take place during when the cell-containing suspension enters into the cell-containing holding tank 645 via inlet line 606E. Alternatively, this pH-adjusting can take place before the cell-containing suspension enters into the rupturing device 660 via inlet line 606A, during when the cell-containing suspension enters into the rupturing device 660 via inlet line 606B, or after the cell-containing suspension is ruptured by the rupturing device 660 via inlet line 606C and a homogenate containing the anaerobic bacterial cells are treated with one or more pH-adjusting agents.

The pH-adjusting agents which can be delivered into the system via the inlet lines 606A, 606B, 606C, 606D, and 606E include sodium hydroxide, potassium hydroxide, ammonium hydroxide, bicarbonate, hydrochloric acid, nitric acid, phosphoric acid, hydrogen chloride and any agents that could be used to raise or lower the pH value of a solution.

In one embodiment, there is one rupturing device that is a microfluidics device, wherein the cells enter the rupturing device and are subjected to high shearing forces in a reaction chamber to break apart the cell walls and cell membranes of the anaerobic bacteria. The ruptured bacterial cells are then further processed via centrifugation, filtration, various methods of dehydrating the anaerobic bacterial cells (e.g., drying, freeze drying, lyophilizing, etc.), blending, the removal of heavy metal ions, incorporation as a nutrient supplement into an ingestible substance, or combinations thereof.

In another embodiment, the bacterial fermentation system has two or more rupturing devices. The first rupturing device also can be a holding tank or a storage vessel that is holding the bacterial cells within a cell-containing suspension that has been separated from the fermentation liquid. There is a first rupturing device that is a pretreatment device, wherein a cell-containing suspension enters the first rupturing device and is treated with additives to increase rupturing efficiency. Additives used include, but are not limited to, one or more detergents, enzymes, chemicals, or combinations thereof. There is a second rupturing device that is a microfluidics device, wherein the cells enter the second rupturing device and is subjected to high shearing forces in a reaction chamber. The cell-containing suspension is forced through micro-channeling that causes the cell walls and cell membranes of bacterial cells to rupture and break open, wherein contents of the bacterial cells become free-floating throughout the fermentation liquid. This permits collection of a first protein recovery, which can be further manipulated by centrifugation, filtration, dehydration, etc.

III. Composition of Nutrient Supplements Comprising Fermentation-Derived Proteins One or more protein-containing portions recovered from the bacterial fermentation system described herein may be subject to direct blending with a feedstock composition, drying, settling, filtration, ultrafiltration, microfiltration, vacuum filtration, centrifugation, sequential centrifugation, freeze drying, freezing, hydrolysis, and combinations thereof to generate and obtain much pure forms of proteins and at higher protein concentrations. In the aspect where the microbial biomass is hydrolyzed, hydrolysis may be carried out via heat treatment, acid hydrolysis, enzyme hydrolysis, alkaline hydrolysis, and combinations thereof.

In one embodiment of the method, the first protein-containing portion is produced as the protein-rich nutrient supplement. The first protein-containing portion has a protein content that is between 60% to 80%. In another aspect, the first protein-containing portion has a protein content that is between 40% to 60%. In yet another aspect, the first protein-containing portion has a protein content that is between 10% to 40%.

In one embodiment, the present invention provides a composition that is a protein-rich nutrient supplement. This composition is generated from a fermentation process using acetogenic bacterial culture. This composition comprises a protein-containing portion separated from a cell debris portion of a homogenate, wherein the homogenate is obtained from rupturing a cell-containing suspension containing cells of the acetogenic bacterial culture, and wherein the cell-containing suspension is obtained from a fermentation liquid being delivered out of a fermentation vessel during fermentation of a gaseous substrate using the acetogenic bacterial culture.

In one aspect, the acetogenic bacterial culture is selected from a group consisting of *Clostridium* bacteria, *Acetobacterium* bacteria, and combinations thereof. The gaseous substrate fermented comprises one or more gases selected from the group consisting of carbon source substrates, carbon monoxide (CO), carbon dioxide ($CO_2$), hydrogen ($H_2$) gas, syngas, and combinations thereof.

In another aspect, the protein-containing portion of the composition comprises a protein content of between about 10% to about 80% of the composition, a carbohydrate content of between about 5% to about 35% of the composition, and a nucleic acid content of between about 5% to about 15% of the composition. The protein content in the protein-containing portion is greater than a carbohydrate content in the protein-containing portion. In yet another aspect, the nucleic acid content is no more than 2% of the composition. This is a composition ingestible for humans and animals alike.

In another embodiment, the composition of a protein-rich nutrient supplement comprises a purified protein product separated from a first amount from a protein-containing portion and a second amount from a cell debris portion of a homogenate, wherein the homogenate is obtained from rupturing a cell-containing suspension containing cells of the acetogenic bacterial culture, and wherein the cell-containing suspension is obtained from a fermentation liquid being delivered out of a fermentation vessel during fermentation of a gaseous substrate using the acetogenic bacterial culture. The cell debris portion comprises cell wall particulates, cell membrane particulates, protein aggregates, inclusion bodies, nucleic acid, and other components of an anaerobic bacterial cell. The fermentation liquid broth delivered out of the fermentation vessel is separated into a cell-free permeate solution and the cell-containing suspension containing the cells of the acetogenic bacterial culture. In one aspect, the partially purified protein product has a nucleic acid content that is no more than 2%. In another aspect, the nucleic acid content is no more than 8% to 12%.

In one aspect, the composition includes a protein content of between about 10% to about 80% of the composition, a carbohydrate content of between about 5% to about 35% of the composition, and a nucleic acid content of between about 5% to about 15% of the composition. The protein content in the protein-containing portion is greater than a carbohydrate content in the protein-containing portion.

In another aspect, the composition includes a protein content of between about 10% to about 80% of the composition, a carbohydrate content of between about 5% to about 35% of the composition, and a nucleic acid content of no more than 2% of the composition.

In yet another embodiment, the feedstock composition when removed from the bacterial fermentation vessel provides about 220 kcal or more per 100 grams of acetogenic biomass and may include about 15 grams or more carbohydrate per 100 grams of acetogenic biomass, on a dry weight basis. In this aspect, the feedstock has a weight ratio of carbohydrates to protein of about 1.0 or less. In another aspect, the feedstock includes about 18 mg or more calcium per 100 grams of acetogenic biomass, about 150 mg or more iron per 100 grams of cell mass, about 25 mg or more sodium per 100 grams of acetogenic biomass, about 1200 mg or more potassium per 100 grams of biomass, or a combination thereof, on a dry weight basis. The feedstock composition includes both essential and nonessential amino acids. The feedstock composition may also include nucleotides.

In one aspect, the feedstock composition provides a protein content of about 60 grams or more per 100 grams of acetogenic biomass, in another aspect, about 60 to about 90 grams per 100 grams of acetogenic biomass, in another aspect, about 65 to about 85 grams per 100 grams of acetogenic biomass, and in another aspect, about 70 to about 80 grams per 100 grams of acetogenic biomass, all on a dry weight basis.

In another aspect, the feedstock composition provides about 220 kcal or more per 100 grams of dry acetogenic biomass, in another aspect, about 220 kcal to about 400 kcal, in another aspect, about 250 kcal to about 350 kcal, in another aspect, about 300 kcal to about 325 kcal, and in another aspect, about 220 kcal to about 300 kcal.

In another aspect, the feedstock composition provides about 15 grams or more carbohydrates per 100 grams of dry acetogenic biomass, in another aspect, about 15 grams to about 60 grams, in another aspect, about 20 to about 40 grams, in another aspect, about 25 to about 35 grams, and in another aspect, about 30 to about 35 grams. In this aspect, the feedstock includes a weight ratio of carbohydrates to proteins of about 1.0 or less, in another aspect, about 0.75 or less, in another aspect, 0.5 or less, in another aspect, about 0.25 or less, and in another aspect, 0.1 or less. In one aspect, the feedstock has no detectable carbohydrates and only includes protein. In another aspect, the carbohydrate may include ethanol and/or water-soluble sugars.

The feedstock composition may also include fiber. Fiber may include acid detergent fiber, neutral detergent fiber, digestible fiber, and/or indigestible fiber. The feedstock composition may also include starch. In yet another aspect, the feedstock composition includes calcium, iron, sodium and potassium in the following amounts (all expressed as mg per 100 grams of acetogenic biomass on a dry weight basis): Calcium: about 18 mg or more, in another aspect, about 20 mg or more, in another aspect, about 25 mg or more, and in another aspect, about 30 mg or more; Iron: about 150 mg or more, in another aspect, about 175 mg or more, in another aspect, about 200 mg or more, and in another aspect, about 225 mg or more; Sodium: about 25 mg or more, in another aspect, about 30 mg or more, in another aspect, about 35 mg or more, and in another aspect, about 40 mg or more; Potassium: about 1200 mg or more, in another aspect, about 1300 mg or more, in another aspect, about 1400 mg or more, and in another aspect, about 1500 mg or more.

In one aspect, the feedstock composition may include de minimis amounts of metals. In an alternative aspect, the feedstock may include levels of certain desirable metals. Examples of metals that may or may not be present in the feedstock include zinc, molybdenum, cadmium, scandium, titanium, vanadium, chromium, manganese, iron, cobalt, nickel, copper, tungsten and selenium.

In another aspect, the acetogenic biomass may include any one of the following amino acids, either alone or in any combination (expressed as grams per 100 grams acetogenic biomass on a dry weight basis): Essential Amino Acids Content: Arginine: in one aspect, about 2.5 grams or more, in another aspect, about 3.0 grams or more, in another aspect, about 3.5 grams or more, in another aspect, about 4.0 grams or more, in another aspect, about 4.5 grams or more, in another aspect, about 5.0 grams or more, in another aspect, about 6.0 grams or more, and in another aspect, about 7.0 grams or more; Histidine: in one aspect, about 1.5 grams or more, in another aspect, about 2.0 grams or more, in another aspect, about 2.5 grams or more, in another aspect, about 3.0 grams or more, in another aspect, about 3.5 grams or more, in another aspect, about 4.0 grams or more, in another aspect, about 5.0 grams or more, and in another aspect, about 6.0 grams or more; Isoleucine: in one aspect, about 4.0 grams or more, in another aspect, about 4.5 grams or more, in another aspect, about 5.0 grams or more, in another aspect, about 5.5 grams or more, in another aspect, about 6.0 grams or more, in another aspect, about 7.0 grams or more, in another aspect, about 8.0 grams or more, and in another aspect, about 9.0 grams or more; Leucine: in one aspect, about 4.5 grams or more, in another aspect, about 5.0 grams or more, in another aspect, about 5.5 grams or more, in another aspect, about 6.0 grams or more, in another aspect, about 6.5 grams or more, in another aspect, about 7.0 grams or more, in another aspect, about 8.0 grams or more, and in another aspect, about 9.0 grams or more; Lysine: in one aspect, about 6.0 grams or more, in another aspect, about 6.5 grams or more, in another aspect, about 7.0 grams or more, in another aspect, about 7.5 grams or more, in another aspect, about 8.0 grams or more, in another aspect, about 9.0 grams or more, in another aspect, about 10.0 grams or more, and in another aspect, about 12.0 grams or more; Methionine: in one aspect, about 1.5 grams or more, in another aspect, about 2.0 grams or more, in another aspect, about 2.5 grams or more, in another aspect, about 3.0 grams or more, in another aspect, about 3.5 grams or more, in another aspect, about 4.0 grams or more, in another aspect, about 5.0 grams or more, and in another aspect, about 6.0 grams or more; Phenylalanine: in one aspect, about 2.5 grams or more, in another aspect, about 3.0 grams or more, in another aspect, about 3.5 grams or more, in another aspect, about 4.0 grams or more, in another aspect, about 4.5 grams or more, in another aspect, about 5.0 grams or more, in another aspect, about 5.5 grams or more, and in another aspect, about 6.0 grams or more; Threonine: in one aspect, about 3.0 grams or more, in another aspect, about 3.5 grams or more, in another aspect, about 4.0 grams or more, in another aspect, about 4.5 grams or more, in another aspect, about 5.0 grams or more, in another aspect, about 6.0 grams or more, in another aspect, about 7.0 grams or more, and in another aspect, about 8.0 grams or more; Tryptophan: in one aspect, about 0.4 grams or more, in another aspect, about 0.5 grams or more, in another aspect, about 0.6 grams or more, in another aspect, about 0.7 grams or more, in another aspect, about 0.8 grams or more, in another aspect, about 0.9 grams or more, in another aspect, about 1.0 grams or more, and in another aspect, about 1.5 grams or more; Valine: in one aspect, about 4.0 grams or more, in another aspect, about 4.5 grams or more, in another aspect, about 5.0 grams or more, in another aspect, about 5.5 grams or more, in another aspect, about 6.0 grams or more, in another aspect, about 7.0 grams or more, in another aspect, about 8.0 grams or more, and in another aspect, about 9.0 grams or more.

Other Amino Acids Content:

Alanine: in one aspect, about 5.0 grams or more, in another aspect, about 5.5 grams or more, in another aspect, about 6.0 grams or more, in another aspect, about 7.0 grams or more, in another aspect, about 8.0 grams or more, in another aspect, about 9.0 grams or more, in another aspect, about 10.0 grams or more, and in another aspect, about 11.0 grams or more; Aspartic Acid: in one aspect, about 7.0 grams or more, in another aspect, about 7.5 grams or more, in another aspect, about 8.0 grams or more, in another aspect, about 9.0 grams or more, in another aspect, about 10.0 grams or more, in another aspect, about 11.0 grams or more, in another aspect, about 12.0 grams or more, and in another aspect, about 14.0 grams or more; Cysteine: in one aspect, about 1.0 grams or more, in another aspect, about 1.5 grams or more, in another aspect, about 2.0 grams or more, in another aspect, about 2.5 grams or more, in another aspect, about 3.0 grams or more, in another aspect, about 3.5 grams or more, in another aspect, about 4.0 grams or more, and in another aspect, about 5.0 grams or more; Glutamic acid: in one aspect, about 9.0 grams or more, in another aspect, about 9.5 grams or more, in another aspect, about 10.0 grams or more, in another aspect, about 12.0 grams or more, in another aspect, about 14.0 grams or more, in another aspect, about 16.0 grams or more, in another aspect, about 18.0 grams or more, and in another aspect, about 20.0 grams or more; Glycine: in one aspect, about 3.0 grams or more, in another aspect, about 3.5 grams or more, in another aspect, about 4.0 grams or more, in another aspect, about 4.5 grams or more, in another aspect, about 5.0 grams or more, in another aspect, about 5.5 grams or more, in another aspect, about 6.0 grams or more, and in another aspect, about 7.0 grams or more; Methionine: in one aspect, about 1.5 grams or more, in another aspect, about 2.0 grams or more, in another aspect, about 2.5 grams or more, in another aspect, about 3.0 grams or more, in another aspect, about 3.5 grams or more, in another aspect, about 4.0 grams or more, in another aspect, about 5.0 grams or more, and in another aspect, about 6.0 grams or more; Proline: in one aspect, about 2.0 grams or more, in another aspect, about 2.5 grams or more, in another aspect, about 3.0 grams or more, in another aspect, about 3.5 grams or more, in another aspect, about 4.0 grams or more, in another aspect, about 4.5 grams or more, in another aspect, about 6.0 grams or more, and in another aspect, about 7.0 grams or more; Serine: in one aspect, about 2.5 grams or more, in another aspect, about 3.0 grams or more, in another aspect, about 3.5 grams or more, in another aspect, about 4.0 grams or more, in another aspect, about 4.5 grams or more, in another aspect, about 5.0 grams or more, in another aspect, about 5.5 grams or more, and in another aspect, about 6.0 grams or more; Tyrosine: in one aspect, about 2.5 grams or more, in another aspect, about 3.0 grams or more, in another aspect, about 3.5 grams or more, in another aspect, about 4.0 grams or more, in another aspect, about 4.5 grams or more, in another aspect, about 5.0 grams or more, in another aspect, about 5.5 grams or more, and in another aspect, about 6.0 grams or more.

In one embodiment, the feedstock composition may be utilized as feedstock in animal feed. In yet another embodiment, the feedstock composition may be utilized as feedstock in aquaculture. In yet another embodiment, the feedstock composition may be further processed and utilized as a nutrient supplement ingestible by animals and humans alike.

In one aspect, the present composition provides an effective amount of nutrients to a bacterial fermentation process. In this aspect, an "effective amount" describes use in promoting a healthy fermentation process which may include at least one of the following: production of total alcohol at a STY of about 1 g or more total alcohol/(L·day); providing a cell density of about 2.0 grams/liter or more; and maintaining the culture in a steady state. The bacterial fermentation process may be the fermentation of a CO-containing gaseous substrate and may be the same bacterial fermentation process from which the feedstock was originally derived.

In another aspect, the present composition provides an effective amount of nutrition to an animal. An "effective amount" describes use in promoting healthy growth in an animal is an amount sufficient to promote at least one of the following: inhibition of bacterial load in the animal; prevention or decrease the incidence of necrotic enteritis in poultry; stimulation of the immune response in the animal; enhancement of the effectiveness of antibiotics and vaccines administered to the animal in feed or otherwise; increased growth rate per amount of feed administered; increased milk production; decreases in mortality rate; and the like. Several factors may be considered, include but not limited to such factors as the animal's age, level of activity, hormone balance, and general health in determining the effective amount, which is tailored to the animal, for example by beginning with a low dosage and titrating the dosage to determine the effective amount.

Animals that can benefit from ingesting the present composition include, for example, poultry such as chickens, ducks, geese, turkeys, quail, game hens, and the like; beef and dairy cattle, pigs, goats, and the like; domestic animals such as dogs and cats; aquatic animals such as salmon, salmonids, trout, tilapia, shrimp, lobster and the like; and, humans. Uses of the protein-rich nutrient supplement include fattening cows, pigs, poultry, and fish. Other uses of the present composition include serving as emulsifying aids to improve the nutritive value of a multitude of consumable goods, including baked goods, soups, prepackaged meals, smart foods, and diet foods. Still other uses include paper processing, leather processing, and foam stabilization.

EXAMPLES

Example 1: A Continuous Bacterial Fermentation Process

A synthesis or waste gas containing CO and/or $CO_2/H_2$ is continuously introduced into a stirred tank bioreactor containing a strain of *Clostridium ljungdahlii*, along with a fermentation medium containing vitamins, trace metals and salts. A suitable fermentation medium used is reported in Table 1 below.

TABLE 1

FERMENTATION MEDIUM: COMPONENTS & CONCENTRATIONS

| Component | Provided As | 1x EtOH Conc (ppm) |
|---|---|---|
| NH4+ | NH$_4$Cl•(NH$_4$)$_2$HPO$_4$ | 838 |
| Fe | FeCl$_2$•4H$_2$O | 16.8 |
| Ni | NiCl$_2$•6H$_2$O | 0.198 |
| Co | CoCl$_2$•6H$_2$O | 0.991 |
| Se | Na$_2$SeO$_3$ | 0.0913 |
| Zn | ZnSO$_4$•7H$_2$O | 0.455 |
| Mo | Na$_2$MoO$_2$•2H$_2$O | 0.238 |
| Mn | MnCl$_2$•2H$_2$O | 0.167 |
| B | H$_3$BO$_3$ | 1.05 |
| Cu | CuCl$_2$•2H$_2$O | 0.149 |
| W | Na$_2$WO$_4$•2H$_2$O | 1.12 |
| K | KCl | 78.6 |
| Mg | MgCl$_2$•6H$_2$O | 59.8 |
| Na | NaCl | 78.7[a] |
| Ca | CaCl$_2$•2H$_2$O | 54.5[b] |
| Cysteine HCl | Cysteine HCl | 250 |
| PO4-2 | H$_3$PO$_4$•(NH$_4$)$_2$HPO$_4$ | 816 |
| Vitamins | Vitamin cocktail[c] | Variable[d] |

[a]Na+ concentration is from NaCl only. It does not include Na+ from the other components such as Na2WO4•2H2O,
[b]Ca + 2 concentration does not include calcium from pantothenic acid or calcium salt.
[c]Vitamins solution contains d-biotin, thiamine HCl, and d-pantothenic acid, calcium salt.
[d]Varies considerably from 0.3-0.5 ml at inoculation to as much as 0.7-0.8 ml at high gas rates.

During method start-up using a culture inoculum of 10% or less the reactor is operated with a batch liquid phase, where the fermentation medium is not fed continuously to the reactor. The liquid phase in the reactor thus consists of a batch of fermentation medium with a nominal concentration of one or more limiting nutrients, e.g., calcium pantothenate, cobalt. Alternatively, a rich medium containing yeast extract, trypticase, or other complex nutrients can also be employed.

Ideally, the gas phase at start-up is $CO_2$-free and contains excess $H_2$. The gas rate and agitation rate are kept at low levels (less than 500 rpm in a New Brunswick Scientific Bioflo® fermentation bioreactor) to yield CO and $H_2$ in slight excess, but at the same time, avoiding CO substrate inhibition. In a one-liter laboratory New Brunswick Scientific Bioflo® fermentation bioreactor, as an example, where the feed gas composition is 63% $H_2$, 32% CO and 5% $CH_4$, the agitation rate to initiate start-up is 400 rpm and the gas rate is 20 ml/min. To bring about ethanol production during start-up, there is in excess both $H_2$ and liquid nutrients. Limitations placed on certain nutrients within the fermentation medium take place at a later time. Thus, excess liquid nutrients (e.g., calcium pantothenate, cobalt) are actually present during start-up to avoid unwanted culture acclimation to low nutrients.

As bacterial fermentation proceeds over a period of several hours post-inoculation, $CO_2$ is produced from the conversion of CO, and $H_2$ is consumed along with the $CO_2$, which is a signal to nominally increase the agitation rate to avoid gas mass transfer limitation. In the New Brunswick Scientific Bioflo® CSTR, the exit gas is 25% CO, 67% $H_2$, 2% $CO_2$, and 6% $CH_4$. If the agitation rate is increased too quickly, CO substrate inhibition occurs, as evidenced by a decrease in methane concentration after an increase in agitation. Thus, the agitation rate might typically be increased by 200 rpm in 24 hours.

The procedure of monitoring $CO_2$ production (or $H_2$ conversion) while nominally increasing agitation rate occurs at a relatively rapid rate until the target agitation rate is reached. A typical target agitation rate in the New Brunswick Scientific Bioflo® fermentation bioreactor is 900 rpm. During this time of increasing agitation rate in batch liquid culture, monitoring cell production takes precedence over instigating product formation. Thus, cell concentrations of about 1.5 g/L are attained, while typical product concentrations are 10 g/L ethanol and 2 g/L acetate from the batch culture.

Once the target agitation rate is reached, the system is allowed to grow to maximum $H_2$ uptake. It is desirable to have very high $H_2$ exit concentrations (typically >60%) to assure ethanol production while limiting acetic acid production. The liquid fermentation medium feed is then turned on (for systems having batch inoculation from stock culture) to initiate continuous liquid feed and the gas feed rate is increased toward the target flow rate. In the laboratory New Brunswick Scientific Bioflo® fermentation bioreactor the liquid feed rate is typically 0.5 ml/min, while the gas flow rate is increased by 10 to 15% every 24 hours toward a target rate of 125 ml/min.

As the gas flow rate is increased, cell production increases until the reactor is eventually limited on liquid phase nutrients (e.g., calcium pantothenate, cobalt) as evidenced by a small drop in $H_2$ conversion, at the target productivity. In the New Brunswick Scientific Bioflo® CSTR, this is recognized by a 10% drop in $H_2$ conversion at a target productivity of 20 g/L·day.

The production method and bacterial fermentation reactor system are then maintained at a steady state producing 15 to 35 g/L ethanol and 0 to 5 g/L acetate as products, with only occasional small adjustments in limiting nutrients, liquid rates and gas rate. Typical steady state conditions in the laboratory New Brunswick Scientific Bioflo® fermentation bioreactor without cell recycle, are a gas retention time (gas flow rate/reactor liquid volume) of 20 minutes, a liquid retention time (liquid flow rate/reactor liquid volume) of 30 hours and an agitation rate of 900 rpm, yielding CO conversions of 92% and $H_2$ conversions of 60% with a pantothenate limitation.

In one embodiment, cell recycle is added to the reactor system at this time along with an adjustment in gas rate (increase) and a first nutrient concentration (decrease). With cell recycle in the New Brunswick Scientific Bioflo® CSTR, the gas retention time is typically 8 minutes, the liquid retention time is 12 hours, the cell retention time is 40 hours and the agitation rate is 900 rpm. These conditions typically yield a CO conversion of 92% and a $H_2$ conversion of 50% with a pantothenate limitation. This method of continuous fermentation allows for the continuous production and maintenance of high ethanol concentrations with low by-product acetate concentrations under stable operating conditions to enhance use of subject bacterial on an industrial scale for ethanol production.

Example 2: Purging of Bacterial Cells from a Fermentation Vessel to Control Fermentation Product Ratios A gaseous substrate (30% CO, 15% $H_2$, 10% $CO_2$, 45% $N_2$) fermentation takes place in a CSTR (pH=5.0, Temperature=38° C., Pressure=20 psig) utilizing *C. ljungdahlii*, strain C-01, with cell recycle (cell retention time=40 hours and the liquid retention time=6 hours) and the culture is not limited in growth by cobalt, calcium pantothenate, or any other nutrient. As the culture grows, a cell density is attained such that the specific uptake (mmol CO per gram of dry cells per minute) is below 0.5 and acetic acid is produced preferentially to ethanol. To prevent this occurrence, the cell purge rate is increased to prevent an increase in cell density, such that the steady concentration of cells is kept low enough to maintain a specific uptake higher than 0.5 mmol CO per gram dry cells per minute. In doing so, the cell retention time is reduced to between 6 and 25 hours. See Table 2 for the monitoring of cell concentration during a bacterial fermentation process of a strain of *C. ljungdahlii*.

TABLE 2

Cell Concentrations of Different Fermentation Liquid Broth from Various Cell Purges at Different Time Intervals

| Time (hr) | % Water Recycle | Cell Conc.[a] (g/L) | CO (%) | $H_2$ (%) | Ethanol (g/L) | Acetate (g/L) | Net Acetate (g/L) | Productivity (g/L · day) |
|---|---|---|---|---|---|---|---|---|
| 75 | 25 | 2.1 | 95 | 68 | 12 | 4 | 4 | 12 |
| 193 | 50 | 2.1 | 95 | 75 | 15 | 6 | 5 | 15 |
| 462 | 75 | 2.1 | 92 | 60 | 17 | 5 | 4 | 17 |
| 554 | 50 | 1.6 | 85 | 30 | 17→13 | 5 | 3 | 12-16 |
| 669 | 75 | 2.6 | 92 | 75 | 13→19 | 5 | 3 | 12-18 |
| 943 | 100 | 3.0 | 92 | 70 | 23 | 6 | 3 | 23 |
| 1087 | 100 | 3.0 | 92 | 60 | 23 | 6 | 0 | 23 |
| 1232 | 100 | 2.7 | 92 | 60 | 23 | 6 | −0 | 23 |
| 1375 | 100 | 3.0 | 91 | 60 | 27 | 6 | −1 | 27 |
| 1534 | 100 | 3.5 | 88 | 35 | 23 | 5 | 0 | 23 |

[a] Dry cell weight basis

Example 3: Analysis of Cell Biomass of Acetogenic Bacterial Cells

*Clostridium ljungdahlii* C-01 was grown in a bioreactor with syngas. A sample of the fermentate from the bioreactor and concentrated dry mass of the biomass cells was analyzed in accordance with the following procedures in Table 3.

TABLE 3

Procedures for analyzing fermentate samples

| | |
|---|---|
| AOAC 990.08: | Calcium, Iron, Sodium |
| Heavy metals: | ICP-M, based on AOAC 993.14 |
| AOAC 994.10: | cholesterol |
| AOAC 996.06: | crude fat |
| AOAC 992.16/991.43: | dietary fibers |
| AOAC 980.13: | sugars |
| AOAC 926.08: | moisture |
| AOAC 990.03/992.23: | protein |
| AOCS Ce 1j-07 and Ce 1h-05, AOAC 996.06: | fat |
| 21 CFR 101.9: | caloric content by calculation |

The results of the analysis of the concentrated dry mass of the cells biomass are shown in Table 4.

TABLE 4

Results of Dry Weight of Biomass
Results of analysis were as follows:

| Analyte | Content per 100 grams acetogenic biomass (dry weight basis) |
|---|---|
| carbohydrates | 33.0 g |
| calories (bomb calorimetry) | 224.2 kcal |
| protein | 60.4 g |
| Calcium | 18 mg |
| Iron | 152 mg |
| Sodium | 25 mg |
| Potassium | 1200 mg |

The results of the amino acid analysis of the concentrated dry mass of the cells biomass are shown in Table 5 hereunder.

Example 4: Analysis of Protein, Carbohydrates, and Nucleic Acid Content of Acetogenic Bacterial Cells

*Clostridium ljungdahlii* C-01 was grown in a bioreactor with syngas. Cell culture was centrifuged at 4,000 RPM to remove culture medium. Pellets were collected and allowed to dry in an oven at 100 C overnight. 100 grams of crushed, dried pellet was sent for analysis using the same tests for carbohydrates and protein as described in Example 3. Table 6 indicates that up to 80% of cell mass is protein.

TABLE 5

Results of Amino Acid Analysis of the Dry Weight of Biomass

| | Grams per 100 grams acetogenic biomass (dry weight basis) |
|---|---|
| Total amino acids | |
| Aspartic acid | 7.36 |
| Threonine | 3.29 |
| Serine | 2.83 |
| Glutamic acid | 9.18 |
| Proline | 2.29 |
| Glycine | 3.28 |
| Alanine | 5.44 |
| Valine | 4.39 |
| Methionine | 1.83 |
| Isoleucine | 4.44 |
| Leucine | 4.95 |
| Tyrosine | 2.58 |
| Phenylalanine | 2.90 |
| Histidine | 1.70 |
| Lysine | 6.28 |
| Arginine | 2.77 |
| Cysteine | 1.05 |
| Methionine | 1.88 |
| Tryptophan | 0.48 |
| Free Amino Acids | |
| Glytamic acid | 0.07 |

TABLE 6

Three Components of Consideration in a Protein-Rich Nutrient Supplement

| Test Number | Carbohydrate | Protein | Nucleic Acid [a] |
|---|---|---|---|
| 1 | 33% | ≥60.6% | ≥3% |
| 2 | 7.06% | ≥78.1% | ≥3% |
| 3 | — | ≥78.9% | ≥3% |

[a] Rationale owing to there being a non-protein nitrogen content that is less than 1%. The ratio of nitrogen in nucleic acid is about 3 g RNA/DNA to 1 g Nitrogen, such that the samples contained no more than 3% nucleic acid.

Example 5: Rupturing of Bacterial Cells by One or More Micro Fluidization Rupturing Devices and the Protein Recovery for Rupturing of Bacterial Cells by the Micro Fluidization Rupturing Devices The Microfluidizer by Microfluidics was identified as a rupturing device to rupture anaerobic bacterial cells from the fermentation process and produce a protein-containing portion. A volume of fermentation liquid was obtained from a fermentation vessel. Samples were concentrated 1.5-fold by centrifugation or to a cell concentration of for example, about 20 g/L or larger. For example, about 15 g/L of a fermentation liquid was obtained from a fermentation vessel and Samples were concentrated by centrifugation to obtain a cell density of 22.4 g/L or higher.

The resulting cells were re-suspended in solutions (e.g., into a 2 L solution which may contain about 44 g of cells) and sent to Microfluidics. The microfluidization process involves rupturing cells with high shear forces created by forcing the cells through micro-channels within the Microfluidics reaction chamber at high pressures.

Each sample was run at a different amount of time(s) and at a different pressure. The pressures tested ranged between 10,000 and 30,000 pounds per square inch (psi) for one or multiple passes. Each pass constitutes a run through the Microfluidizer. Pressure was supplied at a constant rate via the rupturing device. The Microfluidizer generated six homogenized samples. The cell-containing suspensions can be treated with one or more additives (e.g., detergents, enzymes, etc.), and passed through the Microfluidizer (e.g., at high shearing or pressures at 3,000 psi or larger).

Several experiments were performed. Each sample was run at a different amount of time(s) and at a different pressure. Among them, the conditions for six exemplary sample treatment experiments are shown: (1) a single pass at 18,000 psi; (2) two passes at 18,000 psi; (3) a single pass at 23,000 psi; (4) two passes at 23,000 psi; (5) a single pass at 28,000 psi; (6) two passes at 28,000 psi. Each pass constitutes an experiment passing through the Microfluidizer. Pressure was supplied at a constant rate via the rupturing device. The resulting six homogenized samples of protein-containing fractions were generated after treatment with the Microfluidizer. Each sample of the protein-containing fraction was analyzed for protein content using a Bradford assay.

In one experiment, some samples were treated with only one pass through the Microfluidizer. After one pass, a first protein-containing portion was separated out of the homogenate. Then, the first protein-containing portion can be spray dried to obtain protein containing powder.

In a second experiment, samples were treated with two passes through the Microfluidizer, where a pretreated cell-containing suspension flowed through a recycle stream to re-enter the Microfluidizer a second time. After two passes, a protein-containing portion was obtained. Then, powder form of the protein-containing portion can be obtained. For example, three different drying techniques (drying at high temperatures, spray drying, and lyophilizing) were tested after the protein-containing portion was obtained.

Example 6: Fractionating of the Homogenates of the Ruptured Bacterial Cells by One or More Filtration-Type Fractionator Devices The homogenate of the protein-containing portion after the treatment process of Example 5 was filtered through a nylon filter. Filtration of the homogenate allowed 5-15% of the original microbial biomass to be recovered as soluble protein, as indicated in Table 7.

TABLE 7

Percentage recovery of soluble proteins after filtration.

| | Percent recovery of soluble proteins | | | |
|---|---|---|---|---|
| Sample | Filtered | 2,000 RPM | 5,000 RPM | 10,000 RPM |
| Run 1 | 5%-15% | 10%-25% | 5%-15% | 5%-15% |
| Run 2 | 5%-15% | 10%-25% | 5%-15% | 5%-15% |

Example 7: Fractionating of the Homogenates of the Ruptured Bacterial Cells by One or More Centrifugation-Type Fractionator Devices The homogenate of Example 4 underwent centrifugation at speeds between 2,000 and 10,000 RPM for 6 minutes and the protein content was analyzed using the Bradford protein assay. The percent of soluble protein recovery was calculated using the starting biomass concentration as a basis. Results indicate that up to 25% of protein was recovered after microfluidization, indicating that microfluidization followed by centrifugation is a viable method to lyse cells and recover soluble protein.

As another example, a cell suspension with a cell density of 22.4 g/L (cells in fermentation broth) was sent to Microfluidics. One sample was passed through a Microfluidizer at 18,000 psi and another sample was passed through the same type of Microfluidizer twice at a pressure of 28,000 psi. The results were compared and obtained as shown in Table 8.

For the samples passing one time at 18,000 psi, the protein concentration in the homogenate was 9.5 mg/mL. The sample was then filtered OR centrifuged and further analyzed. After filtration through a 0.45-micron filter, the protein-rich fraction contained 2.4 mg/mL of protein. After centrifugation for 8 minutes at 2,000 RPM, the protein concentration of the protein-rich fraction is about 3.2 mg/mL protein. Higher centrifuge speeds resulted in less protein (at 5,000 RPM, the protein concentration of the recovered fraction was about 1.0 mg/mL or higher, or about 1.9 mg/mL or higher. At much higher centrifuge speed of 10,000 RPM, the resulting protein concentration of the supernatant fraction after the spin was about 1.4 mg/mL).

TABLE 8

Protein Concentration (µg/mL) and Percentage (%) within Homogenates (Mixtures of Ruptured Bacterial Cells)

| | | Filtered [b] | Centrifuged (rpm) | | |
|---|---|---|---|---|---|
| | Homogenate [b] | (0.45-micron filter) | 2,000 rpm | 5,000 rpm | 10,000 rpm |
| 18k, 1 pass Protein Recovery [a] | 9502 µg/mL 42.4% | 2371 µg/mL 10.6% | 3178.4 µg/mL 14.2% | 1878.6 µg/mL 8.4% | 1423.3 µg/mL 6.35% |

TABLE 8-continued

Protein Concentration (μg/mL) and Percentage (%) within Homogenates (Mixtures of Ruptured Bacterial Cells)

| | | Filtered [b] | Centrifuged (rpm) | | |
|---|---|---|---|---|---|
| | Homogenate [b] | (0.45-micron filter) | 2,000 rpm | 5,000 rpm | 10,000 rpm |
| 28k, 2 passes | 8549 μg/mL | 1777 μg/mL | 3006.9 μg/mL | 2007.8 μg/mL | 1330.3 μg/mL |
| Protein Recovery [a] | 38.2% | 7.9% | 13.4% | 8.96% | 5.94% |

[a] Percentages calculated by determining protein content of total cell mass.
[b] Homogenate and filtered samples were diluted by 11X prior to measuring.

Another group of samples were treated with two passes through the Microfluidizer at 28,000 psi, where a previously lysed cell-containing suspension flowed through a recycle stream to re-enter the Microfluidizer a second time. The resulting protein concentration of the protein-containing portion in the homogenate was measure at around 8.5 mg/ml. The samples were then filtered and/or centrifuged. After filtration through a 0.45-micron filter, the resulting protein concentration was about 1.8 mg/ml. After centrifugation for 8 minutes at 2000 RPM, the resulting protein concentration was about 3.0 mg/ml. Higher centrifuge speed resulted in less protein (at 5000 RPM, it was 2.0 mg/ml; at 10000 RPM it was 1.3 mg/ml).

Example 8: Cell Lysis from the Rupturing of Bacterial Cells by One or More Micro Fluidization Rupturing Devices The rupturing devices selected to conduct the rupturing process can be microfluidizer and other commercially available devices. In FIGS. 7B-7E, the rupturing devices selected to conduct the rupturing process is a microfluidizer. The rupturing process inside the rupturing device can be conducted under different variables, including pressure and times of passes.

Figure 7A:
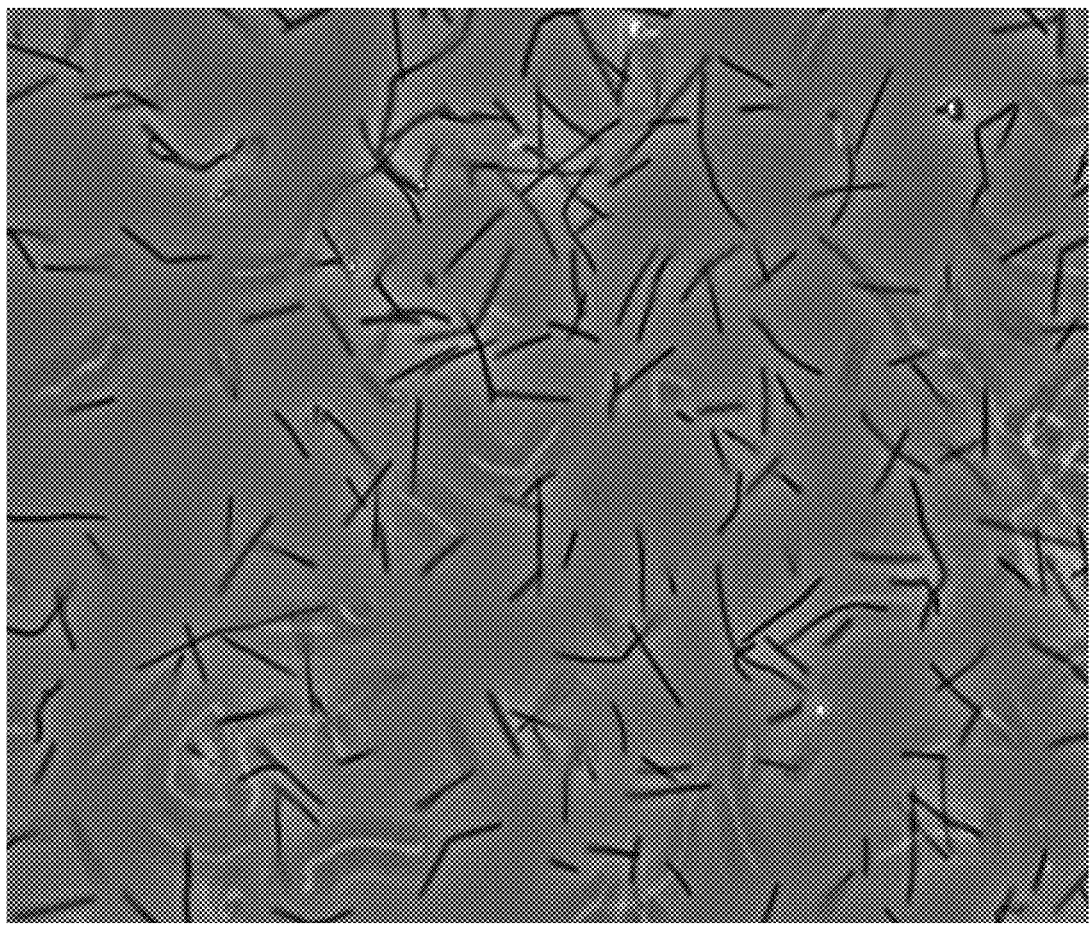
FIG. 7A shows an electronic micrograph of one example of a cell-containing suspension before rupturing anaerobic bacterial cells within the cell-containing suspension into a homogenate, according to one or more embodiments of the invention.

FIG. 7A illustrates an electron micrograph of the cell containing suspension that was not subjected to lysis. The electronic micrograph was taken by a microscope and at a 100× magnification targeting the homogenate.

The cell-containing suspension selected for undergoing the rupturing process inside the rupturing device can be of different densities. In FIG. 7A, the density of cell-containing suspension that did not undergo a rupturing process is about 10 g/L or higher, such as about 16 g/L or higher.

Figure 7B:
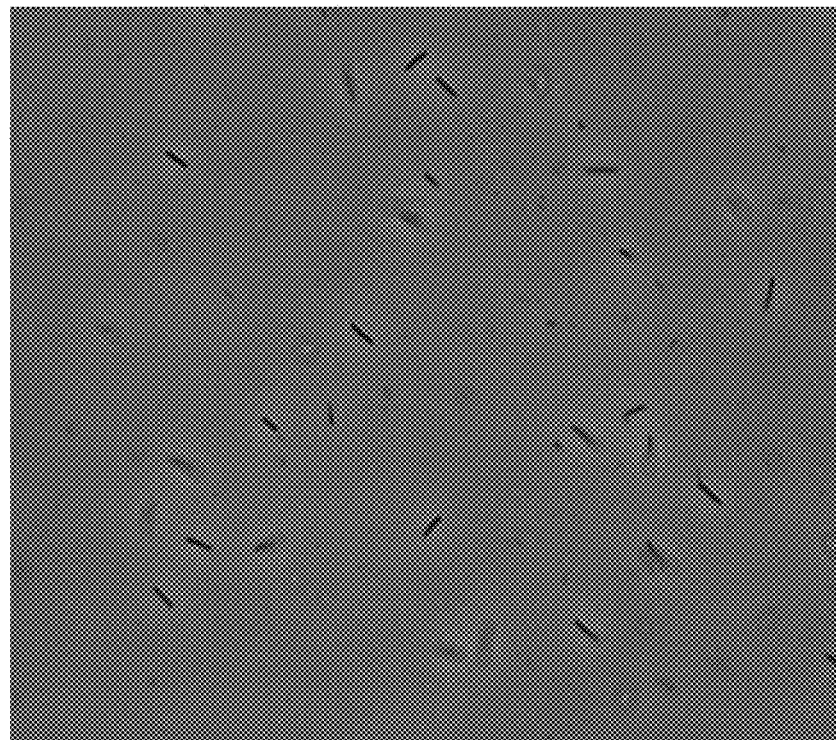
FIG. 7B shows an electronic micrograph of one example of a homogenate obtained from a rupturing device after rupturing anaerobic bacterial cells within a cell-containing suspension of a bacterial fermentation liquid broth, according to one or more embodiments of the invention.

FIG. 7B illustrates another electron micrograph of the homogenate which is obtained inside the rupturing device 460, 560, or 660, and is a product from rupturing cell membranes of the anaerobic bacterial cells within the cell-containing suspension inside the rupturing device 460, 560, or 660, according to one or more embodiments of the invention.

The electronic micrograph was taken by a microscope and at a 100× magnification targeting the homogenate. In this FIG. 7B, the rupturing devices selected to conduct the rupturing process is a microfluidizer. In this FIG. 7B, the rupturing process is conducted at a pressure of 1,000 psi or higher (e.g., between 1,000 pounds per square inch (psi) to 9,000 psi or higher) against the cell-containing suspension and with one pass. Also, in FIG. 7B, the cell density of cell-containing suspension selected for this rupturing process inside the rupturing device is about 10 g/L or higher, such as at about 16 g/L or higher. Visually, there is significant damage done to the cell membranes as a result of the microfluidization process.

Figure 7C:
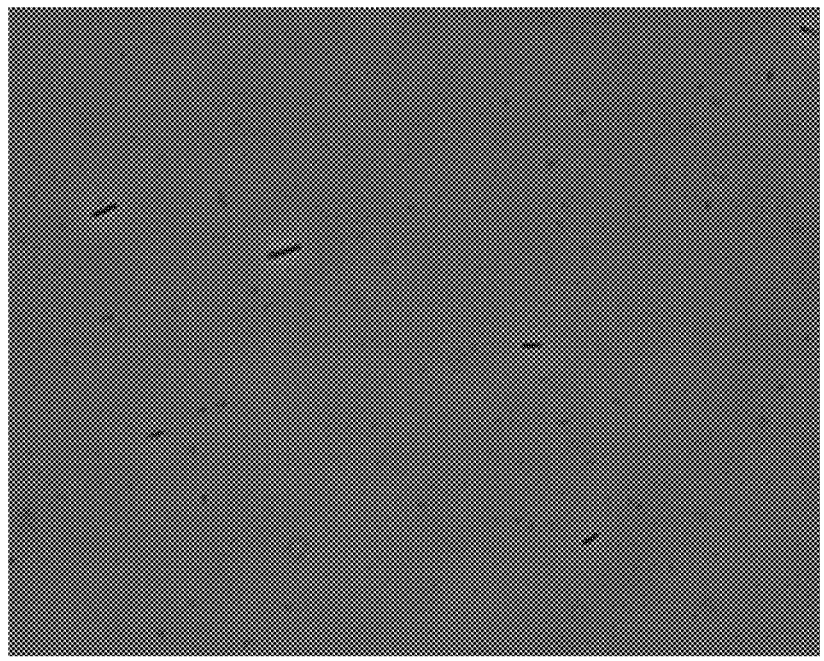
FIG. 7C is still another example of an electronic micrograph, showing the anaerobic bacterial cells within the cell-containing suspension after it is ruptured inside the rupturing devices, according to one or more embodiments of the invention.

FIG. 7C illustrates an electron micrograph of the cell membranes of the anaerobic bacterial cells within the cell-containing suspension before it is ruptured inside the rupturing devices 460, 560, or 660, according to one or more embodiments of the invention.

The electronic micrograph was taken by a microscope and at a 100× magnification targeting the homogenate. In this FIG. 7C, the cell density of the cell-containing suspension selected for this rupturing process inside the rupturing device is about 10 g/L or higher, such as at about 16 g/L or higher. The rupturing process is conducted at a pressure of about 1,000 psi or higher (e.g., between 1,000 pounds per square inch (psi) to 20,000 psi or higher) against the cell-containing suspension and with one pass. Compared to the results in FIG. 7A, the results as shown in FIG. 7C show significant rupturing of the cell membranes occurred at this processing pressure.

Figure 7D:
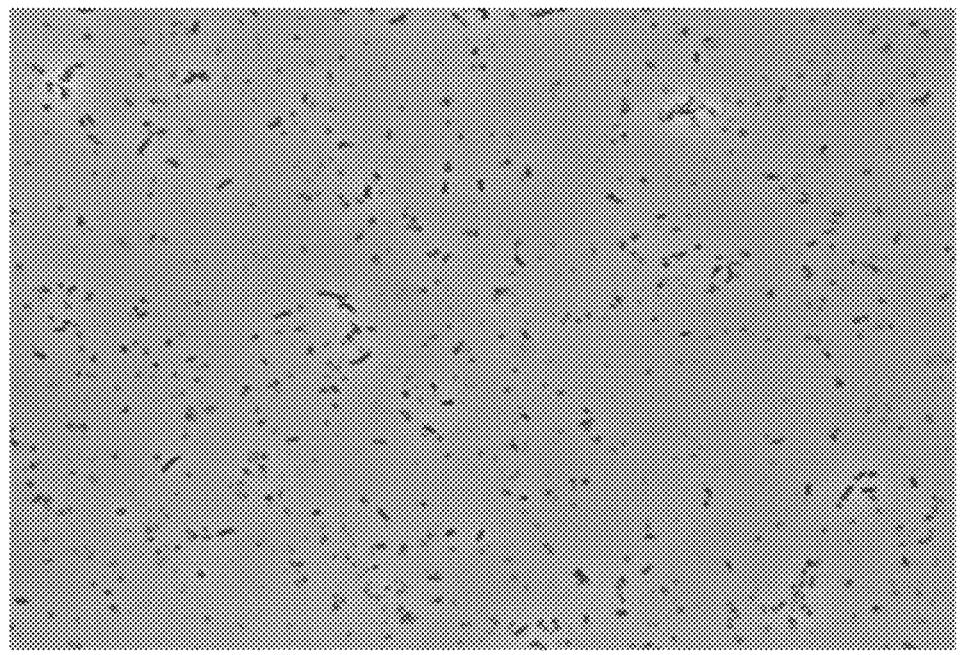
FIG. 7D is another example of an electronic micrograph of a homogenate, showing ruptured cell membranes of the anaerobic bacterial cells within the cell-containing suspension after ruptured by the rupturing device at high pressure, according to one or more embodiments of the invention.

FIG. 7D illustrates another electron micrograph of the homogenate which is obtained inside the rupturing device 460, 560, or 660, and is a product from rupturing cell membranes of the anaerobic bacterial cells within the cell-containing suspension inside the rupturing device 460, 560, or 660, according to one or more embodiments of the invention.

The electronic micrograph was taken by a microscope and at an 800× magnification targeting the homogenate. In this FIG. 7D, the rupturing devices selected to conduct the rupturing process is a microfluidizer. In this FIG. 7D, the rupturing process is conducted at a pressure of 1,000 psi (e.g., between 1,000 pounds per square inch (psi) to 22,000 psi or higher) against the cell-containing suspension and with one pass. Also, in this FIG. 7D, the density of cell-containing suspension selected for this rupturing process inside the rupturing device is about 15 g/L or higher, such as at about 20 g/L or higher, or about 22.4 g/L or higher.

Figure 7E:
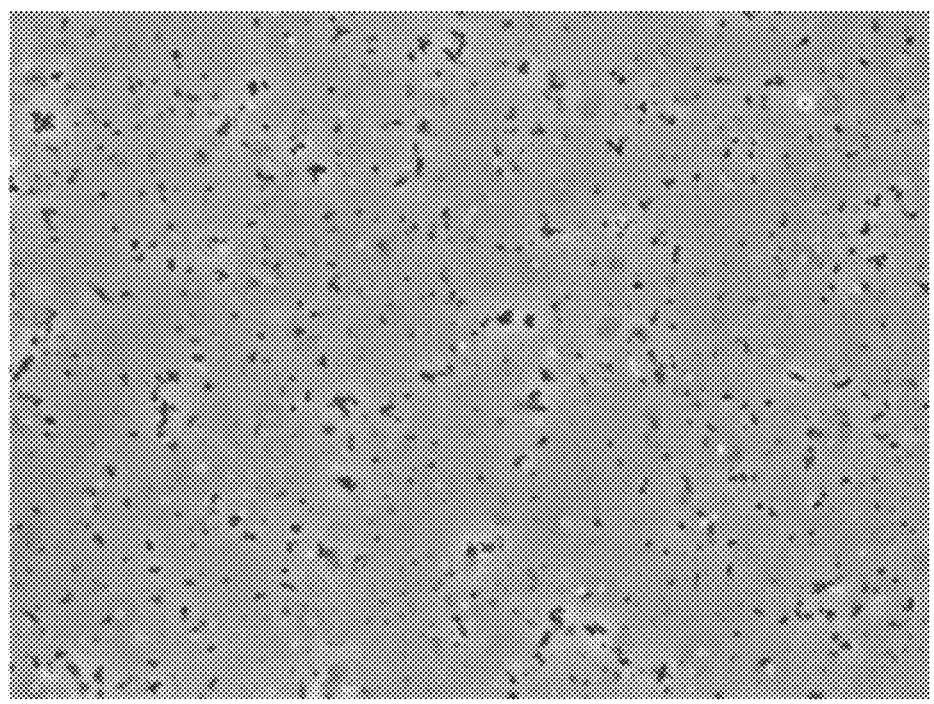
FIG. 7E is still another example of an electronic micrograph of a homogenate, showing ruptured cell membranes of the anaerobic bacterial cells within the cell-containing suspension after ruptured by the rupturing device at very high pressure, according to one or more embodiments of the invention, according to one or more embodiments of the invention.

FIG. 7E illustrates another electron micrograph of the homogenate which is obtained inside the rupturing device 460, 560, or 660, and is a product from rupturing cell membranes of the anaerobic bacterial cells within the cell-containing suspension inside the rupturing device 460, 560, or 660, according to one or more embodiments of the invention.

The electronic micrograph was taken by a microscope and at an 800× magnification targeting the homogenate. In this FIG. 7E, the rupturing devices selected to conduct the rupturing process is a microfluidizer. In this FIG. 7E, the rupturing process is conducted at a pressure of the pressure of 1,000 psi (e.g., between 25,000 pounds per square inch (psi) to 30,000 psi or higher) against the cell-containing suspension and with two passes. Also, in this FIG. 7E, the cell density of cell-containing suspension selected for this rupturing process inside the rupturing device is about 15 g/L or higher, such as at about 20 g/L or higher, or about 23 g/L or higher.

Example 9: Rupturing of Bacterial Cells by One or More Micro Fluidization Rupturing Devices with Pretreatment of the Bacterial Cells in a Cell-Containing Holding Tank The Microfluidizer rupturing device (e.g., Microfluidics device) was used to rupture anaerobic bacterial cells from the fermentation process and produce a protein-containing portion. The fermentation liquid broth (e.g., at 15 g/L of cell density) was obtained from the high cell density lab reactor of a fermentation vessel. Samples were concentrated by centrifugation to obtain a cell density of 45 g/L. The resulting cell suspension (2 L containing 90 g of cells) was sent to a cell-containing holding tank for pretreatment.

The microfluidization process involves rupturing cells with high shear forces created by forcing the cells through a 1-micron reaction chamber at high pressures. Cell-containing suspensions containing the bacterial cells were split into six samples. The cell-containing suspensions were treated with one or more additives (e.g., detergents, enzymes, etc.), and passed through the Microfluidizer at 15,000 psi. Only one pass through the microfluidizer rupturing device was conducted. After one pass, a first protein-containing portion was separated out of the homogenate and spray dried.

Example 10: Rupturing of Bacterial Cells by One or More Sonication Rupturing Devices A sonicator was identified as a rupturing device to rupture anaerobic bacterial cells from the fermentation process and produce a protein-containing portion. 15 g/L fermentation liquid was obtained from the high cell density lab reactor of a fermentation vessel. Samples were concentrated by centrifugation to obtain a cell density of 22.4 g/L. The resulting cell re-suspension (2 L containing 44 g of cells) was subjected to sonication. The sonication process involves rupturing cells with high force via sound energy at ultrasonic frequencies that agitate the cells and break open the cell membranes. The cell-containing suspension containing the bacterial cells was split into six samples. Each sample was subjected to sonication.

Example 11: Rupturing of Bacterial Cells by One or More Sonication Rupturing Devices with Pretreatment of the Bacterial Cells in a Cell-Containing Holding Tank A sonicator was identified as a rupturing device to rupture anaerobic bacterial cells from the fermentation process and produce a protein-containing portion. Fermentation liquid broth was obtained from three high cell density fermentation vessels. Samples were concentrated via centrifugation to obtain cell densities between 4 and 10 mg/ml.

For example, a fermentation liquid broth obtained from a fermentation vessel (in this example, an exemplary vessel A) containing about 4.2 mg/ml of bacterial cells was subjected to sonication in a variety of buffers. A cell-containing suspension from another fermentation vessel (an exemplary vessel B) of containing about 9.2 mg/ml of anaerobic bacterial cells was subjected to sonication in a variety of buffers. A cell-containing suspension from another fermentation vessel (an exemplary vessel C) of containing about 7.1 mg/ml of cells was also subjected to sonication in a variety of buffers.

After collection of fermentation broths from the fermentation vessel, the bacterial cells from the fermentation broth were spun down via centrifugation (e.g., spinning down the bacterial cells at 4,000 RPM or higher centrifugation speed) and re-suspended in their respective buffers.

Cells were resuspended in detergent-containing buffer (TrisHCl pH 8 containing sodium dodecyl sulfate (SDS), CHAPS, Triton X-100, or Tween 20) or enzyme-containing buffer (TrisHCl pH 8 containing lysozyme). TrisHCl pH 8 was used as the control buffer. The resulting cell suspension was subjected to sonication.

Cells were sonicated in 5-second pulses followed by resting on ice in between. The cycle was repeated three times. After sonication, cells were spun down for 10 minutes at 20K RPM and the supernatant was removed. The soluble protein fraction was analyzed for protein content using a Lowry-based protein assay. Percentages of soluble protein recovery were calculated based on concentration of cells subjected to sonication.

Several samples were also subjected to a freeze/thaw cycle, wherein the cells were completely frozen in TrisHCl buffer. After freezing at −80 degrees Celsius, cells were completely thawed before re-freezing. This cycle was completed 5 times. After completion, cell-containing suspension was spun down at 20,000 RPM for 10 minutes and the supernatant was removed. Table 9 shows the protein recovery amounts by the buffer type that the cell-containing suspension samples were subjected to. Percentages of soluble protein recovery was calculated based on initial starting materials. Starting materials include fermentation liquid comprising a liquid nutrient medium, other essential minerals, and an accumulation of acetogenic biomass.

Fermentation liquid was obtained from three high cell density fermentation vessels. Samples were concentrated via centrifugation at 4,000 RPM to obtain cell densities between 4 and 10 mg/ml. Cells were resuspended in detergent-containing buffer (TrisHCl pH 8 containing sodium dodecyl sulfate (SDS), CHAPS, Triton X-100, or Tween 20) or enzyme-containing buffer (TrisHCl pH 8 containing lysozyme). TrisHCl pH 8 was used as the control buffer. The resulting cell suspension was subjected to sonication. The sonication process involves rupturing cells with high force via sound energy at ultrasonic frequencies that agitate the cells and break open the cell membranes.

Cells were sonicated in 5-second pulses followed by resting on ice in between. The cycle was repeated three times. After sonication, cells were spun down for 10 minutes at 20,000 RPM and the supernatant was removed. The soluble protein fraction was analyzed for protein content using a Lowry-based protein assay. Percentages of soluble protein recovery were calculated based on concentration of cells subjected to sonication.

The results, shown in Table 9, indicate that detergent additives can increase the solubility of proteins when cells are subjected to sonication. Specifically, the addition of SDS or lysozyme greatly enhances the solubility of membrane proteins.

Example 12: Fractionating of the Homogenates of the Ruptured Bacterial Cells by One or More Filtration-Type Fractionator Devices The homogenate of Example 4 is filtered through a nylon filter. Filtration of the homogenate allowed 10.7% of the original microbial biomass to be recovered as soluble protein.

TABLE 9

Ruptured Protein Recovered by Percentage (%)

| Buffer Type | Vessel Type 1 | Vessel Type 2 | Vessel Type 3 |
|---|---|---|---|
| 0.1-1% SDS | 20-35 | 13-26 | 25-35 |
| 0.5-2% CHAPS | 7-18 | 7-12 | 5-11 |
| 0.1-2% Triton X-100 | 10-25 | 5-10 | 5-13 |
| 2.5-5% Tween 20 | 10-20 | 10-20 | 10-20 |
| Control | 15-20 | 8-13 | 8-13 |
| Tris HCl | 5-10 | 5-10 | 5-10 |
| Freeze/Thaw | | | |
| Lysozyme | 25-30 | 15-20 | 15-20 |

Example 13: Fractionating of the Homogenates of the Ruptured Bacterial Cells by One or More Centrifugation-Type Fractionator Devices The homogenate of Example 4 underwent centrifugation at 2000 rpm, which fractionated 3.2 mg of protein into supernatant. Centrifugation of the homogenate allowed a 14.3% recovery of soluble protein separated out of the total cell mass of the initial microbial biomass collected from the fermentation vessel.

Example 14: Determination of pH Effect in the Cell-Containing Suspension on Protein Recovered after Rupturing Through One or More Rupturing Devices Samples were collected from a high cell density fermentation vessel containing cells of *Clostridium ljungdahlii*. The cell concentration at the time of collection was approximately 22 g/L and had a pH value of approximately 4.5. A volume of cell culture was spun down at 4,000 RPM for 10 minutes. Cell pellets were re-suspended in the same volume of TrisHCl as the volume of culture media that was removed after centrifugation (so that samples were not concentrated or diluted). Multiple volumes of cell culture were subjected to pH modification through addition of 0.5M NaOH so that the final pH of the culture broth was between 3.5 and 10. Samples were processed between 10,000 and 20,000 psi for one or multiple passes. Each sample was spun down at 13,300 RPM for 6 minutes. The supernatant was collected and a Lowry-based protein assay was used to determine protein concentration in the soluble fraction.

Data, shown in Table 10, indicates that an increase in pH of cell sample prior to microfluidization enhances protein solubility. Specifically, when the pH is high (above 7.6), the recovery of soluble protein is enhanced.

TABLE 10

Ruptured Protein Recovered by Percentage (%)

| Sample | Passes | mg/ml | Recovery % |
|---|---|---|---|
| pH 3.5-5 | 1-4 | 2.5-3.5 | 12-15 |
| pH 5-7.5 | 1-4 | 7-10 | 40-45 |
| pH 7.6-10 | 1-4 | 10-15 | 50-55 |
| TrisHCl pH 8 | 1-4 | 9-15 | 40-60 |

Example 15: Determination of pH Effect in the Cell-Containing Suspension on Protein Recovered after Rupturing Through One or More Rupturing Devices Samples were collected from a high cell density fermentation vessel containing cells of *Acetobacterium woodii*. The dry cell weight of the cell concentration at the time of collection was approximately 3 g/L and having a pH value of approximately 6.1. A volume of cell culture was spun down at 4,100 RPM for 10 minutes. Cell pellets were re-suspended in the same volume of TrisHCl as the volume of culture media that was removed after centrifugation (so that samples were not concentrated or diluted). Multiple volumes of cell culture were subjected to pH modification through addition of 0.5M NaOH so that the final pH of the culture broth was between 6 and 10. Samples were processed between 10,000 and 20,000 psi for one passes. Each sample was spun down at 9,800 RPM for 30 minutes. The supernatant was collected and a Lowry-based protein assay was used to determine protein concentration in the soluble fraction.

Data, shown in Table 11, indicates that an increase in pH of cell sample prior to microfluidization enhances protein solubility. Specifically, when the pH is increasing, the recovery of soluble protein is enhanced.

TABLE 11

Ruptured Protein Recovered by Percentage (%)

| Sample | Passes through microfluidizer | mg/ml | Recovery % |
|---|---|---|---|
| pH 6-6.5 | 1 | 1.5-2.0 | 60-65 |
| pH 6.5-7.5 | 1 | 2.0-2.2 | 65-72.5 |
| pH 7.5-8.5 | 1 | 2.2-2.3 | 72.5-76 |
| pH 8.5-9.5 | 1 | 2.3-2.5 | 76-80 |

Example 16. Determination of the Effect of Lysozyme on Soluble Protein Recovery Samples were collected from a high cell density fermentation vessel. A volume of cell culture was spun down and re-suspended in TrisHCl buffer in the same manner as stated before. The pH of the culture broth was increased to pH 8 using 0.5M sodium hydroxide. To determine the effect of enzyme pre-treatment, 0.5 mg/ml lysozyme was used. For the culture broth samples, incubation with lysozyme lasted ~30 minutes at room temperature. For the TrisHCl samples, incubation with lysozyme lasted ~45 minutes at room temperature (difference due to delay in processing with the microfluidizer as the bottleneck).

Samples were processed between 10,000 and 20,000 psi for one or multiple passes. Controls were also run where samples were not processed through the microfluidizer. Each sample was spun down at 13,300 RPM for 6 minutes. The supernatant was collected and Lowry-based and Bradford-based protein assays were used to determine protein concentration in the soluble fraction and the results are shown in Table 12.

TABLE 12

Ruptured Protein Recovered by Percentage (%)

| Sample | # of passes | mg/ml | % Protein Recovery |
|---|---|---|---|
| Culture Broth | 1-4 | 4-9 | 25-46 |
| Culture Broth w/lysozyme | 1-4 | 4.5-10 | 25-52 |
| TrisHCl | 1-4 | 4.5-9 | 26-46 |
| TrisHCl w/lysozyme | 1-4 | 5-12 | 28-64 |
| Reactor supernatant | 0 | 0.5-1 | 0.02-4.5 |

TABLE 12-continued

Ruptured Protein Recovered by Percentage (%)

| Sample | # of passes | mg/ml | % Protein Recovery |
|---|---|---|---|
| TrisHCl w/lysozyme | 0 | 2-5 | 4-25 |
| Culture Broth | 0 | 1-2 | 0.25-8.5 |
| Culture Broth w/lysozyme | 0 | 2-5 | 3-22 |

Example 17. Determination of Effect of Decreasing Lysozyme Concentration and Extending Incubation Time Samples were collected from a high cell density fermentation vessel and were concentrated via centrifugation for 10 minutes at 4,000 RPM. Culture broth pH was adjusted to 7-10. Some samples were incubated at 37 C with 100 ng/ml of lysozyme for an hour. Samples were taken every 10 minutes to monitor lysozyme activity. Large samples at 30 minutes and 1 hour were taken and processed through the microfluidizer at 10,000 to 20,000 psi for one or multiple passes. Each sample was spun down at 13,300 RPM for 6 minutes. The supernatant was collected and a Lowry-based protein assay was used to determine protein concentration in the soluble fraction and the results are shown in Table 13.

Example 18. Effect of pH and Cell Concentration on Extraction of Protein

Samples from the high cell density fermentation vessel were diluted to concentrations between 1 and 10 g/L via centrifugation and resuspension in culture media. The culture broth pH was adjusted to between 6 and 10 using 0.5M sodium hydroxide. Samples (including un-modified culture broth at fermentation pH) were processed between 10,000 and 20,000 psi through the microfluidizer for one or multiple passes. Similarly, undiluted culture purge from the high cell density fermentation vessel was processed at one acidic pH value and one alkaline pH value. Each sample was spun down at 13,300 RPM for 6 minutes.

TABLE 13

Ruptured Protein Recovered by Percentage (%)

| Enzyme | Sample | Cell Concentration, g/L | Microfluidizer pressure, psi | mg/ml | Soluble Protein Recovery % |
|---|---|---|---|---|---|
| None | Supernatant | — | 0 | 0.5-1 | — |
| None | Culture broth | 10-15 | 0 | 1-2 | 7-10 |
| | | | 10,000-20,000 | 5-10 | 42-52 |
| | | 40-50 | 0 | 1.5-3 | 3.5-4.5 |
| | | | 10,000-20,000 | 15-20 | 35-46 |
| Lysozyme | Culture Broth | 40-50 | 0 | 1.5-2.3 | 3.5-5 |
| | | | 10,000-20,000 | 15-20 | 35-46 |

The supernatant was collected and a Lowry-based protein assay was used to determine protein concentration in the soluble fraction. Table 14 indicates that as pH of the culture broth increases prior to microfluidization, the amount of protein recovered in the soluble fraction increases.

TABLE 14

Recovery of Ruptured Proteins (Protein Concentration indicated)

| Sample | Harvested Cells (Concentration: g/L) | pH of the culture broth | Ruptured Protein (mg/ml) |
|---|---|---|---|
| 1 | 1 | 4-5 | 0.92 |
| 2 | 1 | 6-7 | 1.03 |
| 3 | 1 | 8-9 | 1.23 |
| 4 | 5 | 4-5 | 1.3 |
| 5 | 5 | 6-7 | 2.7 |
| 6 | 5 | 8-9 | 3 |
| 7 | 10 | 4-5 | 1.7 |
| 8 | 10 | 6-7 | 4.3 |
| 9 | 10 | 8-9 | 5.0 |
| 10 | 18.5 | 4-5 | 7.1 |
| 10 | 18.5 | 8-9 | 8.9 |

Figure 8A:
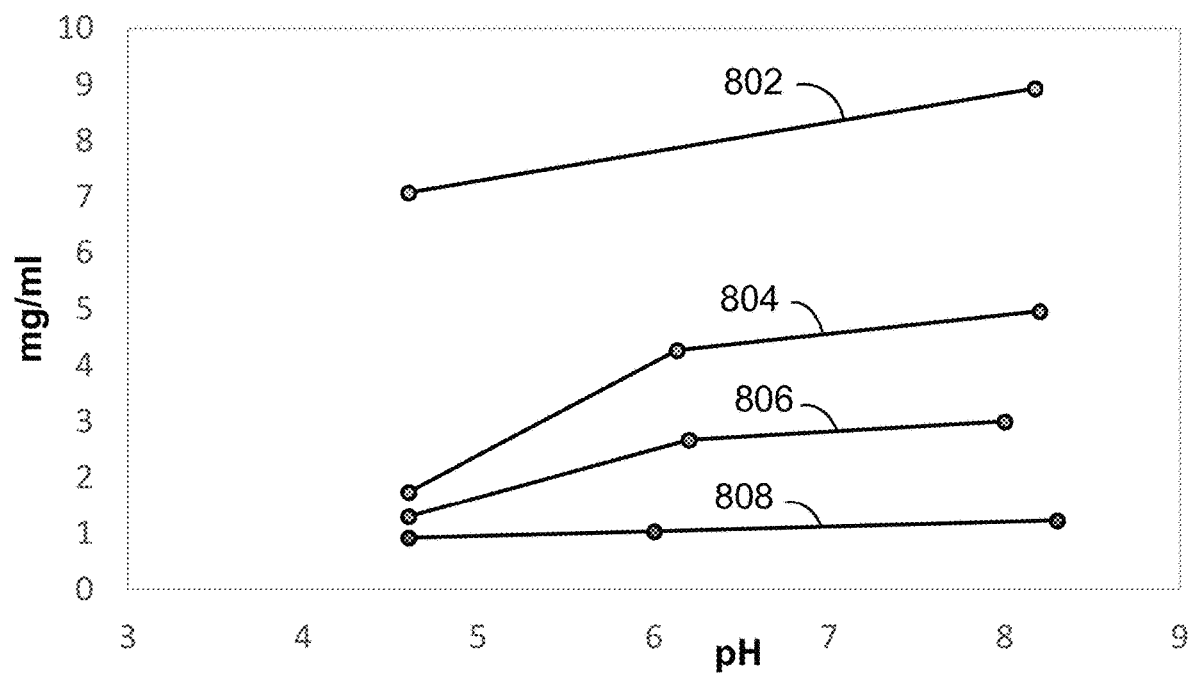
FIG. 8A shows a graph of an example of soluble protein concentrations in homogenate obtained from a rupturing device after rupturing anaerobic bacterial cells within an example of a cell-containing suspension, according to one or more embodiments of the invention.

FIG. 8A illustrates a graph of soluble protein obtained from the rupturing device 460, 560 or 660 and from cell membranes of the anaerobic bacterial cells within the cell-containing suspension, according to one or more embodiments of the invention.

The rupturing devices selected to conduct the rupturing process can be microfluidizer and other commercially available devices. In this FIG. 8A, the rupturing devices selected to conduct the rupturing process is a microfluidizer.

The rupturing process inside the rupturing device 460, 560 or 660 can be conducted under different variables, including pressure and times of passes. In this FIG. 8A, the rupturing process is conducted to the pressure of 15,000 pounds per square inch (psi) against the cell-containing suspension and under only one pass.

The cell-containing suspension selected for undergoing the rupturing process inside the rupturing device 460, 560 or 660 can be of different densities. In this FIG. 8A, four streams of cell-containing suspensions are selected for this rupturing process inside the rupturing device 460, 560 or 660. Each of the densities of the cell-containing suspensions are 1 g/L, 5 g/L, 10 g/L and 18.5 g/L.

The y axis of the line 802 represents the yield of the protein from the cell homogenate ruptured and obtained from the rupturing device 460, 560 or 660 prepared under different pH conditions (X-axis) from anaerobic bacterial cells within the cell-containing suspension with a density of 18.5 g/L, according to one or more embodiments of the invention.

The y axis of the line 804 represents the yield of the protein from the cell homogenate ruptured and obtained from the rupturing device 460, 560 or 660 prepared under different pH conditions (X-axis) from anaerobic bacterial cells within the cell-containing suspension with a density of 10 g/L, according to one or more embodiments of the invention.

The y axis of the line 806 represents the yield of the protein from the cell homogenate ruptured and obtained from the rupturing device 460, 560 or 660 prepared under different pH conditions (X-axis) from anaerobic bacterial cells within the cell-containing suspension with a density of 5 g/L plotted against different pH conditions, according to one or more embodiments of the invention.

The y axis of the line 808 represents the yield of proteins from the cell homogenate ruptured and obtained from the rupturing device 460, 560 or 660 a prepared under different pH conditions (X-axis) from anaerobic bacterial cells within the cell-containing suspension with a density of 1 g/L, according to one or more embodiments of the invention.

The cell-containing suspension selected for undergoing the rupturing process inside the rupturing device 460, 560 or 660 can be of different pH value, within a range of 1 to 14. The pH value of the cell-containing suspension can be adjusted by various methods, including acid, base, or salt addition, or combinations thereof. Here in FIG. 8A, the pH value of cell-containing suspension is adjusted to approximately 6 or 8 using 0.5M sodium hydroxide. The pH value of the cell-containing suspension can be adjusted before cell-containing suspension being ruptured inside the rupturing device 460, 560 or 660. For example, the pH value of the cell-containing suspension can be adjusted inside the cell-containing holding tank 445, 545, or 645.

Example 19. Effect of pH on High Concentrations on Protein-Containing Suspensions Samples were collected from a high cell density fermentation vessel and concentrated 3-fold by centrifuging cells for 10 minutes at 4,000 RPM. Cell pellets were re-suspended in culture media. The culture media was adjusted to pH between 5 and 10 using concentrated sodium hydroxide. For example, samples were concentrated to 45 g/L by centrifuging cells for 10 minutes at 4,000 RPM. Cell pellets were resuspended in culture media. The resulting cell mixture pH was modified to 5, 6, 7, or 8 using 0.5M sodium hydroxide. Samples were processed at 15,000 PSI through the microfluidizer for one pass. Each sample was spun down at 13,300 RPM for 6 minutes. The supernatant was collected and a Lowry-based protein assay was used to determine protein concentration in the soluble fraction.

Figure 8B:
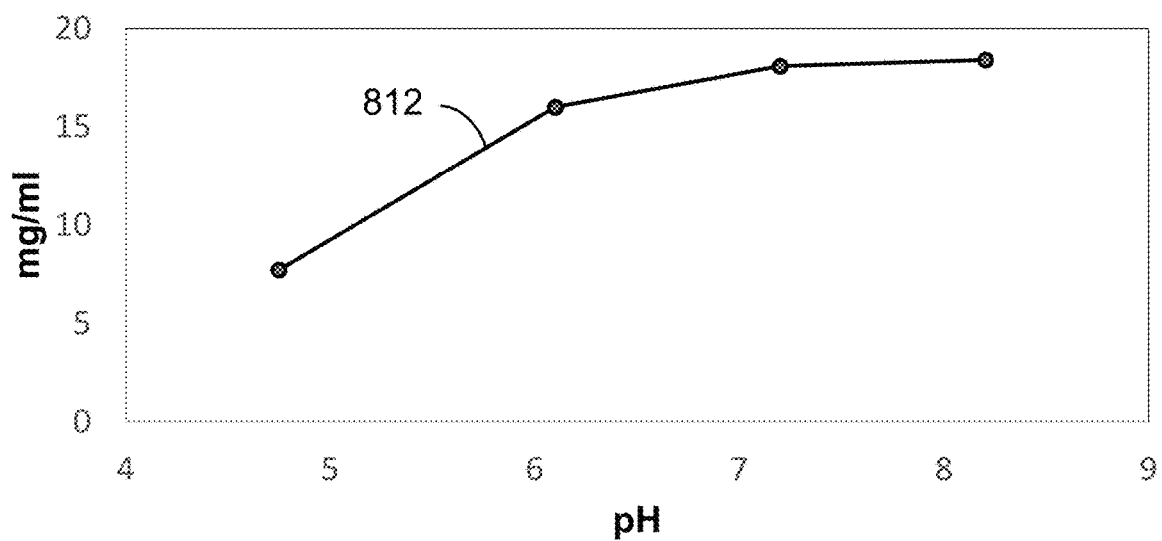
FIG. 8B shows another graph of another example of soluble protein concentrations obtained from a rupturing device after rupturing cell membranes of the anaerobic bacterial cells within another example of a cell-containing suspension, according to one or more embodiments of the invention.

FIG. 8B illustrates a chart of the yield of soluble protein obtained from the rupturing device 460, 560 or 660 and from cell membranes of the anaerobic bacterial cells within the cell-containing suspension, according to one or more embodiments of the invention.

In FIG. 8B, the rupturing devices selected to conduct the rupturing process is a microfluidizer. In FIG. 8B, the rupturing process is conducted to the pressure between 10,000 and 20,000 psi against the cell-containing suspension for one or multiple passes. The supernatant was collected via centrifugation at 13,300 RPM and the protein was analyzed using a Lowry-based protein assay. Table 15 indicates that increasing the pH of the culture broth from 4-5 to 6-10 significantly increases the percent of protein that is recovered in the soluble fraction.

The y axis of the line 812 represents the effect of pH on the yield of protein from the cell homogenate ruptured and obtained from the rupturing device 460, 560 or 660 prepared under different pH conditions (X-axis) from anaerobic bacterial cells within the cell-containing suspension with a density of 45 g/L from a change in pH value of the cell-containing suspension, according to one or more embodiments of the invention.

TABLE 15

Recovery of Ruptured Proteins Purified form from 45 g/L of cells (protein concentration as indicated in mg/mL)

| Sample | pH of cultured broth | Protein concentration (mg/mL) |
|---|---|---|
| 1 | 4-5 | 7.7 |
| 2 | 6-7 | 16 |
| 3 | 7.1-8 | 18.1 |
| 4 | 8.1-10 | 18.4 |

Example 20: Determination of pH Effect in the Homogenate on Protein Recovered after Rupturing Through One or More Rupturing Devices Samples were collected from a high cell density fermentation vessel containing cells of *Clostridium ljungdahlii*. The cell concentration at the time of collection was approximately 18 g/L and having a pH value of approximately 4.5. A volume of cell culture was spun down at 4,000 RPM for 10 minutes. Samples were processed between 15,000 psi for zero or one pass. Then, multiple volumes of cell culture were subjected to pH modification through addition of 0.5M NaOH or $NH_4OH$ so that the final pH of the culture broth was between approximately 8. Each sample was spun down at 13,3000 RPM for 6 minutes. The supernatant was collected and a Lowry-based protein assay was used to determine protein concentration in the soluble fraction.

Data, shown in Table 16, indicates that an increase in pH of cell homogenate after microfluidization enhances protein solubility. Specifically, when the pH is increasing, the recovery of soluble protein is enhanced.

TABLE 16

| Protein Recovery Rate by Percentage (%) | | | | |
|---|---|---|---|---|
| pH value of the Sample | pH adjusting agent | Passes | mg/ml | Recovery % |
| 4.5 | none | 0 | 0.4 | 1.5-2 |
| 4.5 | none | 1 | 3.3 | 15-20 |
| 8 | $NH_4OH$ | 1 | 6.4 | 30-35 |
| 8 | NaOH | 1 | 8.3 | 40-45 |

Example 21: Determination of pH Effect in the Cell Samples on Protein Recovered without being Ruptured Samples were collected from a high cell density fermentation vessel containing cells of *Clostridium ljungdahlii*. The cell concentration at the time of collection was approximately 18 g/L and having a pH value of approximately 4.5. A volume of cell culture was spun down at 4,000 RPM for 10 minutes. Then, multiple volumes of cell culture were subjected to pH modification through addition of 0.5M NaOH or $NH_4OH$ so that the final pH of the culture broth was approximately 8. Next, samples were not processed between 15,000 psi. Each sample was spun down at 13,300 RPM for 6 minutes. The supernatant was collected and a Lowry-based protein assay was used to determine protein concentration in the soluble fraction. Data, shown in Table 17, indicates that an increase in pH of cell samples before microfluidization enhances protein solubility. Specifically, when the pH is high, the recovery of soluble protein is enhanced.

TABLE 17

| Protein Recovery Rate by Percentage (%) | | | | |
|---|---|---|---|---|
| Sample's pH value | pH adjusting agent | Passes | mg/ml | Recovery % |
| 4.5 | None | 0 | 0.3-0.5 | 1.5-2.0 |
| 8 | $NH_4OH$ | 0 | 0.4-0.6 | 2.1-2.6 |
| 8 | NaOH | 0 | 0.8-1.0 | 4.5-5.0 |

Example 22: Determination of pH Effect in the Cell Samples on Protein Recovered after Rupturing Through One or More Rupturing Devices Samples were collected from a high cell density fermentation vessel containing cells of *Clostridium ljungdahlii*. The cell concentration at the time of collection was approximately 18 g/L and having a pH value of approximately 4.5. A volume of cell culture was spun down at 4,000 RPM for 10 minutes. Then, multiple volumes of cell culture were subjected to pH modification through addition of 0.5M NaOH or NH4OH so that the final pH of the culture broth was approximately 8. Next, samples were processed between 15,000 psi for one pass. Each sample was spun down at 13,300 RPM for 6 minutes. The supernatant was collected and a Lowry-based protein assay was used to determine protein concentration in the soluble fraction.

Data, shown in Table 18, indicates that an increase in pH of cell samples before microfluidization enhances protein solubility. Specifically, when the pH is high, the recovery of soluble protein is enhanced.

TABLE 18

| Protein Recovery Rate by Percentage (%) | | | | |
| --- | --- | --- | --- | --- |
| Sample's pH value | pH adjusting agent | Passes | mg/ml | Recovery % |
| 4.5 | None | 1 | 3.0-3.5 | 15-20 |
| 8 | NaOH | 1 | 10.0-10.5 | 50-55 |
| 8 | NH$_4$OH | 1 | 11.0-11.5 | 55-60 |

While the foregoing is directed to embodiments of the present invention, other and further embodiments of the invention may be devised without departing from the basic scope thereof, and the scope thereof is determined by the claims that follow.

What is claimed:

1. A process for obtaining a high recovery rate of a protein-containing product purified from anaerobic bacteria cells, comprising:
   fermenting a gaseous substrate with anaerobic bacteria cells into a fermentation liquid broth inside a fermentation vessel, wherein the fermentation liquid broth is at a first pH value;
   separating an amount to the fermentation liquid broth being delivered from the fermentation vessel at a starting cell concentration into a cell-free permeate solution and a cell-containing suspension containing the anaerobic bacteria cells;
   supplying one or more pH-adjusting agents to adjust the pH of cell-containing suspension, wherein pH of the cell-containing suspension is adjusted to a second pH value higher than the first pH value;
   rupturing cell membranes of the anaerobic bacteria cells contained within the cell-containing suspension into a homogenate having the protein-containing product at a first protein recovery rate, wherein the first protein recovery rate is a percentage of a protein concentration (grams per liter) of the protein-containing product divided by the starting cell concentration (grams per liter); and
   fractionating the homogenate into a first protein-containing portion at a second protein recovery rate and a protein-containing cell debris portion at a third protein recovery rate.

2. The process of claim 1, wherein the second pH value is in a range of 5 to 12.

3. The process of claim 1, wherein the second pH value is in a range of 7 to 12.

4. The process in claim 1, wherein the one or more pH-adjusting agents is selected from the group consisting of sodium hydroxide, potassium hydroxide, ammonium hydroxide, bicarbonate, and a combination thereof.

5. The process in claim 1, wherein one or more pH-adjusting agents to the cell-containing suspension is added prior to the rupturing the cell membranes of the anaerobic bacteria cells.

6. The process in claim 1, wherein one or more pH-adjusting agents to the cell-containing suspension is added after the rupturing the cell membranes of the anaerobic bacteria cells.

7. The process of claim 1, further comprising:
   holding the cell-containing suspension containing the anaerobic bacterial cells at the second pH value in a cell-containing holding tank prior to rupturing the cell membranes of the anaerobic bacteria cells.

8. The process of claim 1, further comprising:
   holding the cell-containing suspension containing the anaerobic bacterial cells at the second pH in a cell-containing holding tank after rupturing the cell membranes of the anaerobic bacteria cells.

9. The process of claim 1, wherein the first protein recovery rate is between 10% and 95%.

10. The process of claim 1, wherein the second protein recovery rate is between 10% and 85% and the third protein recovery rate is between 10% and 75%.

11. A process for increasing a recovery rate of a protein containing product purified from anaerobic bacteria cells, comprising:
    fermenting a gaseous substrate with anaerobic bacteria cells into a fermentation liquid broth inside a fermentation vessel, wherein the fermentation liquid broth is at a first pH value;
    separating the fermentation liquid broth being delivered from the fermentation vessel into a cell-free permeate solution and a cell-containing suspension containing the anaerobic bacteria cells;
    supplying one or more pH-adjusting agents to adjust the pH of cell-containing suspension, wherein pH of the cell-containing suspension is adjusted to a second pH value higher than the first pH value;
    rupturing cell membranes of the anaerobic bacteria cells contained within the cell-containing suspension into a homogenate having the protein-containing product at a first protein recovery rate, wherein the first protein recovery rate is a percentage of a protein concentration (grams per liter) of the protein-containing product divided by the starting cell concentration (grams per liter);
    fractionating the homogenate into a first protein-containing portion at a second protein recovery rate and a protein-containing cell debris portion at a third protein recovery rate using a first fractionator;
    delivering the first protein-containing portion to a second fractionator; and
    fractionating the first protein-containing portion into a second protein-containing portion using a second fractionator; and
    collecting the second protein-containing portion.

12. The process of claim 11, wherein the second pH value is in a range of 7 to 12, and the one or more pH-adjusting agents is selected from the group consisting of sodium hydroxide, potassium hydroxide, ammonium hydroxide, bicarbonate, and a combination thereof.

13. The process in claim 11, wherein one or more pH-adjusting agents to the cell-containing suspension is added prior to the rupturing the cell membranes of the anaerobic bacteria cells.

14. The process in claim 11, wherein one or more pH-adjusting agents to the cell-containing suspension is added after the rupturing the cell membranes of the anaerobic bacteria cells.

* * * * *